US012760343B2

(12) United States Patent
Mulhall

(10) Patent No.: US 12,760,343 B2
(45) Date of Patent: Oct. 13, 2026

(54) GENETICALLY ENGINEERED MICROORGANISMS

(71) Applicant: CroBio Ltd, Cheshire (GB)

(72) Inventor: Ross Mulhall, Liverpool (GB)

(73) Assignee: CroBio Ltd, Cheshire (GB)

( * ) Notice: Subject to any disclaimer, the term of this patent is extended or adjusted under 35 U.S.C. 154(b) by 728 days.

(21) Appl. No.: 17/780,186

(22) PCT Filed: Dec. 3, 2020

(86) PCT No.: PCT/EP2020/084505

§ 371 (c)(1),
(2) Date: May 26, 2022

(87) PCT Pub. No.: WO2021/110856

PCT Pub. Date: Jun. 10, 2021

(65) Prior Publication Data

US 2023/0034438 A1 Feb. 2, 2023

(30) Foreign Application Priority Data

Dec. 3, 2019 (GB) ..................................... 1917651
Oct. 15, 2020 (GB) ..................................... 2016372

(51) Int. Cl.

| | |
|---|---|
| ***C12P 19/04*** | (2006.01) |
| ***A01N 63/27*** | (2020.01) |
| ***C07K 14/195*** | (2006.01) |
| ***C12N 9/42*** | (2006.01) |
| ***C12N 15/52*** | (2006.01) |
| ***C12N 15/78*** | (2006.01) |

(52) U.S. Cl.

CPC .............. *C12P 19/04* (2013.01); *A01N 63/27* (2020.01); *C07K 14/195* (2013.01); *C12N 9/2437* (2013.01); *C12N 9/2445* (2013.01); *C12N 15/52* (2013.01); *C12N 15/78* (2013.01)

(58) Field of Classification Search

CPC ....... C12P 19/04; A01N 63/27; C07K 14/195; C12N 9/2437; C12N 9/2445; C12N 15/52; C12N 15/78; C12N 1/20; A01H 3/00

See application file for complete search history.

(56) References Cited

U.S. PATENT DOCUMENTS

| | | | |
|---|---|---|---|
| 2004/0054165 A1 | 3/2004 | Rainey | |
| 2008/0085520 A1 | 4/2008 | Nobles, Jr. | |
| 2018/0148696 A1* | 5/2018 | Lee ................ | C12Y 204/01012 |

FOREIGN PATENT DOCUMENTS

| | | |
|---|---|---|
| CN | 107299073 | 10/2017 |
| CN | 108060112 | 5/2018 |
| EP | 0916731 | 5/1999 |
| EP | 3293261 | 3/2018 |
| EP | 3315598 | 5/2018 |
| WO | 1998039455 | 9/1998 |
| WO | 2002004526 | 1/2002 |
| WO | 2014104310 A1 | 7/2014 |
| WO | 2018035411 | 2/2018 |
| WO | 2019084059 A2 | 5/2019 |
| WO | 2019084342 A1 | 5/2019 |
| WO | 2025046078 A1 | 3/2025 |

OTHER PUBLICATIONS

Mangayil R, Rajala S, Pammo A, Sarlin E, Luo J, Santala V, Karp M, Tuukkanen S. Engineering and characterization of bacterial nanocellulose films as low cost and flexible sensor material. ACS applied materials & interfaces. Jun. 7, 2017;9(22):19048-56. (Year: 2017).*

Spiers AJ, Folorunso AO, Zawadzki K, Deeni YY, Koza A, Moshynets O. Cellulose expression in Pseudomonas fluorescens SBW25 and other environmental pseudomonads. InCellulose: medical, pharmaceutical and electronic applications Aug. 29, 2013. InTech (Year: 2013).*

Augimeri RV, Strap JL. The phytohormone ethylene enhances cellulose production, regulates CRP/FNRKx transcription and causes differential gene expression within the bacterial cellulose synthesis operon of Komagataeibacter (Gluconacetobacter) xylinus. Frontiers in microbiology. Dec. 22, 2015;6:1459. (Year: 2015).*

Lally RD, Galbally P, Moreira AS, Spink J, Ryan D, Germaine KJ, Dowling DN. Application of endophytic Pseudomonas fluorescens and a bacterial consortium to *Brassica napus* can increase plant height and biomass under greenhouse and field conditions. Frontiers in Plant Science. Dec. 22, 2017;8:2193. (Year: 2017).*

Buldum G, Bismarck A, Mantalaris A. Recombinant biosynthesis of bacterial cellulose in genetically modified *Escherichia coli*. Bioprocess and biosystems engineering. Feb. 2018;41:265-79. (Year: 2018).*

Meyers A, Furtmann C, Gesing K, Tozakidis IE, Jose J. Cell density-dependent auto-inducible promoters for expression of recombinant proteins in Pseudomonas putida. Microbial Biotechnology. Sep. 2019;12(5):1003-13. (Year: 2019).*

Bainton NJ, Lynch JM, Naseby D, Way JA. Survival and ecological fitness of Pseudomonas fluorescens genetically engineered with dual biocontrol mechanisms. Microbial ecology. Nov. 2004;48(3):349-57. (Year: 2004).*

Mavrodi DV, Loper JE, Paulsen IT, Thomashow LS. Mobile genetic elements in the genome of the beneficial rhizobacterium Pseudomonas fluorescens Pf-5. BMC microbiology. Jan. 13, 2009;9(1):8. (Year: 2009).*

(Continued)

*Primary Examiner* — Jennifer M.H. Tichy
*Assistant Examiner* — Emily F Eix
(74) *Attorney, Agent, or Firm* — FisherBroyles, LLP; Adam K. Whiting; Adelaide K. Leitzel

(57) ABSTRACT

The invention relates to genetically engineered microorganisms, such as bacteria, modified to increase production of cellulose and methods of producing said genetically engineered microorganisms. The invention also relates to the use of these genetically engineered microorganisms in agriculture.

22 Claims, 5 Drawing Sheets

Specification includes a Sequence Listing.

(56) References Cited

OTHER PUBLICATIONS

Jorjani M, Heydari A, Zamanizadeh HR, Rezaee S, Naraghi L. Development of Pseudomonas fluorescens and Bacillus coagulans based bioformulations using organic and inorganic carriers and evaluation of their influence on growth parameters of sugar beet. Journal of biopesticides. May 1, 2011;4(2):180. (Year: 2011).*

Liu Z, Beskrovnaya P, Melnyk RA, Hossain SS, Khorasani S, O'Sullivan LR, Wiesmann CL, Bush J, Richard JD, Haney CH. A genome-wide screen identifies genes in rhizosphere-associated Pseudomonas required to evade plant defenses. MBio. Dec. 21, 2018;9(6):10-128. (Year: 2018).*

Buldum, G., et al., "Recombinant biosynthesis of bacterial cellulose in genetically modified *Escherichia coli*", Bioprocess and Biosystems Engineering (2018) 41:265-279.

Spiers, A., et al., "Cellulose Expression in Pseudomonas fluorescens SBW25 and Other Environmental Pseudomonads", in: Cellulose—Medical, Pharmaceutical and Electronic Applications, InTech, Aug. 29, 2013, abstract, p. 18-19.

Bae, S. O. et al. (2004) 'Features of bacterial cellulose synthesis in a mutant generated by disruption of the diguanylate cyclase 1 gene of Acetobacter xylinum BPR 2001', Applied Microbiology and Biotechnology, 65(3), pp. 315-322. doi: 10.1007/s00253-004-1593-7.

Bailey, M. J. et al. (1995) 'Site directed chromosomal marking of a fluorescent pseudomonad isolated from the phytosphere of sugar beet; stability and potential for marker gene transfer.', Molecular Ecology, 4(6), pp. 755-764. doi: 10.1111/j.1365-294X.1995.tb00276.x.

Bashan, Y., et al. (2002) 'Alginate microbeads as inoculant carriers for plant growth-promoting bacteria'. Biol Fertil Soils, 35, 359-368.

Baynham, P. J. et al. (2006) 'The Pseudomonas aeruginosa ribbon-helix-helix DNA-binding protein AlgZ (AmrZ) controls twitching motility and biogenesis of type IV pili', Journal of Bacteriology, 188(1), pp. 132-140. doi: 10.1128/JB.188.1.132-140.2006.

Brautaset, T. et al. (1994) 'Nucleotide sequence and expression analysis of the Acetobacter xylinum phosphoglucomutase gene', Microbiology, 140(5), pp. 1183-1188. doi: 10.1099/13500872-140-5-1183.

Florea, M. et al. (2016). 'Engineering control of bacterial cellulose production using a genetic toolkit and a new cellulose producing strain'. PNAS; 113(24): E3431-40.

Jang, W. D. et al. (2019) 'Genomic and metabolic analysis of Komagataeibacter xylinus DSM 2325 producing bacterial cellulose nanofiber', Biotechnology and Bioengineering, (July), pp. 1-10. doi: 10.1002/bit.27150.

Jozala, A. F., et al. (2014) 'Bacterial cellulose production by Gluconacetobacter xylinus by employing alternative culture media'. Appl Microbiol Biotechnol; 99(3): 1181-90. Doi: 1007/s00253-014-6232-3.

Kawano, S., et al. (2008). 'Regulation of endoglucanase gene (cmcax) expression in Acetobacter xylinum'. J. Biosci. Bioeng. 106, 88-94. doi: 10.1263/jbb.106.88.

Klemm, D. et al. (2001) 'Bacterial synthesized cellulose—artificial blood vessels for microsurgery', Progress in Polymer Science, 26(9), pp. 1561-1603. doi: 10.1016/S0079-6700(01)00021-1.

Koo, H. M. et al. (2000) 'Cloning, sequencing, and expression of UDP-glucose pyrophosphorylase gene from acetobacter xylinum BRC5', Bioscience, Biotechnology and Biochemistry, 64(3), pp. 523-529. doi: 10.1271/bbb.64.523.

Meyers A, Furtmann C, Gesing K, Tozakidis IEP, Jose J. 2019. Cell density-dependent auto-inducible promoters for expression of recombinant proteins in Pseudomonas putida. Microb Biotechnol 12:1003-1013.

Rainey, P. B. and Bailey, M. J. (1996) 'Physical and genetic map of the Pseudomonas fluorescens SBW25 chromosome', Molecular Microbiology, 19(3), pp. 521-533. doi: 10.1046/j.1365-2958.1996.391926.x.

Ryngajłło, M. et al. (2019) 'Comparative genomics of the Komagataeibacter strains—Efficient bionanocellulose producers', MicrobiologyOpen, 8(5), pp. 1-25. doi: 10.1002/mbo3.731.

Sambrook, J., & R. (2001) 'Molecular cloning: a laboratory manual', Cold Spring Harbor Laboratory Press.

Standal, R., et al. (1994). 'A new gene required for cellulose production and a gene encoding cellulolytic activity in Acetobacter xylinum are colocalized with the bcs operon'. J. Bacteriol. 176, 665-672.

Tajima, K., et al. (2001). 'Cloning and sequencing of the beta-glucosidase gene from Acetobacter xylinum ATCC 23769'. DNA Res. 8, 263-269. doi: 10.1093/dnares/8.6.263.

Vandamme, E.J., et al. (1998). 'Improved production of bacterial cellulose and its application potential'. Polymer Degradation and Stability. 59 (1-3): 93-99. doi:10.1016/S0141-3910(97)00185-7.

Walz, A. et al. (2002) 'A gene encoding a protein modified by the phytohormone indoleacetic acid', Proceedings of the National Academy of Sciences of the United States of America, 99(3), pp. 1718-1723. doi: 10.1073/pnas.032450399.

Wong, H. C. et al. (1990) 'Genetic organization of the cellulose synthase operon in Acetobacter xylinum', Proceedings of the National Academy of Sciences of the United States of America, 87(20), pp. 8130-8134. doi: 10.1073/pnas.87.20.8130.

English language translation of Japanese Office Action issued in App. No. JP2022-533350, dated Nov. 22, 2024, 7 pages.

International Search Report and Written Opinion issued in App. No. PCT/EP2024/074298, dated Feb. 13, 2025, 28 pages.

Nielsen, Lindsey, Xiaohong Li, and Larry J. Halverson. "Cell-cell and cell-surface interactions mediated by cellulose and a novel exopolysaccharide contribute to Pseudomonas putida biofilm formation and fitness under water-limiting conditions." Environmental microbiology 13.5 (2011): 1342-1356.

Spiers, Andrew J., et al. "Adaptive divergence in experimental populations of Pseudomonas fluorescens. I. Genetic and phenotypic bases of wrinkly spreader fitness." Genetics 161.1 (2002): 33-46.

* cited by examiner

Fig. 4A
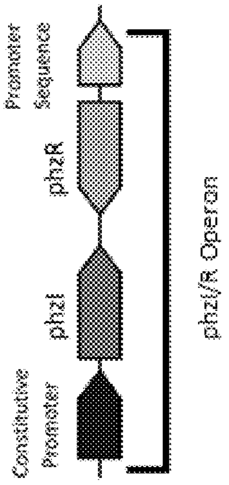
Fig. 4B
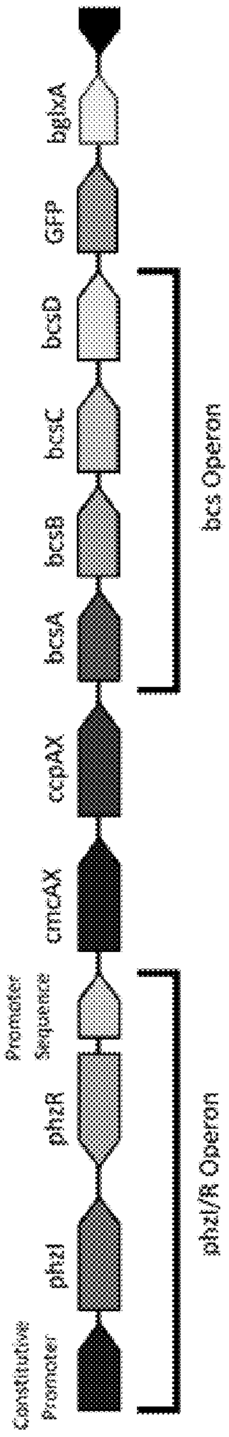
Fig. 4

Fig. 5B
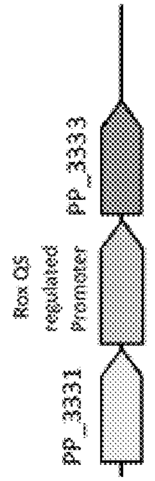
FIG. 5A
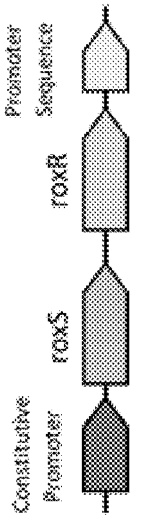
Fig. 5C
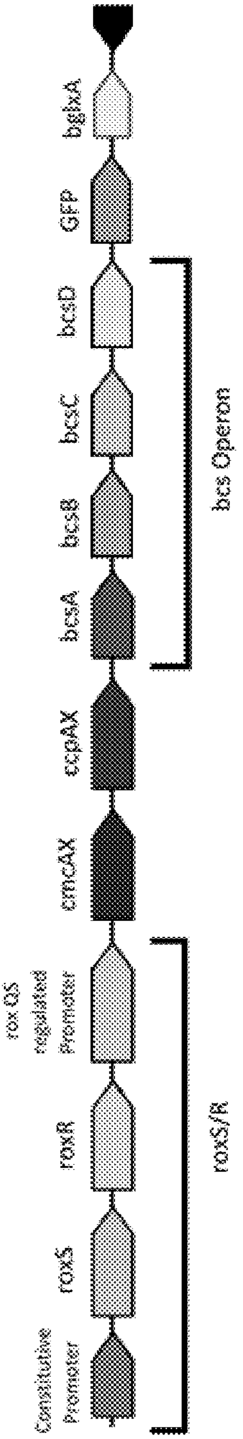
Fig. 5

SEQUENCE LISTING

```
<160> NUMBER OF SEQ ID NOS: 18

<210> SEQ ID NO 1
<211> LENGTH: 30
<212> TYPE: DNA
<213> ORGANISM: Artificial Sequence
<220> FEATURE:
<223> OTHER INFORMATION: host organism attB insertion site

<400> SEQUENCE: 1

tgagttcgaa tctcaccgcc tccgccatat                                        30


<210> SEQ ID NO 2
<211> LENGTH: 1080
<212> TYPE: DNA
<213> ORGANISM: Artificial Sequence
<220> FEATURE:
<223> OTHER INFORMATION: cmcAx gene

<400> SEQUENCE: 2

atgctgttgg attttatgaa gctgcaaaaa caggtatccg gaatgggacg tcgttctttc      60

ctgtctgtca tggcggcagc tggcagtatt cctttccttt ctaccgccct ggccgcggat     120

gacccggcca taaacgcgca atgggccatc ttccgcgcca agtatttcca ccccgacggc     180

cgtatcatcg acacaggcaa cagtggcgaa tcccatagcg aggggcaggg ctacggcatg     240
```

```
cttttcgccg cgacggcggg tgatcaggcc acgttcgagg ccatgtggtc ctggacacgc    300

gccaacctgc agcacaagac cgatgccctg ttctcctggc gctatctgga cgggcataac    360

ccgccggtcg cggacaagaa caacgcgacg gatggcgacc tgctgatagc cctgggtctg    420

gtccgtgccg gacggctgtg gaagcgcgct gactatattc aggatgctat agccatctat    480

ggcgacgtgc tgaagctcat gaccctgcag gtcggtccct atctggtgct tctgcccggc    540

ggcgtggggt ttgccaccaa ggattcggtc acgctcaacc tgtcctatta tgtcatgccc    600

tcgctcatgc aggccttcgc gctgacgggc gacgcacgct ggcagaaggt gatgggagat    660

ggtctgatca tcataaacca ggggcgattc ggggagtgga agctcccgcc tgactggctt    720

tcgatcaacc gccagaacgg gcatttctcc atagccaatg gctggccgcc gcgattctcc    780

tatgatgcga ttcgcgtgcc gctgtatctt tactgggcgc atatgctgtc gccggacctg    840

ctggccgact ttacccgctt ctggaaccat ttcggggcat cggccctgcc ggggtggatt    900

gacctgacca atggtgcccg ctcgccctac aatgcgccac cgggctatct ggccgtggcg    960

acatgttccg gcctgtcatc cgccggtggg ttgccaaccc tggacaaggc gccggattat   1020

tattcggctg ccctgacatt gctggtttat attgcccgtg gtgagggagg tggaatgtga   1080
```

<210> SEQ ID NO 3
<211> LENGTH: 935
<212> TYPE: DNA
<213> ORGANISM: Artificial Sequence
<220> FEATURE:
<223> OTHER INFORMATION: ccpAx gene

<400> SEQUENCE: 3

```
gcatggatat ggacaatccg caggacgtga cgcgcatgct ctccagcggt tatggcctga     60

gcggggaggg gttccactac cattccttca cgcgtcccgt catgctggac atgaccccgg    120

aactgcccca cgattccgtg gacgatacag agcatcatct cgacgataac gtcaccgaac    180

acgaatccgc cccggcaacg gcaccggtgt tcgtgttcga tgcggcacct gagcctgcgg    240

caccacctgt tgttgccgag gccgcgccac cgccacctcc tccgccgccg ccagagcctg    300

cgcctcctga gccgccgccc gcaccgccac cctatacgcc ggttgtaacc cacgtgccgc    360

cgccgccgcc cgtggaggaa acgccggtac ccgaacccgt ggctgaagcg gctgcacctg    420

caaggccccg gcccgtgccg ccggcgcagc ccgcgccgga catggcatcg acgggcgggc    480

gtgaacggcg cgggcttcag ccttttacca cgccgcgtac gccatccgag ccgccggtgt    540

cttcacgtgc ggccgcaccg gccacgccct tcgtccaggc agatgactgg gcgccggtgc    600

caaaggccca gcagcgtcgc ggccagcgtc cgaccgggcc tggtttcttc tttgccaagg    660

ggaatgaccg ggttgcgact gcccggctgt tccagccggt ggcagtggcc cgtcctgctt    720

ccaaacctga ctccaaggtg accacgatga ccaaattcga caagaccgca cagaatgccc    780

ccacggggcg tcgtcctgcg ccatctgaca attcgccaac actgacggaa gttttcatga    840

cactgggcgg tcgtgccacc gaccggctgg tgcccaagcc cagcctgcgt gacgcgctgc    900

tgcgcaagcg tgaggaagaa accgggcaat cctga                               935
```

<210> SEQ ID NO 4
<211> LENGTH: 9102
<212> TYPE: DNA
<213> ORGANISM: Artificial Sequence
<220> FEATURE:
<223> OTHER INFORMATION: a bcs operon, comprising a bcsA gene, a bcsB gene, a bcsC gene and a bcsD gene,

<400> SEQUENCE: 4

```
aatgtcagag gttcagtcgt cagcgcccgc ggaaagttgg tttgatcgcc tttccaacaa     60
gatactgtca ctgcgcggtg ccagttatat cgttggggca ataggcctgt gcgccctgct    120
tgccgcgacc acggttatgc tgtcggtaaa tgaacagctg attgtggcat tagtgtgcgt    180
tgtggtcttt tttatcgtcg gtcggcgcaa aagccgtcgg acgcagatat ttctcgaggt    240
gctttcggcg ctggtgtccc tgcgttatct gacgtggcgg ctgaccgaaa cactggattt    300
cgatacatgg ctccagggta cattgggggt cacgctgctt ctggcggaac tgtacgcgct    360
gtacatgctg ttcctcagct atttccagac catttccccc ctgcaccgcg cgccgctgcc    420
cctgtctccc aatccggaag actggcccac ggtcgacatc ttcatcccga cctatgacga    480
aagcctgggc atcgtgcgtc tgacggtgct gggcgcgctt ggtatcgact ggccaccgga    540
caaggtgaac gtctatatcc ttgatgacgg caagcgtgag gaattcgccc gctttgccga    600
agaatgcggt gcccgctaca ttgcccgtcc cgataacgcg catgccaagg ccggtaacct    660
gaactacgcc attcagcata caagtggcga atacatcctg attctggact gcgatcacat    720
cccgacccgt gcgttcctgc agatctcgat gggatggatg gtcgaggaca agaagatcgc    780
cctgatgcag acgccgcatc acttctattc ccccgatcct ttccagcgta acctggccgt    840
cggttaccgc acgccgcctg aaggcaacct gttctatggt gtcattcagg atggcaacga    900
cttctgggat gcgaccttct tctgtggttc ctgtgccatc ctgcgccgca aggccatcga    960
agagatcaat ggtttcgcaa ccgagaccgt gacggaagat gcccataccg ccctgcgcat   1020
gcagcgcagg gggtggtcga ccgcctatct gcgcattccg ctggccagcg ggctggcgac   1080
ggagcgcctg gtcacgcata tcgggcagcg tatgcgctgg gcccgtggca tgttccagat   1140
cttccgcgtg gataatccca tgctggggcc gggcctgaag ctggggcagc ggctttgcta   1200
tctttcggcc atgacgtcgt tcttcttcgc cattccgcgt gtcatcttcc ttgcctcccc   1260
gctggccttc cttttcttca gccagaatat catcgcggcc tccccccctgg cggtgctggc   1320
ctacgccatt ccccacatgt tccattccgt tgccacggcg gcaaaggtga acaagggatg   1380
gcgctattca ttctggagtg aagtgtacga aaccgtcatg gcgctgttcc tggtgcgggt   1440
gaccatcgtc acgatgatgt tcccctcgaa gggcaagttc aacgtgacgg aaaaaggtgg   1500
cgttctggag aacgaggaat tcgaccttgg tgccacatat ccgaacatca tctttgcggt   1560
catcatggcg attggcctga tgcgcgggct gtttgccctg gccttccagc atctggacat   1620
aatttcagag cgtgcctacg cactcaactg tgtctggtcc gtgatcagtc tcatcatcct   1680
gcttgcggcc attgccgtcg gccgtgagac caagcagatc cgccacagcc atcgtgtcga   1740
tgcgcgaatt ccggtaacgg tttatgatta cgaagggaat tccagccatg gcatcacgca   1800
ggacgtgtcc atgggtggtg tggccattca tatgccgtgg cgcaatgtga caccggacca   1860
gccggtgcag accgttgtcc acgccgtgct ggatggtgag gtggtcaatc tccccgctac   1920
catgatccgc tgtgcgaatg gcaaggcggt ctttacctgg aacatcacct ccctcccgat   1980
tgaagcctct gtcgtccggt tcgtgttcgg tcgcgccgat gcctggctgc agtggaatga   2040
ttacgagcat gatcggccgt tgcgaagcct gtggagcctg atcctcagca tcaaggcgct   2100
gttccgcaag aagggtcgga tgatgatcca tagtcgcccg caaaataaac ccattgcact   2160
gcctgttgag cgcagggagc caacaagcag tcagggtggt cagaaacagg aaggaaagat   2220
cagtcgtgcg gcctcgtgat atgaaaatgg tgtccctgat cgcgctgctg gtctttgcaa   2280
cgggagcgca ggctgcgccg gttgcatcca aagcgccagc cccgcagcct gcgggcgata   2340
```

```
acctgccgcc cctgcccgcc gcggcaccgg ccgccgcggc agccccggcc gggcagcagc   2400
ctgctggcgc cgccagtgcg gcacctgccg tcgatccggc cgctgccagc gccgccgatg   2460
ccatggtgga caatgcggag aatgcgaccg gcgtcggttc ggatgtggcg accgtgcata   2520
cctattccct gcgcgaactt ggcgcggaga acgcgctgac catgcgtggc gcggcccccc   2580
tgcaggggct gcagttcggt attccgggcg accagctcgt cacctcggcg cggcttgtcg   2640
tgtcgggtgc gatgtcaccc aatctccagc ccgataacag cgcggtcacg attacgctga   2700
acgagcagta tatcggcacg ctccggcctg acccgtcaca tccggccttt ggtccgcttt   2760
cctttgacat caaccccatc ttctttgtca gcggcaaccg gctgaacttc aatttctcgg   2820
cagggtcgaa aggatgcacc gacccgagca acggattgca gtgggccagc gtgtccgagc   2880
attcggaact gcagatcacc accataccgc ttcctccccg tcgtcagctg tcgcggctgc   2940
cgcagccgtt ctttgacaag aacgtaaggc agaagacggt cattccgttc gtccttgcac   3000
agacatttga tgctgaagtg ctcaaggctt ccggcatcct ggcgtcctgg ttcggccagc   3060
agaccgattt ccgcggcgtg aacttccccg tattttccac cattccgcag acaggcaatg   3120
ccgttgtggt gggtgttgcc gatgaactgc cttccgcgct ggggcgtccg gccatcagcg   3180
ggccgaccct gatggaagtg gccaacccgt ccgatcccaa tggcacgatc ctgctggtaa   3240
cgggccggga ccgcgatgaa gtcattaccg caagcaaggg cataggcttc agctccagca   3300
cgctgccggt tgccgcgcgc atggatgtgg cgccgattga cgtggccccc cgcgccccca   3360
acgacgcgcc gtccttcatc ccgaccagcc ggcctgtccg gctgggtgaa ctggtgccgg   3420
tcagtgccct gcagggcgaa ggctataccc ccggcgtgct ttccgtggcg ttccgcacgg   3480
cgcctgacct gtatacctgg cgcgaccggc cgtacaagct gaacgtgcgc ttccgggcgc   3540
ccgacgggcc gatcgtggac ctggcgcgtt cgcatctgga cgttggtatc aacaatacct   3600
acctgcagtc ctattccctg catgaaaagg acagtgtggt cgaccagctg gtccagcgtt   3660
ttggcggccg gggccagacc agtggcgtgc agcagcatac gctgaccatt ccgccgtgga   3720
tggtgttcgg tcaggatcag ctgcagttct attttgatgc ggccccccctg acccagcccg   3780
gctgccgtcc cggccccagc ctgatccaca tgtcggttga tccggattcc acgatcgacc   3840
tgtccaacgc ctatcacatc acgcgcatgc ccaatctggc ctacatggcc agcgcggggt   3900
atccgttcac cacctatgcc gacctgtcgc actcggccgt ggtgctgccg gaccatccca   3960
atggtacggt tgtcagcgcc tatcttgacc tgatgggctt catgggggcg acgacgtggt   4020
atcccgtctc gggtctggac atcgtttccg cggatcatgt gaatgatgtg gcggaccgga   4080
acctgatcgt cctgtccacg ctggccaata gcggggaggt ttcctccctg ctgtcgaact   4140
cgtcgtacca gattgccgac gggcgcctgc acatggggat gcgctccacc ctgagtgggg   4200
tgtggaacat cttccaggac ccgatggccg ccatcaacaa tacccatccg accgaggtcg   4260
agacgaccct gagcggtggc gtgggcgcga tggtggaagc ggaatccccg ctggcatccg   4320
gacgcacggt tcttgccctg ctctcggctg acgggcaggg gctggacaat ctggtccaga   4380
tcctcgggca gcgtaagaac caggccaaga ttcagggcga cctggtgctt gcccatgggg   4440
atgacctgac atcgtaccgc agttcgcccc tttataccgt tggcacgctg ccgatgtggc   4500
tcatgccgga ctggtatatg cataaccatc ccgttcgcgt gatcgtggtg gggctgttcg   4560
gatgcctgct ggttgtggcc gtgctggttc gtgccctgtt gcggcatgca ctgttccgcc   4620
ggcggcagct gcaggaagaa aggcagaaat cgtgagcatg aacagacgct acgtcttttc   4680
```

cctttctgcc ggcctgcttg ccagcagttg catgaccgtg ctggtggcgg tgccactggc 4740
gcgcgcgcag caggcctcca cggccatgac cggtacccag gcttcgggcg ggtcggcggc 4800
gccacggcag atcctgctgc agcaggcccg gttctggctt cagcagcagc agtatgacaa 4860
tgcccgtcag gccctgcaga atgcccagcg cgtggcgccg gatgcgccgg atgtcctgga 4920
ggtacagggc gaataccaga cggcgatcgg caaccgggaa gcggcagccg atacgctgcg 4980
ccacctccag caggttgcgc ccggcagtac ggccgccaac agcctgagtg acctgttgca 5040
cgagcgttcc atctcgacat ccgacctgtc gcaggtgcgt tcccttgccg catccgggca 5100
taacgcgcag gcggtgcagg ggtaccagaa gctgttcaat ggcggtaagc cgccgcattc 5160
gcttgcggtg gaatattacc agaccatggc aggcgttccg gccgaatggg atcaggcccg 5220
ggccgggctt gccggtatcg tggcatccaa tccacaggat tatcatgccc agctcgcatt 5280
tgcgcaggcg ctgacctata atacggcgac ccgtatggaa ggtctggcgc ggctcaagga 5340
cctgcagggt ttccgcagcc aggctccggt cgaggctgcg gccgccagcc agtcctaccg 5400
gcagacgctg agctggctgc cggtaacgcc caccacgcag ccgctcatgc agcagtggct 5460
ggatagccat cccaatgata ccgaactgcg tgagcatatg gtccacccgc ccggcggccc 5520
gccggacaag gcgggtcttg cgcgtcaggc gggttatcag cagctgaatg ccggccgtat 5580
tgccgcagcc gagcagtcct tccagtccgc gttacagatc aattcccatg atgccgattc 5640
acttggcggc atgggactgg tcagcatgcg gcagggtgac gcagccgaag cccgccgcta 5700
tttccaggaa gcgatggcgg ccgatcccaa gacggcggat cgctggcgcc cggccctggc 5760
cggcatggaa atcagcggtg actatgccgc ggtccgccag cttattgccg cccaccagta 5820
tgatgcggcc aagcagcgcc tgtccgcgct ggcacgccag tccggccagt ttaccggcgc 5880
cacgctcatg ctggccgacc tgcagcgcac gaccggccag atgggtgcgg cggagcagga 5940
ataccagtcc gttctggcac gcgacccgaa cagccagctt gccctgatgg gactggcgcg 6000
ggtggagatg gcgcagggca agacggcgga agcccgccag ctgctgtcgc gtgtcggatc 6060
gcagtatgcg acccaggtcg gggaaatcga ggtgacgggc cttatggccg ccgcctcgca 6120
gacatcggat tccgcgcgca aggtctcgat cctgcgcgaa gccatggccc aggcaccgcg 6180
tgacccatgg gtgcggatca atctggccaa tgccctgcag cagcaggggg acatggcgga 6240
agccaatcgg gtcatgcagc ccatcctgtc caatcccgtg acggcgcagg accggcaggc 6300
cggtatcctg tttacctatg gcagtggcaa tgatgcgatg acacgccgcc tgctggctgg 6360
cctgtcgccc gaggactatt cccccgccat ccatgccatt gcgacggaaa tggagatcaa 6420
gcaggatctg gccagccgcc tgtccatggt ggcgaacccg gttccgctga tccgtgaagc 6480
cctttcgccg cccgacccga cgggcgcgcg tggcgtggcc gtggctgatc tgttccgtca 6540
gcgtggcgac atgattcatg cccgcatggc cctgcgcatt gcctcgaccc gcacgctcga 6600
tctttcggcg gaccagcgtc tggcctacgc caccgaatac atgaagatca gcaacccggt 6660
tgcggccgcc cgcctgctgg ccccgctggg tgacggcagt ggcacggggg cgggcaatgc 6720
cctgcttccc gagcaggtac agacgctgca gcagctgcgc atggggattg ccgtggccca 6780
gtccgacctg ctgaaccagc gcggcgatca ggcgcaggca tacgatcacc ttgctccggc 6840
cctgcaggcc gatccggaag cgacatcgcc caaactggcg ctggcgcggc tttacaatgg 6900
tcagggcaag tccggcaagg cgctggaaat cgatctggcc gtgctgcggc acaacccgca 6960
ggatctggat gcgcgccagg cagcggtgca ggctgccgtc aatagcggcc gcaagagcct 7020
ggccacccgc cttgccatgg atggtgtgca ggaaagcccg atggatgcgc gtgcctggct 7080

```
ggccatggcc gtggccgatc aggccgatgg ccatggccac cggaccatca gtgacctgcg   7140
ccgcgcctat gacctgcgtc tgcagcaggt ggaaggcacg cgggcggtgg caagcgggac   7200
gggtgagcag gaatcgcttg aaccccccgtc cagcaacccg tttcgccacc atggctatgg   7260
acgccagacg gaactgggcg caccggttac gggtggctcc tacagcatgg aggcaacgtc   7320
tcccgaagca tcggaccaga tgctgtcctc catcgccggg cagatcacca cgctgcggga   7380
aaacctggcc ccctccatcg atggcggtct ggggttccgg tcgcgttcgg gtgagcacgg   7440
catgggccgc ctgaccgaag cgaacattcc catcgtgggg cgcctgccgc tgcaggcggg   7500
tgagtccagc ctgaccttct cgatcacgcc aaccatgatc tggtcgggac agctcaatac   7560
cggttcggtc tatgatgtgc cgcgctttgg caccgacatg gcaacacagg cgtataacca   7620
gtacgtcagt tacataagcc agaacaattc cagcagcacc ctgcatagcg aacttgtcaa   7680
gggtggcgag gccgaggccg gttttgcgcc agacgtgcag ttcggcaaca gctgggtgcg   7740
ggcggacctg gggcatcgc ccatcggctt ccccatcacc aacgtactgg gcggtgtgga   7800
attctcgccg cgtgtcggac cggttacctt ccgcgtcagc gcggaacgcc gctccatcac   7860
caacagcgtg ctgtcctatg gtggcatgcg cgaccccaac tacaacacga cactgggccg   7920
ctatgcccgc cagctttatg gcaaggagct gagttcccag tggagtgagg aatggggcgg   7980
ggtcgtgacc aaccacttcc atggtcaggt tgaggcaacg ctgggcaaca ccatcgtata   8040
tggtggcggt ggctatgcca tccagaccgg caagcatgtg cagcgcaatg acgagcgcga   8100
ggcgggcatc ggtgtcaaca cgctggtctg gcacaatgcc aacatgctgg tccgcatcgg   8160
tgtcagcctg acctatttcg gctatgccaa caaccaggac ttctatacct acgggcaggg   8220
tggctacttc tcgccgcaat cctattacgc ggcgaccgta cccatccggt atgcggggca   8280
gcacaagcgg ctggactggg acgtgacggg cagcgttggc taccaggtgt tccatgaaca   8340
ctcgtcccca ttcttcccga cgtcttccct gctgcagtct ggcgcgcagt acattgctga   8400
ctcgtatgtg cagaacgcaa ccagttccga ctatctctca caggagacgg tcaacagcgc   8460
ctattatccc ggagatagta ttgctagtct tacgggtggc ttcaatgcta gggtagggta   8520
tcgatttaca cacaatcttc gtcttgatct gtcggggcgc tggcagaagg ccggtaactg   8580
gactgaaagc ggcgccatga tttccgcaca ctatcttatt atggaccagt aatgacaact   8640
ttcaacgcaa aaccggactt ttccctgttc ctgcaggccc tctcctggga gattgatgat   8700
caggccggga tcgaggtgag gaatgacctg ttgcgcgagg tcggtcacgg catggccggt   8760
cggctgcagc ctccgctgtg caacaccatt catcagctgc agatcgagct gaactcgctg   8820
ctggccatga tcaactgggg ctatgtgcag cttgaactgc tgcccgagga ccatgccatg   8880
cgcatcgtcc atgaggacct gccccaggtg ggcagcgcgg gcgagccggc cggcacatgg   8940
ctggcccccg tgctcgaagg gctgtatggc cgctggatca cgtcgcagcc gggtgccttt   9000
ggcgattatg tcgtcacccg cgatgtggat gcggaggatc tcaactccgt tcccagccag   9060
acgatcatcc tgtacatgcg cacccgcagc agcagcaact ga                      9102
```

<210> SEQ ID NO 5
<211> LENGTH: 733
<212> TYPE: DNA
<213> ORGANISM: Artificial Sequence
<220> FEATURE:
<223> OTHER INFORMATION: gfp gene

<400> SEQUENCE: 5

```
agaaggagat atacatatga gtaaaggaga agaacttttc actggagttg tcccaattct     60

tgttgaatta gatggtgatg ttaatgggca caaattctct gtcagtggag agggtgaagg    120

tgatgcaaca tacggaaaac ttacccttaa atttatttgc actactggaa agctacctgt    180

tccatggcca acacttgtca ctactttctc ttatggtgtt caatgctttt caagataccc    240

agatcatatg aaacagcatg actttttcaa gagtgccatg cccgaaggtt atgtacagga    300

aagaactata tttacaaag atgacgggaa ctacaaatca cgtgctgaag tcaagtttga    360

aggtgatacc ctcgttaata gaattgagtt aaaaggtatt gattttaaag aagatggaaa    420

cattcttgga cacaaaatgg aatacaacta taactcacac aatgtataca tcatggcaga    480

caaacaaaag aatggaatca aagttaactt caaaattaga cacaacattg aagatggaag    540

cgttcaacta gcagaccatt atcaacaaaa tactccaatt ggcgatggcc ctgtcctttt    600

accagacaac cattacctgt ccacacaatc tgccctttcc aaagatccca acgaaaagag    660

agatcacatg atccttcttg agtttgtaac agctgctggg attacacatg gcatggatga    720

actatacaaa taa                                                        733
```

<210> SEQ ID NO 6
<211> LENGTH: 2219
<212> TYPE: DNA
<213> ORGANISM: Artificial Sequence
<220> FEATURE:
<223> OTHER INFORMATION: bglAx gene

<400> SEQUENCE: 6

```
aaggaggaac aagccgcatg aaaccatccc gcaagtcatt cctgctttcc gccgtggcgt     60

gggggctggt ggccgcgctg cccgcccatg cccgccacgc ggccacggct ggtgacccgg    120

ccgatgacca ggcgcggcag gtgctcgcgc atatgagcct tcaggacaag atggcccttc    180

tgttcagtgt ggacgggggc ggcttcaatg gcagtgtcgc acctccgggg ggcttgggtt    240

cggcggcgta tctgcgtgcc ccggcgggtt cgggcctgcc ggacctgcag atatcggatg    300

cggggcttgg cgtgcgcaac cccgcgcata tccggcccaa tggtgcggcg gtttccctgc    360

catcgggtct ggccacggcc agcacatggg atgtggacat ggcccggcag gcaggtgaaa    420

tgatcgggcg cgaggcctgg ctgagcgggt tcaacatcct gctgggcggt ggtgccgacc    480

tgacgcgcga cccgcgtggc ggccgcaatt ttgaatatgc gggggaagac ccgctccaga    540

ccgggcggat ggtgggcagc accattgccg gcatccagtc gcagcatgtg atttccacgc    600

tcaagcatta cgcgatgaac gaccttgaga catcgcgcat gaccatgagt gccgatatcg    660

accccgtagc catgcgtgag agcgacctgc tgggtttcga gattgcgatt gaaaccgggc    720

atcccggttc cgtcatgtgt tcgtacaacc gggtgaatga cctgtatgcg tgtgaaaacc    780

cgtacctgct gaacacgacg ctgaagcagg actggcatta ccccggcttt gtcatgtccg    840

actggggcgc cacgcattcc tccgcccgtg cggcgctggc gggactggat caggaatcgg    900

ctggtgacca tgccgatgcg cgcccctatt tcaccgctct gttggcggcg gatgtaaagg    960

cggggcgtgt gcccgtcgcc cgtattgacg acatggcgca gcgcattgtc cgctccctgt   1020

tcgcggcggg gctggtggcc catccgccgc agcgcgggcc gctggatgtg gtgaccgaca   1080

cccttgtggc ccagcgtgat gaggaagaag gcgcggttct gctgcgcaac gaagggggta   1140

tcctgccgct ttcccccacc gcgcgcatcg cggtcattgg cgggcatgcc gatgcgggcg   1200

tgatctcggg cggggggtcc agccaggtcg atcccatcgg gggtgaggcg gtcaagggac   1260

cgggcaagaa ggaatggccg ggtgatccgg tctatttccc gtcatccccg ctcaaggcca   1320
```

tgcgggccga ggcccccaac gcgcacatca cctatgaatc cggcaccaat atcgccgccg 1380
ccgtgcgcgc cgcgcgggcg gccgatgtgg cggtcgtgta tgcaacgcag ttcaccttcg 1440
aggggatgga cgcgcccagc atgcaccttg atgccaatgc cgacgcgctg atcacagccg 1500
tggccgcggc caacccgcgt accgtggtgg tgatggaaac cggcgacccg gtgctcatgc 1560
catggaacag cagcgttgcg ggcgtgctgg aggcatggtt ccccggttcc ggcggtgggc 1620
cggccattgc acgcctgctg tttggcaagg ttgcgccctc gggccacctg accatgacct 1680
tcccgcaggc ggaaagccag ctggcccatc ccgatattgc cggtgtgacg gcggacaacg 1740
tgttcgagat gcagttcaag accgatcagg aactggtcta tgacgaaggc agcgacgtgg 1800
gctaccgctg gtttgaccgc aaccatctca agccgctcta tcccttcggt tacggtctga 1860
cctacaccac gttcagcacc gatggcctgg cggtgcacag gcatcatgat gcggtgacgg 1920
tcacctttac cgtacataat accggcaacc gccccggtgt ggatgtgccg caggtctatg 1980
tgggcctgcc cgatggcggg gcacgcaggc tggcgggctg gcagcgggtc agtctggcac 2040
cgggtgaaag ccgtgcggtg acggtacagc ttgatccgcg cctgctggcg catttgacg 2100 ggaagaagga ccgctggagc attccttcgg gcacattccg gctgtggctt ggcacgtccg 2160
ccacggatga cagccagcag gcaagcctgc acctgtccgg tcgcaccttc gcgccctga 2219

<210> SEQ ID NO 7
<211> LENGTH: 1906
<212> TYPE: DNA
<213> ORGANISM: Artificial Sequence
<220> FEATURE:
<223> OTHER INFORMATION: PhlZ quorum sensing promoter

<400> SEQUENCE: 7
ctggattcct gctcgaactc ttcgcgcctc gtttgcactc cagccccgcc gaccacacca 60
gcccgcccta caagatcttg tagtcgctaa ccctccacaa gtcctctata aaaaaccgca 120 cttccccccct cccccaagga atcccctgcc atgcacatgg aagaacacgc cctgagcgcg 180
atggacgacg aactgaaact gatgctgggc cgtttccgcc acgagcagtt cgtggagaag 240
ttggggtggc ggctgcctat ccctccgcac caagcaggct acgagtggga ccaatatgat 300
accgaacacg cccgctactt gctggccttc aacgagcacc gcagcatcgt aggttgtgcc 360
cgattgatcc ccactacctt cccgaatctg ctggaggggg tgttttccca tgcctgcgcg 420
ggggccccac ctcggcaccc tgcgatatgg gagatgactc gcttcaccac cagggagccg 480
cagttagcga tgcccctctt ctggaaaacc cttaagaccg caagcctcgc cggcgccgac 540
gcaatcgtgg gcatcgtgaa cagcacaatg gagcgttact ataaaatcaa tggcgtgaaa 600
tacgagcggc ttggcagcgt gatagaccat cagaacgaaa agattctcgc gatcaaattg 660
agcgcccatc gagaacacca ccgtggtgcg agacttccaa gcggctttac gagcgaagcc 720
cttttggagg aaaccgcgta gtaacggccg agtcgtcctc ttgggcgact cggcgcagca 780
gatgaacctt agatataacc cagcgctacc gcgtagctga cagcctgcac tcgattcgag 840
gcgccaatct tcctttggat attgcggtga tggtagttca ccgtgtctgt gcacacgccc 900
ataataacgc cgatctcctc cgaggttttt ccgtcggcgg tccaccggag cacgtcgcat 960
tcgcgctcgg agaattctac atcggtgtta aaggcgcgga cgtcggtttc cagggcggaa 1020
atcttctcca gcgcggcggc agcgaaggcc ttggtaacgg gcttcagggc ttcgaactcc 1080
tgtagcgaga tggcattgtc tttccgtgcg agagacagga cacccacgcg accttgtgtg 1140
ttaaacgacg gttgggcaag gccatggcaa aggctgctgt cattcgcctc gctccacaga 1200
tccgggcagt tcctaaagag ttcgttcgac cagaggatgg gggcggaact caccttggag 1260
tgtttaacgg tggggtcaat cagcgcatag tttgcggcct gatagcgctg cagccaatgt 1320
tctggatagt taccgtacat ataggtttta ggcctcatga aaggcgtcac cgagcacatg 1380
ccataggcaa agaagtcgaa tcgcagctcg cgcagcgccc gcaaggccac cacggtaaat 1440
tcctccatgt tcatggcctg cgcaaagatg ctgtagaaat aggcgtccca tcccaacagc 1500
tggcccagtt ccattttgaa cacctataac actccaaggg agtcgtgaga ctaaaccaac 1560
ctgagcgcct gtcaactgcc aaaatcaacg gtcatagact gcttcgcact agcgacatgt 1620
tttttatgtc taacccaact aactagccat aggccactgt ttatcagccg acgaatgagc 1680
ctgcctattc ataataatgc aacactccct ccgaccgatc gcgcccgccc tgggccacta 1740
caagatctgg tagttccaag ccccagaaac gcaggtgtat aaacgacacc gcacaaaacg 1800
atcagtgcaa aacagttcaa gcattgtcat tcgtcgcatg caattatata attatataat 1860
tgattgcgcg taatttcagt caactaagga gaacactgcc tagcta 1906

<210> SEQ ID NO 8
<211> LENGTH: 308
<212> TYPE: DNA
<213> ORGANISM: Artificial Sequence
<220> FEATURE:
<223> OTHER INFORMATION: Rox quorum sensing promoter

<400> SEQUENCE: 8
gcctcctttc gtgtttcgca gcggcctgag cgagtgccgc tgatcactga aaaaacaaaa 60
gccgggacgg taatgcgccc cggcttttgt ttgagccgat gaaaaccctg ccaagagtaa 120
aacaccggat cagcttcaac gtagcacggc acctgcaagc cgccaccctg cgacggttcg 180
ccgcaccctg ccagccagac cggtagatga agccctgaca ccgcacatgc gtcagaacgt 240
cgcacctgac agggataacc aggctcttat aatctgcctt ccaataaaaa acctgagagg 300
tcggtcat 308

<210> SEQ ID NO 9
<211> LENGTH: 1996
<212> TYPE: DNA
<213> ORGANISM: Artificial Sequence
<220> FEATURE:
<223> OTHER INFORMATION: AfmR quorum sensing promoter

<400> SEQUENCE: 9
aacagaatat agcgcgccag cgtatcgtga cttaccaact tggtgggtcg gcagctatgt 60
atccacgtgc ttaggcataa taaaaatctt gcatcgtctt cgcctatccc tgaaggtgaa 120
gtaatcctga aatataatga gttcatgaca tggattcccg actcaagtac tcggacttca 180
ttcccgcgga tgaaagcaag agtaacgtgt gcctcaaact ggagctggaa aaactgctgg 240
gcgacctgca aggcgctagc tacgcctact ttgccgcccc gcgtaaccgg gaagtggcgc 300
cgcttatcgt gtccaactac ccggcccgat ggctgaaggc gtacaagaac gcgaattatc 360
acctgatcga tcccatcatc caccacggat taaagagctg cgccccctc tcctggagcg 420 acgccttgca ggcggccccg tgtgaacgca gccgtgagct gttccggagg agcagtcaat 480
accgcatctg cacgggggcg actttcaccc tccacgacgc cgggggcatg ttcagttccc 540
tctcgctgtg taacagcggc cctcaggccg agttcgaacg ccgtatggcg gaccagcagg 600
gccacttgca gatggcgctt atccgctttc atggccgtct gctgtccctg cgcgcaatgg 660
acgaactgtt tccggaacca cagactggcc cgctgtcggc ccgcgagttg ggcgtgctca 720
agtgggtcat gatgggcaag gcgtatcggg agattgccgt catctgcgcg atttcagaac 780
gaaccgtcaa atttcacatg agcaacatca gcgggaaact gcaggtgtgc aacgccaaac 840
aggccgtata tgaggcgcaa cggcagggca tcttgtagtc aggccgagat ccgctgcggc 900
tcgcacagcg cagtttccag aggattcagc cgttgcggcc aggtatccag ccgggtcgag 960
gagagcgggc actttcgggc aatgttgctg agcaagcgtt gtcggttcgc atcggacacc 1020
ggcatgtcca gcaacagcac cttttcaccc ggggcagcct cacccacgtc cagaatttca 1080
taatgccagc ccgcgttccg cacaatacgg cccatggcgt tcgacacgac agtgatgatg 1140
ctctccagtc cgctgtgcgc agcgtggttg tgcatacaca aaagcagcat ctcggtcagg 1200
ggcagatgcg ccaggcccag ctgacgtgac cgagttttgt cgacgaagaa acggctactc 1260
tctgccatca atgcctgctt aggcggttcg cagctgaaga agccgcggaa cgggccttcg 1320
accatatacg ggtccagcgt gttgatcaac ctcagaccgg ccagcgggac gttcttccag 1380
gtgcctacga gataggtcgt acgctcatta tcgtactcgt cgaactcgat gtcgtcacga 1440
acgttcacct tccagttcaa gcggtcggca aaaacttctt tacgcaggcc gtacaggtcg 1500
gccacccacg cgtggggcgt ggggctgtag tcgagtgcat gaaactcgat ggattccata 1560
gtgttaaagt tcttccgtgg gctatggtca gtactaagga ttgggctcgc gcagtttgcg 1620
gagagtcaac ttgcgttgtg cggcgcttgt tattataaca atgtctgtcc gatgacaacc 1680
tgtacttagg tgcaggtaca ggttgtatga actgattttc atctcgcact tcgccatctg 1740
tacctagata cagttgtcct gcctgggcaa ttgcgacaac ttatgccggg cagtggttaa 1800
gccttcaatg acaccgcgaa gatgagcttt taatgttgga cgtttgttcc aactaacggg 1860
ttcatggctt gtacttgcga gtaccccact tgccttaatc gtcgaatatg ccaatgacag 1920
tctgagtgtc tggatcaggc ttcttcacgc tgcgtggcat ctccagccaa gacatcgaaa 1980
cagggaagat cagcta 1996

<210> SEQ ID NO 10
<211> LENGTH: 1080
<212> TYPE: DNA
<213> ORGANISM: Artificial Sequence
<220> FEATURE:
<223> OTHER INFORMATION: cmcAx gene

<400> SEQUENCE: 10
atgctgctgg attttatgaa gttgcagaag caggtgagcg gtatggggag gaggagtttc 60
ctttccgtca tggccgccgc tggtagcatt ccatttttga gtacggccct ggcggccgac 120
gatccggcta tcaacgcgca gtgggctatc tttagggcga aatatttcca tcccgacggt 180
cgcataattg atacggggaa ttctggcgaa agccatagtg aaggtcaagg ctacggcatg 240
ttgttcgcgg ccaccgcagg tgaccaagcg acattcgagg ccatgtggag ctggacccgg 300
gcgaacctgc agcataagac cgacgccctg ttttcgtggc gctacctaga cggccataat 360
ccgcccgtcg ccgacaaaaa caacgcgact gacggcgacc tgctgatcgc cctgggcctg 420
gttcgcgcgg gccgcctttg gaagcgcgcc gactacatcc aggatgcgat tgccatatat 480
ggcgacgttc tcaaactcat gaccctgcaa gtcgggccgt atctcgtcct ccttccgggc 540
ggggtcggct tcgctaccaa agacagcgtc acactgaacc tgagctatta tgtgatgcct 600
agcttgatgc aggccttcgc cctgaccggt gatgcgcgtt ggcaaaaggt gatgggggat 660

-continued

```
ggcctcatta ttattaacca gggccggttc ggcgaatgga agctgcctcc tgactggctg    720

tccatcaacc gtcagaacgg ccatttcagc atcgccaacg gctggccgcc gcgctttagc    780

tacgacgcta tccgcgtccc gctctacctc tattgggccc atatgctgag cccggacctc    840

ctggctgatt ttacacgctt ttggaaccac tttggagcat ccgctctgcc gggctggatc    900

gacttgacca acggtgcgcg ttctccctac aacgccccgc cggggtactt ggccgtcgcg    960

acctgcagtg gcctgtcgtc ggcagggggt ttgccgaccc tagataaagc tccagactac   1020

tactctgcgg ccttgacgct cctcgtgtac attgcgcgcg gtgagggtgg tggtatgtga   1080
```

```
<210> SEQ ID NO 11
<211> LENGTH: 933
<212> TYPE: DNA
<213> ORGANISM: Artificial Sequence
<220> FEATURE:
<223> OTHER INFORMATION: ccpAx gene

<400> SEQUENCE: 11

atggacatgg acaacccaca ggatgttact cgcatgctga gcagcggata cggcctgagt     60

ggtgaaggct tccactatca ttccttcact cgcccggtaa tgcttgacat gaccccagag    120

ctgccgcatg atagcgtgga tgatactgaa catcatttgg acgataatgt gaccgaacat    180

gagagcgcac ctgccacggc cccagttttc gtttttgatg ccgcccccgga accagcagcc    240

ccgccggtcg tggctgaggc tgccccaccg ccacctccgc cacctcctcc tgaacctgcc    300

ccgcccgaac ccccgcccgc cccaccgccg tacacaccgg ttgtgacgca tgtgcctcct    360

ccgccgccgg tggaagagac tccggtgccc gaaccagtag ccgaagcagc cgcgccagct    420

agaccgcgcc cagttccgcc ggcacagccg gcccccgaca tggcaagcac cggcggccgt    480

gaacgccggg gcttgcagcc cttcacgacc cctcgcacgc caagcgagcc gcctgtatca    540

agtcgggccg ccgcaccggc taccccgttc gtccaggccg acgattgggc gcccgtgccg    600

aaagcgcagc aacgacgcgg gcagcgcccg accggccctg ggtttttctt cgccaagggc    660

aacgatcgcg tggcaacggc tcggctgttt caaccggtgg ccgtggcacg ccctgcctcc    720

aagcccgaca gtaaggtgac tacaatgacc aagtttgaca aaaccgcgca gaacgcgccc    780

accggccgtc gccctgcccc gtcagataac tctccgacgt tgaccgaagt gttcatgaca    840

ctcggcggtc gtgcgaccga ccgcctggtg ccgaagccta gcctgcgcga tgcgttgctc    900

cggaagaggg aagaagaaac cggccaaagc taa                                933

<210> SEQ ID NO 12
<211> LENGTH: 2238
<212> TYPE: DNA
<213> ORGANISM: Artificial Sequence
<220> FEATURE:
<223> OTHER INFORMATION: bcsA  gene

<400> SEQUENCE: 12

atgagcgaag tccaatcaag tgcgcccgcc gaaagctggt tcgatcggtt gtcgaataaa     60

atcttgagct tgcggggcgc ctcgtacatc gtgggcgcca tcggcttgtg cgcgttgctc    120

gccgccacca cggtgatgct gagcgtcaac gagcagctga tcgtcgccct ggtatgcgtg    180

gtggtgttct tcatcgtggg caggcgtaag agccgtcgca cacagatctt cctggaggtc    240

ctgagcgcgc tggtgtctct gaggtatctg acttggcgcc ttaccgaaac ccttgacttc    300

gacacctggc tgcaaggcac cctgggcgtg accttgttgc tggcggaact gtacgcgctg    360

tatatgctgt tcctgtcgta cttccagacc atctctccgc tgcatcgtgc acctctgccc    420
```

ctgagcccga accccgaaga ttggccaacg gtagacatat tcatccccac ctacgacgaa 480
agcctgggga tagtccgctt gaccgtcttg ggtgcactgg gtatcgactg gccgcctgat 540
aaggtaaacg tctatatcct ggacgacggc aaacgggagg aatttgctcg ctttgccgaa 600
gaatgtgggg cgcgatacat cgctcgcccc gataacgccc acgccaaagc gggcaacctc 660
aactatgcta tccagcacac ctctggcgag tacatcctga ttctggactg cgaccacatc 720
cccacccgcg ctttcctcca aatctccatg ggtggatgg tcgaagataa aaagatcgcc 780
ctgatgcaga cgccacacca cttctactcg ccggacccgt tccagcgaaa cttggccgtg 840
gggtatagga caccaccgga gggcaacctc ttctacggcg tgatccagga cggtaacgac 900
ttctgggacg caacattttt ctgtggctcg tgcgccatct tgcgccggaa agctatcgaa 960
gaaatcaacg gcttcgccac cgaaacggtc accgaggacg cgcataccgc actgcggatg 1020
cagcgccgcg ggtggtcgac cgcgtatctg cgtatccctc tggcctcggg ccttgcaacg 1080
gagcgcttag tgacccatat tggccagcgc atgcgctggg cccgcgggat gttccaaatc 1140
ttcagagtgg acaatcctat gctgggccca ggcttgaagc tgggccaacg cctgtgttac 1200
ctctctgcca tgacgtcgtt tttctttgcc atcccacgcg ttattttcct ggcgtcgccg 1260
ctggcctttc tgttcttcag ccagaatatc attgcagcct cgccgttggc cgtcctcgcg 1320
tatgccatcc cgcacatgtt ccatagcgtg gccaccgcgg cgaaagtgaa caagggctgg 1380
agatattcgt tctggtctga agtttacgaa accgtgatgg ctctgttcct tgtccgcgtg 1440
accatcgtca caatgatgtt cccttcgaaa ggcaagttta acgtaaccga gaaaggcggc 1500
gtcctggaaa acgaagagtt tgacctaggt gccacctatc cgaacatcat cttcgccgtc 1560
atcatggcaa tcggactgat gcggggtctg ttcgcgttgg cgttccaaca tctggacatt 1620
attagcgagc gcgcctacgc gctgaactgt gtctggagcg tgatttccct catcatcctg 1680
cttgcggcca ttgcagtggg gcgggagaca aagcagatac gccacagcca ccgggttgac 1740
gcgcgcatcc cggtgaccgt gtatgattat gaagggaata gctcgcacgg catcacccag 1800
gacgtgtcga tgggcggggt tgctatccac atgccctggc gcaacgtgac acccgaccag 1860
ccggtccaaa ccgtggtaca cgccgtgttg gacggggagg ttgttaacct gccggcgacc 1920
atgattcggt gcgccaacgg taaggccgtt ttcacctgga acattacgtc cttgcctatt 1980
gaagccagcg tggtccgctt cgtgttcggc cgcgcagatg cctggttaca gtggaacgac 2040
tacgagcacg accgccccct tcgtagcctg tggagcctga tcctgtctat caaggcactg 2100
tttcgcaaga agggtcgcat gatgatccac agtcggccgc agaataaacc cattgctctg 2160
ccggtggaac gtcgtgaacc gacgtcgtcc caaggaggtc agaaacagga gggaaaaatc 2220
agccgcgcgg cctcttga 2238

<210> SEQ ID NO 13
<211> LENGTH: 2427
<212> TYPE: DNA
<213> ORGANISM: Artificial Sequence
<220> FEATURE:
<223> OTHER INFORMATION: bcsB gene

<400> SEQUENCE: 13
atgggaggaa gtatgaaaat ggtgagcctg atcgcgctgc tggtattcgc caccggtgct 60
caagcggccc cagtggcctc gaaggcgccg gcccctcaac cggccggtga taacctccct 120
ccgttgccag cagccgcccc cgcggcggca gctgctcctg ctggtcaaca gcccgctggt 180

-continued

```
gcggccagcg ccgccccagc agttgaccca gcggccgcca gtgccgccga tgctatggtg    240
gacaacgccg agaacgccac gggggtgggc tctgatgtcg ccaccgtgca tacctactcg    300
ctgcgcgaac tgggagccga aaacgcccta accatgcgcg gtgcggcccc gttgcaaggt    360
ctgcagtttg gcatcccggg cgatcagttg gtgacttccg cgcgcctggt cgtatcgggc    420
gccatgagcc ccaacttgca accggacaat tccgccgtca ccattaccct gaacgaacag    480
tatatcggaa ccttgcgccc ggacccgtcg cacccggcct tcggtccgct gtcgttcgac    540
attaacccaa tcttcttcgt gagcggcaac cggttgaatt tcaacttttc ggcaggctcc    600
aagggctgca ccgatccatc caacggcttg cagtgggcca gcgtgagtga acactccgag    660
ctccagatta ccacaatccc gttgccgccg cgccgccaac tgagccggct gccccagccc    720
ttcttcgata aaaacgtgcg ccagaaaaca gtcatcccgt ttgttctggc ccaaaccttc    780
gatgccgaag tgctgaaggc ctcgggaatc ttggccagct ggttcgggca gcaaacggat    840
ttccggggtg tgaacttccc cgtcttttca acgatccccc agaccggcaa cgccgtggta    900
gtgggcgtgg ctgatgaact gccaagcgca ctgggccgcc ctgcgatttc cggtccgacc    960
ctgatggagg tggccaaccc gagcgaccct aacggtacca tcttgctggt gacaggccgg   1020
gaccgcgacg aggtgatcac ggccagcaag ggtattggct tcagcagcag caccctgccg   1080
gtggccgcac gcatggatgt ggcccctatt gacgtggccc cgagagctcc gaacgatgca   1140
ccgagcttta tccccacgag ccgcccggtc cgtctgggcg aactggtccc ggttagtgcc   1200
ctccaaggtg aaggctacac accaggcgtc ctctcggtcg ccttccgcac ggcgccggat   1260
ctgtatacct ggcgtgaccg tccatacaaa ttgaatgtgc gcttccgtgc gccggatggc   1320
cccatcgtgg atctcgcccg ttcacacctg gacgtgggga tcaacaacac gtacctccag   1380
tcctatagtc tgcacgaaaa agactcggtg gtggaccaac tcgtgcagcg atttggcggg   1440
cgtggccaaa cctcaggtgt ccagcagcat accctgacca tccctccctg gatggtgttt   1500
ggccaggacc agctgcagtt ctacttcgat gccgcgccac taacccagcc gggctgccgc   1560
ccgggcccgt cgctcatcca catgtccgtt gacccggaca gcaccatcga cctgagtaat   1620
gcctaccaca tcacacggat gccgaatctg gcctacatgg ctagtgcggg ctaccccttc   1680
accacttacg ccgacctctc ccattccgcc gtggtcctgc cggaccaccc caatggcacc   1740
gtggtgtcgg cgtatctgga tctgatgggc tttatgggcg ccaccacgtg gtaccccgtc   1800
agcggtttgg acatcgtgtc cgcggatcat gtgaatgatg tggcagaccg gaacttgatt   1860
gtgctgagta ccctcgccaa ctcaggcgag gtcagcagct tgctgtcgaa tagttcctac   1920
cagatcgccg atggccggct ccacatgggg atgcgctcta cgttgtccgg cgtgtggaac   1980
atcttccaag acccgatggc ggccatcaat aacacccacc cgacagaagt ggaaaccacc   2040
ctgtcgggtg gtgttggcgc gatggtagag gcagaaagtc cgctcgccag cggccgcacc   2100
gtgttggcac tgctgagcgc cgatggccag ggcttggaca atttggtaca gatcctgggc   2160
caacgcaaga accaagcgaa gatccaaggc gatctggtgc tggcacatgg cgacgacctg   2220
acctcgtatc gtagtagccc gttgtacacc gtgggcaccc tgccgatgtg gctcatgccg   2280
gattggtata tgcacaacca cccggtgcgc gtgatcgtcg tcggcctctt cggctgcttg   2340
cttgtagtcg ccgtgcttgt ccgagccttg ctgcgccacg ctttattccg ccgccggcag   2400
ctccaggagg agcgacaaaa gtcgtaa                                       2427
```

<210> SEQ ID NO 14
<211> LENGTH: 3975

<212> TYPE: DNA
<213> ORGANISM: Artificial Sequence
<220> FEATURE:
<223> OTHER INFORMATION: bcsC gene

<400> SEQUENCE: 14
atgaatcgtc gctatgtgtt cagcctgtct gcgggcctgc tcgccagtag ctgcatgact 60
gtgctggtgg cggtaccgct ggcccgtgct caacaggctt cgaccgccat gactgggacc 120
caggcgagcg gcggcagcgc tgcaccgcgg caaatcctgt tgcaacaagc gcgcttctgg 180
cttcagcagc agcagtacga caacgcccgc caggcgttgc agaacgcaca acgcgtggcg 240
cccgacgccc cggacgtgct ggaggtgcag ggtgagtatc agaccgctat cggcaaccgc 300
gaggccgccg ccgacaccct ccgtcacctg cagcaggtcg ccccgggttc caccgccgcc 360
aacagcttga gcgacctcct gcatgaacgc tccatcagca ccagtgacct gagccaggtc 420
cgcagcctgg ccgcctcggg gcataacgcc caagccgtcc agggctacca gaagttgttt 480
aacgggggta aaccgcccca cagcctcgcg gtggaatatt accaaaccat ggccggcgtc 540
ccggcggagt gggatcaggc gcgggcgggc ctggctggta tcgtggccag caacccccaa 600
gattaccacg cccagttggc cttcgcgcag gcgctgacct acaacaccgc cacccgtatg 660
gaaggtctgg cccgactgaa ggacttgcag ggctttcgtt cgcaggcgcc cgtggaagcc 720
gctgcagcta gccagagtta ccgtcagacc ctgagctggc tgccggtcac ccccactacc 780
cagccgttga tgcagcagtg gctggattcc catccgaatg acactgaact tcgcgagcac 840
atggttcacc ctccgggcgg tcccccggac aaagcaggtc tggcccgcca ggccggctac 900
cagcagctga acgcgggccg gattgccgcc gctgagcagt ccttccagtc ggcgctgcaa 960
atcaacagcc acgacgccga ctccttgggt ggcatgggcc tggtgtcgat gcgccaaggc 1020
gacgcagcag aggcccggcg ttacttccag gaagctatgg ccgccgaccc caaaaccgcc 1080
gatcgttggc gccctgccct ggcagggatg gagatcagcg gtgactacgc tgccgttcgc 1140
cagttgatcg cagctcacca gtacgatgcc gccaagcaaa ggctgtcggc gctggcacgt 1200
cagtccggcc aattcaccgg ggcgacgctc atgctcgccg acctgcagcg gaccaccggt 1260
cagatgggcg ccgcagaaca ggagtaccag agcgtactgg cccgggaccc taactcacaa 1320
cttgcgctca tgggcttggc ccgcgttgaa atggcgcagg gtaagacagc cgaagcccgt 1380
caattgctct cccgcgtcgg tagccagtat gctacacaag tcggcgagat cgaagttaca 1440
ggtttgatgg ccgccgccag ccaaacaagc gactcggcgc gtaaagtaag cattttgcgc 1500
gaagctatgg cccaggctcc ccgtgatcct tgggtgcgta tcaatttggc gaatgccctt 1560
cagcaacaag gtgacatggc ggaagcaaac cgcgtgatgc agcctatcct gagcaaccca 1620
gtcaccgctc aagatcgcca agcgggcatc ctgttcacat acggtagtgg caacgacgcg 1680
atgacccgcc gcctgttggc tgggctgtcc ccagaggatt atagtccagc aattcacgcc 1740
atagctaccg agatggagat caaacaagat ctggccagtc gcctgagcat ggtggctaac 1800
ccagtcccat tgattcgaga ggccctgagt cctccggacc ccaccggtgc ccgtggagtc 1860
gcggtggcgg acctgtttcg ccagcgtggt gacatgatcc atgcccgaat ggctttacgc 1920
attgctagca cgagaacctt ggacttgagc gctgaccaac gcctggccta cgcgaccgaa 1980
tacatgaaga tctccaatcc ggtcgccgca gcgaggttat tggccccgct cggggatggt 2040
agtggaaccg gcgctggcaa cgcactgttg ccggaacagg ttcaaaccct tcaacaactt 2100
cggatgggga ttgccgtcgc acagtccgat ttgcttaatc agcgtgggga ccaagctcag 2160
gcctacgacc atttggcccc ggctttgcag gccgaccccg aagcgacctc accgaaatta 2220
gcgctggctc gactctataa tggtcagggg aaatcaggga aagctctgga aatcgacttg 2280
gcggtgctcc gtcacaaccc ccaagacttg gacgccagac aagcggcggt gcaagccgcc 2340
gtcaactccg gccgaaagag tctggcgacg cggctggcta tggacggggt gcaagagagc 2400
cccatggatg cccgcgcatg gttggccatg gccgtggccg atcaagccga tggacacggc 2460
catcgtacta tcagtgatct ccggcgcgcg tacgatttgc gattgcaaca ggttgagggc 2520
acccgtgcag tggcatccgg taccggtgaa caggaaagcc tggaaccccc tagctcgaac 2580
ccgttccgcc atcacgggta cggccggcag actgagttgg gcgcgcccgt gacaggcggt 2640
tcgtactcga tggaagcgac ctcccctgag gcgagtgatc aaatgctgtc cagcatcgcc 2700
ggccagatca ccaccctgag agagaacctg gcaccctcca tagacggagg cctggggttc 2760
cgttcgcgta gcggcgaaca cggcatgggc cggctgaccg aggcgaacat cccgatcgtc 2820
gggaggctcc cgctgcaggc cggcgaatcc tccctcacct tctccatcac cccgaccatg 2880
atctggtcag gccaactgaa tactggcagc gtttatgacg ttccgcgctt tggcaccgac 2940
atggccaccc aggcatacaa ccagtacgtc agctacatca gccagaataa cagcagcagt 3000
accctgcact cggagttggt taagggcggg gaagccgaag cgggcttcgc cccggacgtc 3060
cagttcggca attcgtgggt gcgtgccgac ttgggggcaa gcccgatagg ctttcctatc 3120
acgaacgtac tgggcggtgt ggagttcagc ccccgcgtgg gacccgtgac gttccgtgtc 3180
agtgcagaac gccgttcgat caccaactct gtcctttcgt acggcggcat gcgcgacccg 3240
aactacaaca ccacgctggg tcgatatgcc cgccagctgt acggcaaaga actgagctcc 3300
cagtggagtg aagagtgggg cggcgttgtc accaaccatt ttcatggcca agtggaggcc 3360
actctgggga acaccatcgt gtacggtggc gggggctacg cgattcaaac cggtaagcac 3420
gtccagcgaa atgacgaacg tgaggccggt atcggcgtca acactttggt gtggcacaac 3480
gccaacatgc tggtccggat aggcgtcagc ctgacctact tcggctatgc gaacaatcaa 3540
gatttttaca cctacggtca aggcggctac ttctcaccgc aatcctacta cgccgctact 3600
gtgccgatcc gctatgccgg ccagcacaag cgcctggact gggatgtcac cggctccgtg 3660
ggttaccaag ttttccacga acactctagt ccgttcttcc cgacatcgtc gctgctgcaa 3720
tccggcgccc aatacatcgc ggacagctac gtccaaaacg caacctcgtc tgactacctc 3780
agtcaggaaa ccgtcaactc cgcctactac ccgggcgaca gcatcgcctc gttgaccggt 3840
ggatttaatg cacgcgtcgg ctaccgcttc acgcacaatc tgcgtctgga cctgagcggt 3900
cggtggcaaa aggccgggaa ctggaccgaa agcggtgcga tgatctccgc ccattacctg 3960
atcatggatc agtaa 3975

<210> SEQ ID NO 15
<211> LENGTH: 475
<212> TYPE: DNA
<213> ORGANISM: Artificial Sequence
<220> FEATURE:
<223> OTHER INFORMATION: bcsD gene

<400> SEQUENCE: 15
atgaccacct tcaatgcaaa acccgacttc tccctgtttc tgcaggccct gagctgggaa 60
atcgatgacc aggccggtat cgaggtccgt aacgatctgc tgcgagaagt ggggcacggc 120
atggcgggtc gcttgcaacc tccgctctgc aacaccattc atcaactcca gatcgaactg 180
aattccctgt tggccatgat caactggggc tatgtgcaac tggaactgct gccagaagat 240
catgctatgc gtattgtaca cgaggatctg ccccaggttg gctccgccgg cgaaccagcg 300
ggcacctggt tggcccctgt cctggaaggt ctgtacggcc gctggatcac ctcgcagccg 360
ggtgcctttg gcgattatgt ggtcacccgc gacgtcgatg ccgaggacct caatagcgtg 420
ccgtcccaaa ccatcatact gtacatgcgg acccggtcgt cgtctaacta gatca 475

<210> SEQ ID NO 16
<211> LENGTH: 732
<212> TYPE: DNA
<213> ORGANISM: Artificial Sequence
<220> FEATURE:
<223> OTHER INFORMATION: gfp gene

<400> SEQUENCE: 16
atgggggagg ttcggatgtc caaaggcgag gaactgttca ctggtgtggt ccccatcttg 60
gtggaattgg atggtgatgt taacggccat aagttctcgg tgtcgggtga aggcgagggc 120
gacgctacct atggtaaact gactttgaag tttatctgca ccaccggcaa actgcccgtg 180
ccttggccga cgctggtgac gaccttcagc tatggagtcc agtgcttctc gcgctacccc 240
gaccacatga aacagcacga tttcttcaag tccgcgatgc cggaggggta tgttcaggag 300
cgtactatct tttacaaaga cgatgggaat tacaagagcc gcgccgaagt gaaattcgaa 360
ggcgatacct tggtcaatcg catcgagctg aagggcattg acttcaagga agatggcaac 420
atcctgggtc ataaaatgga atacaactac aacagccaca acgtgtatat catggccgat 480
aaacagaaaa atggcataaa ggtcaacttc aaaatccgtc ataacatcga ggatggcagc 540
gtccagttgg ccgaccacta ccagcagaac actccaattg gcgacggccc cgtcctgttg 600
ccggacaacc actacttgtc aacccagagc gcgctgtcga aagaccccaa tgagaagcgg 660
gatcatatga tccttctgga gttcgtgacg gccgcgggta tcacccatgg catggacgag 720
ctgtacaagt aa 732

<210> SEQ ID NO 17
<211> LENGTH: 2202
<212> TYPE: DNA
<213> ORGANISM: Artificial Sequence
<220> FEATURE:
<223> OTHER INFORMATION: bglAx gene

<400> SEQUENCE: 17
atgaaaccga gccgcaaaag ctttctgctc agtgccgtgg catggggcct cgtcgctgcc 60
ctgccggcac acgcccgtca cgctgccacc gctggcgacc cggcggacga tcaggcccgt 120
caagttctgg cccatatgtc cctccaagac aagatggccc tgctgttttc tgttgacggc 180
gggggcttta acggcagcgt cgccccgcct ggcggtcttg gcagcgccgc ctatctccgt 240
gctcctgctg gtagcggcct tccggatctg cagatatccg acgcgggtct gggcgttcgc 300
aaccccgccc acatccgtcc aaatggggcc gctgtgagcc tgccgtccgg cctcgccacc 360
gccagtactt gggatgtcga tatggcacgt caggcaggcg aaatgatcgg gcgcgaagct 420
tggttgagtg gctttaacat cctgctgggt gggggcgccg acctgacacg cgatccccgc 480
ggcgggcgca acttcgagta cgcgggtgaa gatccgctgc agacgggtcg catggtcggt 540
agcaccatcg cgggaatcca gtcccagcac gtcatcagca ccttgaaaca ctacgcaatg 600
aacgatctgg aaacgtcacg gatgacgatg tccgccgaca tcgatccggt tgcaatgcgc 660
gaaagcgacc tgctcggctt cgaaatcgct atcgaaaccg gccatcctgg ctcggtgatg 720
tgcagctaca atcgcgtgaa cgacctgtac gcgtgcgaga acccgtacct gctgaacacc 780
accctgaaac aagattggca ttacccgggc tttgtgatgt cggactgggg tgccacccat 840
tccagtgccc gcgcggcgtt ggccggtctg gaccaggagt ccgcgggcga ccatgccgac 900
gcacgtccgt acttcaccgc cttgctggcg gccgacgtga aagccggccg cgtacccgtg 960
gcccgcattg atgacatggc ccagcgcatc gtccgcagcc tgttcgcggc tggcctggta 1020
gcacatccgc cgcagcgcgg tcctctggat gtcgtgaccg atacactggt ggctcaacgt 1080
gatgaagagg aaggcgccgt gctgctgcgc aacgaaggcg gcatcctgcc cctgagcccg 1140
accgctcgta tcgccgtcat cggcggccat gccgatgcgg gcgtaatctc gggtgggggt 1200
agtagtcagg tggacccgat tggcggggag gcggttaagg gcccgggtaa aaaggagtgg 1260
ccaggggacc cggtgtattt ccctagctcg ccgctgaaag caatgcgtgc ggaggcgccg 1320
aacgcacata ttacctacga gagcgggacc aatatcgcag ccgccgtgcg cgccgcccgg 1380
gccgccgatg ttgccgttgt ttacgcgacc cagttcacct tcgaggggat ggatgcccct 1440
agtatgcacc tcgacgctaa cgcggatgca ctgatcaccg ccgttgctgc cgcgaaccca 1500
cgaaccgtcg ttgtgatgga aacaggcgac ccggtgctga tgccgtggaa tagctccgtc 1560
gcaggtgtct tggaagcatg gttccctggc tcgggcggcg ggcccgccat cgcccgcctg 1620
ctgtttggca aggtcgcgcc cagcgggcat ctgacgatga cttttccgca ggccgaatcc 1680
caacttgcgc acccagatat agccggcgtg acggctgaca atgtgttcga gatgcagttc 1740
aagaccgatc aggagctggt gtacgatgaa ggcagtgacg tggggtatcg ctggtttgac 1800
cgtaaccacc tgaagccgct gtaccctttc ggctacggtc tgacctacac caccttctcc 1860
accgacggcc ttgcggtgca tcgccaccac gatgcggtca ccgtgacctt caccgtgcac 1920
aacaccggca accgtccagg cgtggatgtc ccgcaagtat acgtggggct gccggacggc 1980
ggtgcacggc gcttagctgg ctggcagcgg gtgtcattgg ctccgggcga gagtcgcgct 2040
gtaaccgtcc agttggaccc gcgcttgttg gcccacttcg acggcaagaa agatcgctgg 2100
tccatcccgt ccggtacctt tcgtctgtgg ctggggacct cggccactga cgattcgcag 2160
caggccagtc tgcacttgtc aggccggacc ttcgccccgt ga 2202

<210> SEQ ID NO 18
<211> LENGTH: 14542
<212> TYPE: DNA
<213> ORGANISM: Artificial Sequence
<220> FEATURE:
<223> OTHER INFORMATION: modified microorganism

<400> SEQUENCE: 18
aaaccaattg tccatattgc atcagacatt gccgtcactg cgtcttttac tggctcttct 60
cgctaaccaa accggtaacc ccgcttatta aaagcattct gtaacaaagc gggaccaaag 120
ccatgacaaa aacgcgtaac aaaagtgtct ataatcacgg cagaaaagtc cacattgatt 180
atttgcacgg cgtcacactt tgctatgcca tagcattttt atccataaga ttagcggatc 240
ctacctgacg ctttttatcg caactctcta ctgtttctcc atacccgttt tttgggctaa 300
caggaggaat taaccatgct gttggatttt atgaagctgc aaaaacaggt atccggaatg 360
ggacgtcgtt ctttcctgtc tgtcatggcg gcagctggca gtattccttt cctttctacc 420
gccctggccg cggatgaccc ggccataaac gcgcaatggg ccatcttccg cgccaagtat 480
ttccaccccg acggccgtat catcgacaca ggcaacagtg gcgaatccca tagcgagggg 540
cagggctacg gcatgctttt cgccgcgacg gcgggtgatc aggccacgtt cgaggccatg 600
tggtcctgga cacgcgccaa cctgcagcac aagaccgatg ccctgttctc ctggcgctat 660
ctggacgggc ataacccgcc ggtcgcggac aagaacaacg cgacggatgg cgacctgctg 720
atagccctgg gtctggtccg tgccggacgg ctgtggaagc gcgctgacta tattcaggat 780
gctatagcca tctatggcga cgtgctgaag ctcatgaccc tgcaggtcgg tccctatctg 840
gtgcttctgc ccggcggcgt ggggtttgcc accaaggatt cggtcacgct caacctgtcc 900
tattatgtca tgccctcgct catgcaggcc ttcgcgctga cgggcgacgc acgctggcag 960
aaggtgatgg gagatggtct gatcatcata aaccaggggc gattcgggga gtggaagctc 1020
ccgcctgact ggctttcgat caaccgccag aacgggcatt tctccatagc caatggctgg 1080
ccgccgcgat tctcctatga tgcgattcgc gtgccgctgt atctttactg ggcgcatatg 1140
ctgtcgccgg acctgctggc cgactttacc cgcttctgga accatttcgg ggcatcggcc 1200
ctgccggggt ggattgacct gaccaatggt gcccgctcgc cctacaatgc gccaccgggc 1260
tatctggccg tggcgacatg ttccggcctg tcatccgccg gtgggttgcc aaccctggac 1320
aaggcgccgg attattattc ggctgccctg acattgctgg tttatattgc ccgtggtgag 1380
ggaggtggaa tgtgagcatg gatatggaca atccgcagga cgtgacgcgc atgctctcca 1440
gcggttatgg cctgagcggg gaggggttcc actaccattc cttcacgcgt cccgtcatgc 1500
tggacatgac cccggaactg ccccacgatt ccgtggacga tacagagcat catctcgacg 1560
ataacgtcac cgaacacgaa tccgccccgg caacggcacc ggtgttcgtg ttcgatgcgg 1620
cacctgagcc tgcggcacca cctgttgttg ccgaggccgc gccaccgcca cctcctccgc 1680
cgccgccaga gcctgcgcct cctgagccgc cgcccgcacc gccaccctat acgccggttg 1740
taacccacgt gccgccgccg ccgcccgtgg aggaaacgcc ggtacccgaa cccgtggctg 1800
aagcggctgc acctgcaagg ccccggcccg tgccgccggc gcagcccgcg ccggacatgg 1860
catcgacggg cgggcgtgaa cggcgcgggc ttcagccttt taccacgccg cgtacgccat 1920
ccgagccgcc ggtgtcttca cgtgcggccg caccggccac gcccttcgtc caggcagatg 1980
actgggcgcc ggtgccaaag gcccagcagc gtcgcggcca gcgtccgacc gggcctggtt 2040
tcttctttgc caaggggaat gaccgggttg cgactgcccg gctgttccag ccggtggcag 2100
tggcccgtcc tgcttccaaa cctgactcca aggtgaccac gatgaccaaa ttcgacaaga 2160
ccgcacagaa tgcccccacg gggcgtcgtc ctgcgccatc tgacaattcg ccaacactga 2220
cggaagtttt catgacactg ggcggtcgtg ccaccgaccg gctggtgccc aagcccagcc 2280
tgcgtgacgc gctgctgcgc aagcgtgagg aagaaaccgg gcaatcctga aatgtcagag 2340
gttcagtcgt cagcgcccgc ggaaagttgg tttgatcgcc tttccaacaa gatactgtca 2400
ctgcgcggtg ccagttatat cgttggggca ataggcctgt gcgccctgct tgccgcgacc 2460
acggttatgc tgtcggtaaa tgaacagctg attgtggcat tagtgtgcgt tgtggtcttt 2520
tttatcgtcg gtcggcgcaa aagccgtcgg acgcagatat ttctcgaggt gctttcggcg 2580
ctggtgtccc tgcgttatct gacgtggcgg ctgaccgaaa cactggattt cgatacatgg 2640
ctccagggta cattgggggt cacgctgctt ctggcggaac tgtacgcgct gtacatgctg 2700
ttcctcagct atttccagac catttccccc ctgcaccgcg cgccgctgcc cctgtctccc 2760
aatccggaag actggcccac ggtcgacatc ttcatcccga cctatgacga aagcctgggc 2820
atcgtgcgtc tgacggtgct gggcgcgctt ggtatcgact ggccaccgga caaggtgaac 2880
gtctatatcc ttgatgacgg caagcgtgag gaattcgccc gctttgccga agaatgcggt 2940
gcccgctaca ttgcccgtcc cgataacgcg catgccaagg ccggtaacct gaactacgcc 3000
attcagcata caagtggcga atacatcctg attctggact gcgatcacat cccgacccgt 3060
gcgttcctgc agatctcgat gggatggatg gtcgaggaca agaagatcgc cctgatgcag 3120
acgccgcatc acttctattc ccccgatcct ttccagcgta acctggccgt cggttaccgc 3180
acgccgcctg aaggcaacct gttctatggt gtcattcagg atggcaacga cttctgggat 3240
gcgaccttct tctgtggttc ctgtgccatc ctgcgccgca aggccatcga agagatcaat 3300
ggtttcgcaa ccgagaccgt gacggaagat gcccataccg ccctgcgcat gcagcgcagg 3360
gggtggtcga ccgcctatct gcgcattccg ctggccagcg ggctggcgac ggagcgcctg 3420
gtcacgcata tcgggcagcg tatgcgctgg gcccgtggca tgttccagat cttccgcgtg 3480
gataatccca tgctggggcc gggcctgaag ctggggcagc ggctttgcta tctttcggcc 3540
atgacgtcgt tcttcttcgc cattccgcgt gtcatcttcc ttgcctcccc gctggccttc 3600
cttttcttca gccagaatat catcgcggcc tccccccctgg cggtgctggc ctacgccatt 3660
ccccacatgt tccattccgt tgccacggcg gcaaaggtga acaagggatg gcgctattca 3720
ttctggagtg aagtgtacga aaccgtcatg gcgctgttcc tggtgcgggt gaccatcgtc 3780
acgatgatgt tcccctcgaa gggcaagttc aacgtgacgg aaaaaggtgg cgttctggag 3840
aacgaggaat tcgaccttgg tgccacatat ccgaacatca tctttgcggt catcatggcg 3900
attggcctga tgcgcgggct gtttgccctg gccttccagc atctggacat aatttcagag 3960
cgtgcctacg cactcaactg tgtctggtcc gtgatcagtc tcatcatcct gcttgcggcc 4020
attgccgtcg gccgtgagac caagcagatc cgccacagcc atcgtgtcga tgcgcgaatt 4080
ccggtaacgg tttatgatta cgaagggaat tccagccatg gcatcacgca ggacgtgtcc 4140
atgggtggtg tggccattca tatgccgtgg cgcaatgtga caccggacca gccggtgcag 4200
accgttgtcc acgccgtgct ggatggtgag gtggtcaatc tccccgctac catgatccgc 4260
tgtgcgaatg gcaaggcggt ctttacctgg aacatcacct ccctcccgat tgaagcctct 4320
gtcgtccggt tcgtgttcgg tcgcgccgat gcctggctgc agtggaatga ttacgagcat 4380
gatcggccgt tgcgaagcct gtggagcctg atcctcagca tcaaggcgct gttccgcaag 4440
aagggtcgga tgatgatcca tagtcgcccg caaaataaac ccattgcact gcctgttgag 4500
cgcagggagc caacaagcag tcagggtggt cagaaacagg aaggaaagat cagtcgtgcg 4560
gcctcgtgat atgaaaatgg tgtccctgat cgcgctgctg gtctttgcaa cgggagcgca 4620
ggctgcgccg gttgcatcca aagcgccagc cccgcagcct gcgggcgata acctgccgcc 4680
cctgcccgcc gcggcaccgg ccgccgcggc agccccggcc gggcagcagc ctgctggcgc 4740
cgccagtgcg gcacctgccg tcgatccggc cgctgccagc gccgccgatg ccatggtgga 4800
caatgcggag aatgcgaccg gcgtcggttc ggatgtggcg accgtgcata cctattccct 4860
gcgcgaactt ggcgcggaga acgcgctgac catgcgtggc gcggcccccc tgcaggggct 4920
gcagttcggt attccgggcg accagctcgt cacctcggcg cggcttgtcg tgtcgggtgc 4980
gatgtcaccc aatctccagc ccgataacag cgcggtcacg attacgctga acgagcagta 5040
tatcggcacg ctccggcctg acccgtcaca tccggccttt ggtccgcttt cctttgacat 5100
caaccccatc ttctttgtca gcggcaaccg gctgaacttc aatttctcgg cagggtcgaa 5160
aggatgcacc gacccgagca acggattgca gtgggccagc gtgtccgagc attcggaact 5220
gcagatcacc accataccgc ttcctccccg tcgtcagctg tcgcggctgc cgcagccgtt 5280
ctttgacaag aacgtaaggc agaagacggt cattccgttc gtccttgcac agacatttga 5340

```
tgctgaagtg ctcaaggctt ccggcatcct ggcgtcctgg ttcggccagc agaccgattt   5400
ccgcggcgtg aacttccccg tattttccac cattccgcag acaggcaatg ccgttgtggt   5460
gggtgttgcc gatgaactgc cttccgcgct ggggcgtccg gccatcagcg ggccgaccct   5520
gatggaagtg gccaacccgt ccgatcccaa tggcacgatc ctgctggtaa cgggccggga   5580
ccgcgatgaa gtcattaccg caagcaaggg cataggcttc agctccagca cgctgccggt   5640
tgccgcgcgc atggatgtgg cgccgattga cgtggccccc cgcgcccccca acgacgcgcc   5700
gtccttcatc ccgaccagcc ggcctgtccg gctgggtgaa ctggtgccgg tcagtgccct   5760
gcagggcgaa ggctataccc ccggcgtgct ttccgtggcg ttccgcacgg cgcctgacct   5820
gtatacctgg cgcgaccggc cgtacaagct gaacgtgcgc ttccgggcgc ccgacgggcc   5880
gatcgtggac ctggcgcgtt cgcatctgga cgttggtatc aacaatacct acctgcagtc   5940
ctattccctg catgaaaagg acagtgtggt cgaccagctg gtccagcgtt ttggcggccg   6000
gggccagacc agtggcgtgc agcagcatac gctgaccatt ccgccgtgga tggtgttcgg   6060
tcaggatcag ctgcagttct attttgatgc ggccccccctg acccagcccg gctgccgtcc   6120
cggccccagc ctgatccaca tgtcggttga tccggattcc acgatcgacc tgtccaacgc   6180
ctatcacatc acgcgcatgc ccaatctggc ctacatggcc agcgcggggt atccgttcac   6240
cacctatgcc gacctgtcgc actcggccgt ggtgctgccg gaccatccca atggtacggt   6300
tgtcagcgcc tatcttgacc tgatgggctt catgggggcg acgacgtggt atcccgtctc   6360
gggtctggac atcgtttccg cggatcatgt gaatgatgtg gcggaccgga acctgatcgt   6420
cctgtccacg ctggccaata gcggggaggt ttcctccctg ctgtcgaact cgtcgtacca   6480
gattgccgac gggcgcctgc acatggggat gcgctccacc ctgagtgggg tgtggaacat   6540
cttccaggac ccgatggccg ccatcaacaa tacccatccg accgaggtcg agacgaccct   6600
gagcggtggc gtgggcgcga tggtggaagc ggaatccccg ctggcatccg gacgcacggt   6660
tcttgccctg ctctcggctg acgggcaggg gctggacaat ctggtccaga tcctcgggca   6720
gcgtaagaac caggccaaga ttcagggcga cctggtgctt gcccatgggg atgacctgac   6780
atcgtaccgc agttcgcccc tttataccgt tggcacgctg ccgatgtggc tcatgccgga   6840
ctggtatatg cataaccatc ccgttcgcgt gatcgtggtg gggctgttcg gatgcctgct   6900
ggttgtggcc gtgctggttc gtgccctgtt gcggcatgca ctgttccgcc ggcggcagct   6960
gcaggaagaa aggcagaaat cgtgagcatg aacagacgct acgtcttttc cctttctgcc   7020
ggcctgcttg ccagcagttg catgaccgtg ctggtggcgg tgccactggc gcgcgcgcag   7080
caggcctcca cggccatgac cggtacccag gcttcgggcg ggtcggcggc gccacggcag   7140
atcctgctgc agcaggcccg gttctggctt cagcagcagc agtatgacaa tgcccgtcag   7200
gccctgcaga atgcccagcg cgtggcgccg gatgcgccgg atgtcctgga ggtacagggc   7260
gaataccaga cggcgatcgg caaccgggaa gcggcagccg atacgctgcg ccacctccag   7320
caggttgcgc ccggcagtac ggccgccaac agcctgagtg acctgttgca cgagcgttcc   7380
atctcgacat ccgacctgtc gcaggtgcgt tcccttgccg catccgggca taacgcgcag   7440
gcggtgcagg ggtaccagaa gctgttcaat ggcggtaagc cgccgcattc gcttgcggtg   7500
gaatattacc agaccatggc aggcgttccg gccgaatggg atcaggcccg ggccgggctt   7560
gccggtatcg tggcatccaa tccacaggat tatcatgccc agctcgcatt tgcgcaggcg   7620
ctgacctata atacggcgac ccgtatggaa ggtctggcgc ggctcaagga cctgcagggt   7680
```

ttccgcagcc aggctccggt cgaggctgcg gccgccagcc agtcctaccg gcagacgctg 7740
agctggctgc cggtaacgcc caccacgcag ccgctcatgc agcagtggct ggatagccat 7800
cccaatgata ccgaactgcg tgagcatatg gtccacccgc ccggcggccc gccggacaag 7860
gcgggtcttg cgcgtcaggc gggttatcag cagctgaatg ccggccgtat tgccgcagcc 7920
gagcagtcct tccagtccgc gttacagatc aattcccatg atgccgattc acttggcggc 7980
atgggactgg tcagcatgcg gcagggtgac gcagccgaag cccgccgcta tttccaggaa 8040
gcgatggcgg ccgatcccaa gacggcggat cgctggcgcc cggccctggc cggcatggaa 8100
atcagcggtg actatgccgc ggtccgccag cttattgccg cccaccagta tgatgcggcc 8160
aagcagcgcc tgtccgcgct ggcacgccag tccggccagt ttaccggcgc cacgctcatg 8220
ctggccgacc tgcagcgcac gaccggccag atgggtgcgg cggagcagga ataccagtcc 8280
gttctggcac gcgacccgaa cagccagctt gccctgatgg gactggcgcg ggtggagatg 8340
gcgcagggca agacggcgga agcccgccag ctgctgtcgc gtgtcggatc gcagtatgcg 8400
acccaggtcg ggaaatcga ggtgacgggc cttatggccg ccgcctcgca gacatcggat 8460
tccgcgcgca aggtctcgat cctgcgcgaa gccatggccc aggcaccgcg tgacccatgg 8520
gtgcggatca atctggccaa tgccctgcag cagcaggggg acatggcgga agccaatcgg 8580
gtcatgcagc ccatcctgtc caatcccgtg acggcgcagg accggcaggc cggtatcctg 8640
tttacctatg gcagtggcaa tgatgcgatg acacgccgcc tgctggctgg cctgtcgccc 8700
gaggactatt cccccgccat ccatgccatt gcgacggaaa tggagatcaa gcaggatctg 8760
gccagccgcc tgtccatggt ggcgaacccg gttccgctga tccgtgaagc cctttcgccg 8820
cccgacccga cgggcgcgcg tggcgtggcc gtggctgatc tgttccgtca gcgtggcgac 8880
atgattcatg cccgcatggc cctgcgcatt gcctcgaccc gcacgctcga tctttcggcg 8940
gaccagcgtc tggcctacgc caccgaatac atgaagatca gcaacccggt tgcggccgcc 9000
cgcctgctgg ccccgctggg tgacggcagt ggcacggggg cgggcaatgc cctgcttccc 9060
gagcaggtac agacgctgca gcagctgcgc atggggattg ccgtggccca gtccgacctg 9120
ctgaaccagc gcggcgatca ggcgcaggca tacgatcacc ttgctccggc cctgcaggcc 9180
gatccggaag cgacatcgcc caaactggcg ctggcgcggc tttacaatgg tcagggcaag 9240
tccggcaagg cgctggaaat cgatctggcc gtgctgcggc acaacccgca ggatctggat 9300
gcgcgccagg cagcggtgca ggctgccgtc aatagcggcc gcaagagcct ggccacccgc 9360
cttgccatgg atggtgtgca ggaaagcccg atggatgcgc gtgcctggct ggccatggcc 9420
gtggccgatc aggccgatgg ccatggccac cggaccatca gtgacctgcg ccgcgcctat 9480
gacctgcgtc tgcagcaggt ggaaggcacg cgggcggtgg caagcgggac gggtgagcag 9540
gaatcgcttg aacccccgtc cagcaacccg tttcgccacc atggctatgg acgccagacg 9600
gaactgggcg caccggttac gggtggctcc tacagcatgg aggcaacgtc tcccgaagca 9660
tcggaccaga tgctgtcctc catcgccggg cagatcacca cgctgcggga aaacctggcc 9720
ccctccatcg atggcggtct ggggttccgg tcgcgttcgg gtgagcacgg catgggccgc 9780
ctgaccgaag cgaacattcc catcgtgggg cgcctgccgc tgcaggcggg tgagtccagc 9840
ctgaccttct cgatcacgcc aaccatgatc tggtcgggac agctcaatac cggttcggtc 9900
tatgatgtgc cgcgctttgg caccgacatg gcaacacagg cgtataacca gtacgtcagt 9960
tacataagcc agaacaattc cagcagcacc ctgcatagcg aacttgtcaa gggtggcgag 10020
gccgaggccg gttttgcgcc agacgtgcag ttcggcaaca gctgggtgcg ggcggacctg 10080

```
ggggcatcgc ccatcggctt ccccatcacc aacgtactgg gcggtgtgga attctcgccg  10140
cgtgtcggac cggttacctt ccgcgtcagc gcggaacgcc gctccatcac caacagcgtg  10200
ctgtcctatg gtggcatgcg cgaccccaac tacaacacga cactgggccg ctatgcccgc  10260
cagctttatg gcaaggagct gagttcccag tggagtgagg aatggggcgg ggtcgtgacc  10320
aaccacttcc atggtcaggt tgaggcaacg ctgggcaaca ccatcgtata tggtggcggt  10380
ggctatgcca tccagaccgg caagcatgtg cagcgcaatg acgagcgcga ggcgggcatc  10440
ggtgtcaaca cgctggtctg gcacaatgcc aacatgctgg tccgcatcgg tgtcagcctg  10500
acctatttcg gctatgccaa caaccaggac ttctatacct acgggcaggg tggctacttc  10560
tcgccgcaat cctattacgc ggcgaccgta cccatccggt atgcggggca gcacaagcgg  10620
ctggactggg acgtgacggg cagcgttggc taccaggtgt tccatgaaca ctcgtcccca  10680
ttcttcccga cgtcttccct gctgcagtct ggcgcgcagt acattgctga ctcgtatgtg  10740
cagaacgcaa ccagttccga ctatctctca caggagacgg tcaacagcgc ctattatccc  10800
ggagatagta ttgctagtct tacgggtggc ttcaatgcta gggtagggta tcgatttaca  10860
cacaatcttc gtcttgatct gtcggggcgc tggcagaagg ccggtaactg gactgaaagc  10920
ggcgccatga tttccgcaca ctatcttatt atggaccagt aatgacaact ttcaacgcaa  10980
aaccggactt ttccctgttc ctgcaggccc tctcctggga gattgatgat caggccggga  11040
tcgaggtgag gaatgacctg ttgcgcgagg tcggtcacgg catggccggt cggctgcagc  11100
ctccgctgtg caacaccatt catcagctgc agatcgagct gaactcgctg ctggccatga  11160
tcaactgggg ctatgtgcag cttgaactgc tgcccgagga ccatgccatg cgcatcgtcc  11220
atgaggacct gccccaggtg ggcagcgcgg gcgagccggc cggcacatgg ctggcccccg  11280
tgctcgaagg gctgtatggc cgctggatca cgtcgcagcc gggtgccttt ggcgattatg  11340
tcgtcacccg cgatgtggat gcggaggatc tcaactccgt tcccagccag acgatcatcc  11400
tgtacatgcg cacccgcagc agcagcaact gaagaaggag atatacatat gagtaaagga  11460
gaagaacttt tcactggagt tgtcccaatt cttgttgaat tagatggtga tgttaatggg  11520
cacaaattct ctgtcagtgg agagggtgaa ggtgatgcaa catacggaaa acttaccctt  11580
aaatttattt gcactactgg aaagctacct gttccatggc caacacttgt cactactttc  11640
tcttatggtg ttcaatgctt ttcaagatac ccagatcata tgaaacagca tgactttttc  11700
aagagtgcca tgcccgaagg ttatgtacag gaaagaacta tatttttacaa agatgacggg  11760
aactacaaat cacgtgctga agtcaagttt gaaggtgata ccctcgttaa tagaattgag  11820
ttaaaaggta ttgattttaa agaagatgga aacattcttg gacacaaaat ggaatacaac  11880
tataactcac acaatgtata catcatggca gacaaacaaa agaatggaat caaagttaac  11940
ttcaaaatta gacacaacat tgaagatgga agcgttcaac tagcagacca ttatcaacaa  12000
aatactccaa ttggcgatgg ccctgtcctt ttaccagaca accattacct gtccacacaa  12060
tctgcccttt ccaaagatcc caacgaaaag agagatcaca tgatccttct tgagtttgta  12120
acagctgctg ggattacaca tggcatggat gaactataca aataaaagga ggaacaagcc  12180
gcatgaaacc atcccgcaag tcattcctgc tttccgccgt ggcgtggggg ctggtggccg  12240
cgctgcccgc ccatgcccgc cacgcggcca cggctggtga cccggccgat gaccaggcgc  12300
```

```
ggcaggtgct cgcgcatatg agccttcagg acaagatggc ccttctgttc agtgtggacg  12360
ggggcggctt caatggcagt gtcgcacctc cggggggctt gggttcggcg gcgtatctgc  12420
gtgccccggc gggttcgggc ctgccggacc tgcagatatc ggatgcgggg cttggcgtgc  12480
gcaaccccgc gcatatccgg cccaatggtg cggcggtttc cctgccatcg ggtctggcca  12540
cggccagcac atgggatgtg gacatggccc ggcaggcagg tgaaatgatc gggcgcgagg  12600
cctggctgag cgggttcaac atcctgctgg gcggtggtgc cgacctgacg cgcgacccgc  12660
gtggcggccg caattttgaa tatgcggggg aagacccgct ccagaccggg cggatggtgg  12720
gcagcaccat tgccggcatc cagtcgcagc atgtgatttc cacgctcaag cattacgcga  12780
tgaacgacct tgagacatcg cgcatgacca tgagtgccga tatcgacccc gtagccatgc  12840
gtgagagcga cctgctgggt ttcgagattg cgattgaaac cgggcatccc ggttccgtca  12900
tgtgttcgta caaccgggtg aatgacctgt atgcgtgtga aaacccgtac ctgctgaaca  12960
cgacgctgaa gcaggactgg cattaccccg gctttgtcat gtccgactgg ggcgccacgc  13020
attcctccgc ccgtgcggcg ctggcgggac tggatcagga atcggctggt gaccatgccg  13080
atgcgcgccc ctatttcacc gctctgttgg cggcggatgt aaaggcgggg cgtgtgcccg  13140
tcgcccgtat tgacgacatg gcgcagcgca ttgtccgctc cctgttcgcg gcggggctgg  13200
tggcccatcc gccgcagcgc gggccgctgg atgtggtgac cgacaccctt gtggcccagc  13260
gtgatgagga agaaggcgcg gttctgctgc gcaacgaagg gggtatcctg ccgctttccc  13320
ccaccgcgcg catcgcggtc attggcgggc atgccgatgc gggcgtgatc tcgggcgggg  13380
ggtccagcca ggtcgatccc atcgggggtg aggcggtcaa gggaccgggc aagaaggaat  13440
ggccgggtga tccggtctat ttcccgtcat ccccgctcaa ggccatgcgg gccgaggccc  13500
ccaacgcgca catcacctat gaatccggca ccaatatcgc cgccgccgtg cgcgccgcgc  13560
gggcggccga tgtggcggtc gtgtatgcaa cgcagttcac cttcgagggg atggacgcgc  13620
ccagcatgca ccttgatgcc aatgccgacg cgctgatcac agccgtggcc gcggccaacc  13680
cgcgtaccgt ggtggtgatg gaaaccggcg acccggtgct catgccatgg aacagcagcg  13740
ttgcgggcgt gctggaggca tggttccccg gttccggcgg tgggccggcc attgcacgcc  13800
tgctgtttgg caaggttgcg ccctcgggcc acctgaccat gaccttcccg caggcggaaa  13860
gccagctggc ccatcccgat attgccggtg tgacggcgga caacgtgttc gagatgcagt  13920
tcaagaccga tcaggaactg gtctatgacg aaggcagcga cgtgggctac cgctggtttg  13980
accgcaacca tctcaagccg ctctatccct tcggttacgg tctgacctac accacgttca  14040
gcaccgatgg cctggcggtg cacaggcatc atgatgcggt gacggtcacc tttaccgtac  14100
ataataccgg caaccgcccc ggtgtggatg tgccgcaggt ctatgtgggc ctgcccgatg  14160
gcggggcacg caggctggcg ggctggcagc gggtcagtct ggcaccgggt gaaagccgtg  14220
cggtgacggt acagcttgat ccgcgcctgc tggcgcattt tgacgggaag aaggaccgct  14280
ggagcattcc ttcgggcaca ttccggctgt ggcttggcac gtccgccacg gatgacagcc  14340
agcaggcaag cctgcacctg tccggtcgca ccttcgcgcc ctgatgcctg gcggcagtag  14400
cgcggtggtc ccacctgacc ccatgccgaa ctcagaagtg aaacgccgta gcgccgatgg  14460
tagtgtgggg tctccccatg cgagagtagg gaactgccag gcatcaaata aaacgaaagg  14520
ctcagtcgaa agactgggcc tt                                             14542
```

GENETICALLY ENGINEERED MICROORGANISMS

CROSS-REFERENCE

This application is a 371 National Stage filing and claims the benefit under 35 U.S.C. § 120 to International Application No. PCT/EP2020/0084505, filed 3 Dec. 2020, which claims priority to Great Britain Application No. GB1917651.0, filed 3 Dec. 2019 and Great Britain Application No. GB2016372.1, filed 15 Oct. 2020, each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, is named Sequence_Listing ST25.txt and is 63 kilobytes in size.

FIELD OF THE INVENTION

The present invention relates to genetically engineered microorganisms, such as bacteria, modified to increase production of cellulose and methods of producing said genetically engineered microorganisms.

BACKGROUND

Drought and extreme heat are the largest climate-related threats to global agricultural production. A worsening climate means more extreme, unpredictable weather events that can range from acute large volumes of rain to prolonged periods of drought. These events have direct impact on crop yield. When rain occurs, the soil has a maximum absorption capacity, and the crop has a maximum uptake retention capacity. The remaining water, which can be substantial in dramatic weather events, is not utilised and often runs off the land, leading to localised flooding. Water shortage is a major global concern. 70% of global water consumption is from agricultural demand, and this is expect to increase 19% by 2050. Water consumption is a major impediment for global crop production. Within environments where drought is prevalent, low crop yields occur. By increasing the crop's tolerance to environmental drought, it is possible to improve the sustainability of the global crop supply. Due to rain precipitation in hotter climates being more sporadic, farmers are forced to irrigate their land continuously. This requires huge volumes of water that will ultimately not be utilised by the plant and will evaporate. The abiotic stress incurred by crops in drought prone climates, results in reduced yield and inefficient water management. With a growing population and an ever worsening climate conditions, many strategies have been suggested to alleviate water demand, however as of yet, none have used a biological active water retentive solution to crop water management. Previous strategies have focused on genetically modifying the crop directly, to make them more resistant, or through the addition of additives in the soil. However, none of these approaches have provided an effective solution to the problem of water shortage in global crop production. Crop sustainability is essential for population growth and a food source for billions of people. Not only do crops feed the human population, they also support the animal farming industry, as a food supply. Therefore, now more than ever, a drastic change is required to support our growing world, but this solution must be environmentally friendly and efficient.

Cellulose

Cellulose is a polysaccharide consisting of a linear chain of several hundred to many thousands of $\beta(1\rightarrow4)$ linked D-glucose units. Cellulose is an important structural component of the primary cell wall of green plants, many forms of algae and the oomycetes. Additionally, some species of bacteria, principally of the genera *Acetobacter*, Sarcina ventriculi and *Agrobacterium*, secrete cellulose to firm biofilms. Bacterial cellulose is now produced for a variety of commercial applications including textiles, cosmetics, and food products, as well as medical applications. Expression of bacterial cellulose in bacteria has been described in the art. For example, Chinese patent application CN108060112 describes a bacterial cellulose producing bacterial strain, specifically, overexpression of a BcsB subunit in *Acetobacter xylinum*. Additionally, Buldum et al. (2018) describes recombinant biosynthesis of bacterial cellulose in genetically modified *Escherichia coli*. Whilst Florea et al. (2016) describes engineering control of bacterial cellulose production in *Komagataeibacter rhaeticus* using a genetic toolkit.

Carbon Capture

Carbon sequestration on agricultural land is one way to reduce carbon emissions from agriculture and mitigate climate change. Atmospheric concentrations of carbon dioxide can be lowered either by reducing emissions or by taking carbon dioxide out of the atmosphere and storing it in the soil. The long-term conversion of grassland and forestland to cropland (and grazing lands) has resulted in historic losses of soil carbon worldwide but there is a major potential for increasing soil carbon through restoration of degraded soils and widespread adoption of soil conservation practices. The decline in soil quality has also been exacerbated by the use of chemical fertilisers.

Historically, land-use conversion and soil cultivation have been a prominent source of greenhouse gases (GHGs) to the atmosphere. It is estimated that they are still responsible for about one-third of GHG emissions. However, improved agricultural practices can help mitigate climate change by reducing emissions from agriculture and other sources and by storing carbon in soils.

The development of agriculture during the past centuries and particularly in last decades has entailed depletion of substantive soil carbon stocks. Agricultural soils are among the planet's largest reservoirs of carbon and hold potential for expanded carbon sequestration (CS), and thus provide a prospective way of mitigating the increasing atmospheric concentration of $CO_2$. There is general agreement that the technical potential for sequestration of carbon in soil is significant, and some consensus on the magnitude of that potential. Croplands worldwide could sequester between 0.90 and 1.85 Pg C/yr, i.e. 26-53% of the target of the "4p1000 Initiative: Soils for Food Security and Climate".

At the same time, this process provides other important benefits for soil, crop and environment quality, prevention of erosion and desertification, and for the enhancement of biodiversity. Land degradation does not only reduce crop yields but often reduces the carbon content of agro-ecosystems, and may reduce biodiversity.

The climate of earth has been experiencing an unprecedented change due to the rapidly increasing amount of GHGs in the atmosphere. There is a need to devise multiple strategies to offset the current release of GHGs into atmosphere. $CO_2$ has a prominent share in global warming amongst all GHGs in atmosphere. Soil carbon sequestration is a promising approach to offset the rising amount of $CO_2$ in the atmosphere. Both partially degraded and agricultural soils have a considerable potential to minimise the elevated $CO_2$ levels in the atmosphere. On a global scale, the soils can retain two-fold more carbon than that present in the atmosphere or captured in vegetation. The temperature, soil moisture and elevated $CO_2$ levels are the dominant climatic factors affecting the soil carbon sequestration. Soil carbon sequestration is also strongly influenced by various edaphic factors i.e. soil texture, soil structure, soil porosity, soil compaction, soil mineralogy, and soil microbial community composition etc. Additionally, agricultural practices like land-use changes, plant residue management, agro-chemicals etc. influence soil organic carbon (SOC) stocks, either directly (e.g. by altering the amount of carbon being added in the soil) or indirectly (e.g. by influencing soil aggregation and thereby accelerating microbial decomposition processes). Besides offsetting the rapidly increasing atmospheric GHGs, soil carbon sequestration may potentially improve the soil quality and advances the food security. It may play a crucial role in sustainable agriculture because it is highly sustainable and an environmentally friendly approach. It can enhance the soil quality by improving soil health parameters (i.e. water retaining capacity of soil) followed by improved crop production on sustainable basis.

The present invention has been devised in light of the above considerations.

SUMMARY OF THE INVENTION

The invention is based on overexpression of protein components responsible for the synthesis and secretion of cellulose in microorganisms such as root-associated bacteria to achieve an increase in water retention around plant roots. This increase in water retention around plant roots is thought to reduce the amount of water irrigation required, and therefore improve the crop's tolerance to environmental drought.

Thus the invention at its broadest provides a genetically engineered microorganism modified to overexpress at least one protein involved in synthesis and/or secretion of cellulose relative to a reference microorganism, optionally wherein the cellulose is bacterial cellulose. Preferably, the microorganism (and reference microorganism) is a bacterium such as a root-associated bacterium.

In one aspect of the invention, provided is a genetically engineered microorganism for producing cellulose, wherein the microorganism is genetically modified to overexpress at least one protein involved in synthesis and/or secretion of cellulose, wherein the microorganism is modified with exogenous genes comprising a bcsA gene, a bcsB gene, a bcsC gene, a bcsD gene, and a ccpAx gene. In some embodiments, the microorganism is further modified with an exogenous cmcAx gene and/or an exogenous bglAx gene. In some embodiments, the microorganism is modified with an exogenous nucleic acid comprising a bcsA gene, a bcsB gene, a bcsC gene, a bcsD gene, and at least a ccpAx gene. In some embodiments, the genes are heterologous. In some embodiments, the genes are each isolated from *K. xylinus*.

In some embodiments, the genetically engineered microorganism is a bacterium, optionally a root-associated bacterium. In some embodiments, the genetically engineered microorganism is a plant growth-promoting rhizobacterium. In some embodiments, the microorganism is a *Pseudomonas* bacterium. In some embodiments, the rhizobacterium is not *Komagataeibacter xylinus* (also known as *Acetobacter xylinum* and *Gluconacetobacter xylinus*). In some embodiments, expression of the genes is regulated by a cell-density quorum sensing system. In some embodiments, a quorum sensing operon is inserted into the host cell. In some embodiments, the quorum sensing system comprises a gene encoding a sensor kinase and a gene encoding a response regulator. In further embodiments, the quorum sensing system further comprises a quorum sensing regulated promoter. In alternative embodiments, the quorum sensing system comprises a gene encoding a signalling molecule (autoinducer) and a gene encoding a transcriptional/response regulator. In further embodiments, the quorum sensing system further comprises a quorum sensing regulated promoter.

In some aspects, provided is a method of increasing production of cellulose in a microorganism compared to a reference microorganism, wherein the method comprises a step of modifying the microorganism to overexpress at least one protein involved in synthesis and/or secretion of cellulose, wherein the microorganism is modified with exogenous genes comprising a bcsA gene, a bcsB gene, a bcsC gene, a bcsD gene, and a ccp gene. In some embodiments, the microorganism is further modified with an exogenous cmc gene and/or an exogenous bg/gene. In some embodiments, the microorganism is a bacterium, optionally a plant growth-promoting rhizobacterium.

The invention provides a genetically engineered microorganism for producing cellulose, wherein the microorganism is genetically modified to overexpress at least one protein involved in synthesis and/or secretion of cellulose. In some embodiments, the cellulose produced by the genetically engineered microorganism is bacterial cellulose. In some embodiments, the microorganism is genetically modified to overexpress at least one protein from a cellulose synthase complex. In some embodiments, the microorganism is modified to overexpress at least one, at least two, at least three, or at least four of the proteins from a cellulose synthase complex. In some embodiments, the cellulose synthase complex is a bacterial cellulose synthase complex. In some embodiments, cellulose production is increased in the genetically modified microorganism compared to a reference microorganism. In some embodiments, the reference microorganism is of the same species as the modified microorganism. The reference microorganism may be the same strain as the modified microorganism. In some embodiments, the microorganism is a wild-type microorganism. In some embodiments, the reference microorganism of the same species or same strain is a wild-type microorganism of the same species or same strain. In some embodiments, the genetically engineered microorganism is selected from a bacterial cell, a fungal cell or an algae cell. In some embodiments, the genetically engineered microorganism is a bacterium. In further embodiments, the genetically engineered microorganism is a root-associated bacterium.

In some embodiments, the genetically engineered microorganism of the invention is modified to overexpress a cellulose synthase complex. In some embodiments, the genetically modified microorganism is modified with an exogenous nucleic acid encoding at least one protein from a cellulose synthase complex. In other embodiments, overexpression of at least one protein of a cellulose synthase complex is achieved by increasing transcription and/or translation of the at least one protein of an endogenous cellulose synthase complex.

In some embodiments, the genetically modified microorganism is modified with an exogenous nucleic acid encoding at least one protein from a cellulose synthase complex. In some embodiments, the microorganism is modified to with an exogenous nucleic acid encoding at least one, at least two, at least three, or at least four of the proteins from a cellulose synthase complex. In some embodiments, the genetically engineered microorganism is modified with at least one of the following genes of the bcs operon: bcsA; bcsB; bcsC; and/or bcsD. In further embodiments, the exogenous nucleic acid comprises a bcs operon. In another further embodiment, the bcs operon encodes four protein subunits BcsA, BcsB, BcsC, and BcsD. In some embodiments, the exogenous nucleic acid further comprises at least one of the following genes or operon: cmcAx gene; ccpAx gene; bglAx gene; pgm gene; galU gene; cdg operon; and/or dgc gene. In some embodiments, the exogenous nucleic acid comprises a bcs operon, a cmcAx gene, a ccpAx gene, and a bglAx gene. In some embodiments, the exogenous nucleic acid comprises a bcs operon, a cmc gene, a ccp gene, a bg/gene, a pgm gene, a galU gene, a cdg operon and a dgc gene. In some embodiments, the exogenous nucleic acid consists of a bcs operon, a cmc gene, a ccp gene, a bgl gene, a pgm gene, a gall gene, a cdg operon and a dgc gene. In some embodiments, the bcs operon, cmc gene, ccp gene, bgl gene, pgm gene, galU gene, cdg operon, and/or dgc gene are each isolated from *K. xylinus*.

In some embodiments, the microorganism is selected from *Pseudomonas fluorescens*, and *Bacillus megaterium*. In a further embodiment, the microorganism is *Pseudomonas fluorescens*. In another further embodiment, the microorganism is *Pseudomonas fluorescens* SBW25. In another further embodiment, the microorganism is *Pseudomonas fluorescens* F113. In another further embodiment, the microorganism is *Pseudomonas fluorescens* CHA0. In another further embodiment, the microorganism is *Pseudomonas fluorescens* Pf-5. In another further embodiment, the microorganism is *Pseudomonas fluorescens* FW300 N2E2.

In some embodiments, the cellulose produced by the genetically engineered microorganism of the invention is secreted outside of the cell. In a further embodiment, the secreted cellulose forms a network outside of the cell. In some embodiments, the secreted network forms around plant roots. In some embodiments, the secreted cellulose network increases water retention around plant roots. In some embodiments, the plant is a cereal plant, a corn plant, a rice plant, a wheat plant, or a soy plant.

In a second aspect of the invention, a method of increasing production of cellulose in a microorganism compared to a reference microorganism, wherein the method comprises a step of modifying the microorganism to overexpress at least one protein involved in synthesis and/or secretion of cellulose. In some embodiments, the microorganism is modified to overexpress at least one protein from a cellulose synthase complex. In some embodiments, the reference microorganism is of the same species as the modified microorganism. In some embodiments, the reference microorganism is a wild-type microorganism. In some embodiments, the reference microorganism of the same species is a wild-type microorganism of the same species. In some embodiments, the genetically engineered microorganism is modified with an exogenous nucleic acid encoding at least one protein from a cellulose synthase complex. In some embodiments, the exogenous nucleic acid encoding at least one protein from a cellulose synthase complex is integrated into the genome of the microorganism. In some embodiments, the cellulose is bacterial cellulose. In some embodiments the exogenous nucleic acid comprises a bcs operon. In further embodiments, the exogenous nucleic acid of the vector further comprises at least one of cmcAx gene, ccpAx gene, bglAx gene, pgm gene, a galU gene, a cdg operon, and a dgc gene. In some embodiments, the genetically engineered microorganism is selected from a bacterial cell, a fungal cell or an algae cell. In some embodiments, the genetically engineered microorganism is a bacterium. In further embodiments, the genetically engineered microorganism is a root-associated bacterium.

In a third aspect of the invention, a vector comprising an exogenous nucleic acid that encodes at least one protein from a cellulose synthase complex is provided. In some embodiments, the exogenous nucleic acid of the vector comprises a bcs operon. In further embodiments, the exogenous nucleic acid of the vector further comprises at least one of a cmcAx gene, a ccpAx gene, a bglAx gene, a pgm gene, a galU gene, a cdg operon, and a dgc gene. In some embodiments, the exogenous nucleic acid of the vector comprises a bcs operon, a cmcAx gene, a ccpAx gene, and a bglAx gene. In some embodiments, the exogenous nucleic acid of the vector comprises a bcs operon, a cmcAx gene, a ccpAx gene, a bglAx gene, a pgm gene, a galU gene, a cdg operon and a dgc gene. In some embodiments, the exogenous nucleic acid of the vector consists of a bcs operon, a cmcAx gene, a ccpAx gene, a bglAx gene, a pgm gene, a galU gene, a cdg operon and a dgc gene. In some embodiments, the bcs operon, cmcAx gene, ccpAx gene, bglAx gene, pgm gene, galU gene, cdg operon, and/or dgc gene are each isolated from *K. xylinus*. In some embodiments, the vector is an isolated vector. In some embodiments, the genes are heterologous.

In a fourth aspect, the invention provides a method of producing a genetically engineered microorganism for producing cellulose, wherein the method comprises a step of modifying the microorganism with an exogenous nucleic acid that encodes at least one protein from a cellulose synthase complex comprising:

a) isolating a microorganism; and
b) introducing the vector of the invention into the microorganism.

In some embodiments, the microorganism is modified with an exogenous nucleic acid encoding at least one, at least two, at least three, or at least four of the proteins from a cellulose synthase complex. In some embodiments, the genetically engineered microorganism is selected from a bacterial cell, a fungal cell or an algae cell. In some embodiments, the genetically engineered microorganism is a bacterium. In further embodiments, the genetically engineered microorganism is a root-associated bacterium.

In some embodiments, the vector of the invention is introduced into the microorganism by electroporation. In some embodiments, the vector of the invention is introduced into the microorganism by transfection. In some embodiments, the exogenous nucleic acid encoding at least one protein from a cellulose synthase complex is integrated into the genome of the microorganism. In some embodiments, at least one, at least two, at least three, or at least four of the proteins from a cellulose synthase complex is integrated into the genome of the microorganism. In some embodiments, the vector of the invention is introduced into the microorganism such that two copies, three copies, or four copies and so on are integrated into the genome of the microorganism to increase the copy number of that gene or genes. In some embodiments, cellulose production is increased in the genetically modified microorganism compared to a reference microorganism. In some embodiments, the reference microorganism is of the same species or strain. In some embodiments, the reference microorganism is a wild-type microorganism. In some embodiments, the reference microorganism is a wild-type microorganism of the same species or strain. In some embodiments, the cellulose is bacterial cellulose. In some embodiments, the cellulose synthase complex is a bacterial cellulose synthase complex.

In a fifth aspect, provided is a genetically engineered microorganism obtainable by the method of producing a genetically engineered microorganism for producing cellulose. In another aspect, the invention provides an isolated genetically engineered microorganism of the invention. In an alternative aspect of the invention, provided is a population comprising the genetically engineered microorganism of the invention. In some embodiments, the genetically engineered microorganism is selected from a bacterial cell, a fungal cell or an algae cell. In some embodiments, the genetically engineered microorganism is a bacterium. In further embodiments, the genetically engineered microorganism is a root-associated bacterium.

In another aspect, the invention provides a composition comprising the genetically engineered population of microorganisms of the invention. In some embodiments, the composition is applied to a plant in a liquid formulation. In alternative embodiments, the composition is applied to a plant as an inoculum. In some embodiments, the inoculants are peat-based formulations. In further embodiments, the formulations are used to coat seeds or pellets for sowing in furrows. In some embodiments, the genetically modified microorganism of the invention is delivered to plants in microbeads. In further embodiments, the microbeads are alginate microbeads. In some embodiments, the composition further comprises a fertiliser and/or a biofertiliser. In some embodiments, the composition is applied to a plant after planting but before harvest of said plant. In some embodiments, the composition is applied to the soil before planting a plant. In some embodiments, the plant is a cereal plant, a corn plant, a rice plant, a wheat plant, or a soy plant. In some embodiments, the genetically engineered microorganism is selected from a bacterial cell, a fungal cell or an algae cell. In some embodiments, the genetically engineered microorganism is a bacterium. In further embodiments, the genetically engineered microorganism is a root-associated bacterium.

In another aspect, the invention provides a method of increasing water-retention around plant roots, comprising applying a genetically engineered microorganism to soil surrounding a plant root, wherein the microorganism is genetically modified to overexpress at least one protein involved in synthesis and/or secretion of cellulose. In some embodiments, the microorganism is selected from the genetically engineered microorganism of the invention, the isolated genetically engineered microorganism of the invention, the population of genetically engineered microorganisms of the invention, or the composition of the invention. In some embodiments, the plant is a cereal plant, a corn plant, a rice plant, a wheat plant, or a soy plant. In some embodiments, the genetically engineered microorganism is selected from a bacterial cell, a fungal cell or an algae cell. In some embodiments, the genetically engineered microorganism is a bacterium. In further embodiments, the genetically engineered microorganism is a root-associated bacterium.

In another aspect, the invention provides a method of reducing water consumption in agriculture, comprising applying a genetically engineered microorganism to soil surrounding a plant root, wherein the microorganism is genetically modified to overexpress at least one protein involved in synthesis and/or secretion of cellulose. In some embodiments, the microorganism is selected from the genetically engineered microorganism of the invention, the isolated genetically engineered microorganism of the invention, the population of genetically engineered microorganisms of the invention, or the composition of the invention. In some embodiments, the plant is a cereal plant, a corn plant, a rice plant, a wheat plant, or a soy plant. In some embodiments, the genetically engineered microorganism is selected from a bacterial cell, a fungal cell or an algae cell. In some embodiments, the genetically engineered microorganism is a bacterium. In further embodiments, the genetically engineered microorganism is a root-associated bacterium.

In another aspect, the invention provides a plant comprising the genetically engineered microorganism of the invention, the isolated genetically engineered microorganism of the invention, the population of genetically engineered microorganisms of the invention, or the composition of the invention, wherein the genetically engineered microorganism, isolated genetically engineered microorganism, or the population of genetically engineered microorganisms is associated with the plant roots. In some embodiments, the plant is a cereal plant, a corn plant, a rice plant, a wheat plant, or a soy plant. In some embodiments, the genetically engineered microorganism is selected from a bacterial cell, a fungal cell or an algae cell. In some embodiments, the genetically engineered microorganism is a bacterium. In further embodiments, the genetically engineered microorganism is a root-associated bacterium.

In another aspect, the invention provides a method of capturing carbon, comprising applying a genetically engineered microorganism to soil surrounding a plant root, wherein the microorganism is genetically modified to overexpress at least one protein involved in synthesis and/or secretion of cellulose, and wherein the carbon is converted to cellulose by the microorganism.

In some embodiments the genetically engineered microorganism is a microorganism of the invention, an isolated genetically engineered microorganism of the invention, a population of genetically engineered microorganisms of the invention, or a composition of the invention. In some embodiments, the carbon is absorbed as carbohydrates secreted from a plant and the carbohydrates are converted into cellulose by the microorganism. In some embodiments, production of cellulose results in increased water-retention around plant roots. In some embodiments, the genetically engineered microorganism is selected from a bacterial cell, a fungal cell or an algae cell. In some embodiments the genetically engineered microorganism is a bacterium. In further embodiments, the genetically engineered microorganism is a root-associated bacterium. In some embodiments, the microorganism is a mycorrhizal fungi (for example, arbuscular, ectomycorrhizal, ericoid and/or orchid).

Another aspect of the invention provides use of a genetically modified microorganism in agriculture, wherein the microorganism is genetically modified to overexpress at least one protein involved in synthesis and/or secretion of cellulose. In another aspect of the invention, use of a genetically modified microorganism to increase water-retention around plant roots, wherein the microorganism is genetically modified to overexpress at least one protein involved in synthesis and/or secretion of cellulose, is provided. Another aspect of the invention provides use of a genetically modified microorganism in carbon capture, wherein the microorganism is genetically modified to overexpress at least one protein involved in synthesis and/or secretion of cellulose, and wherein the carbon is converted into cellulose by the microorganism. In some embodiments, the genetically engineered microorganism is selected from a bacterial cell, a fungal cell or an algae cell. In some embodiments, the genetically engineered microorganism is a bacterium. In further embodiments, the genetically engineered microorganism is a root-associated bacterium. In some embodiments, the methods and uses described herein result in an increase in plant viability.

In some embodiments, provided is a genetically modified microorganism comprising one or more heterologous genes, wherein the genes comprise a bcsA gene, a bcsB gene, a bcsC gene, a bcsD gene, a cmcAx gene, a ccpAx gene, and/or a bglAx gene. In some embodiments, the microorganism is a bacterium. In further embodiments, the microorganism is a plant growth promoting rhizobacterium.

In some aspects, the invention provides a genetically engineered root-associated bacterium for producing cellulose, wherein the bacterium is genetically modified to overexpress at least one protein involved in synthesis and/or secretion of cellulose. In some embodiments, the cellulose produced by the genetically engineered root-associated bacterium is bacterial cellulose. In some embodiments, the bacterium is genetically modified to overexpress at least one protein from a cellulose synthase complex. In some embodiments, the bacteria is modified to overexpress at least one, at least two, at least three, or at least four of the proteins from a cellulose synthase complex. In some embodiments, the cellulose synthase complex is a bacterial cellulose synthase complex. In some embodiments, cellulose production is increased in the genetically modified bacterium compared to a reference bacterium. In some embodiments, the reference bacterium is of the same species as the modified bacterium. The reference bacterium may be the same strain as the modified bacterium. In some embodiments, the bacterium is a wild-type bacterium. In some embodiments, the reference bacterium of the same species or same strain is a wild-type bacterium of the same species or same strain.

In some embodiments, the genetically engineered root-associated bacterium of the invention is modified to overexpress a cellulose synthase complex. In some embodiments, the genetically modified bacterium is modified with an exogenous nucleic acid encoding at least one protein from a cellulose synthase complex. In other embodiments, overexpression of at least one protein of a cellulose synthase complex is achieved by increasing transcription and/or translation of the at least one protein of an endogenous cellulose synthase complex.

In some embodiments, the genetically modified root-associated bacterium is modified with an exogenous nucleic acid encoding at least one protein from a cellulose synthase complex. In some embodiments, the bacteria is modified to with an exogenous nucleic acid encoding at least one, at least two, at least three, or at least four of the proteins from a cellulose synthase complex. In some embodiments, the genetically engineered bacterium is modified with at least one of the following genes of the bcs operon: bcsA; bcsB; bcsC; and/or bcsD. In further embodiments, the exogenous nucleic acid comprises a bcs operon. In another further embodiment, the bcs operon encodes four protein subunits BcsA, BcsB, BcsC, and BcsD. In some embodiments, the exogenous nucleic acid further comprises at least one of the following genes or operon: cmcAx gene; ccpAx gene; bglAx gene; pgm gene; galU gene; cdg operon; and/or dgc gene. In some embodiments, the exogenous nucleic acid comprises a bcs operon, a cmcAx gene, a ccpAx gene, and a bglAx gene. In some embodiments, the exogenous nucleic acid comprises a bcs operon, a cmcAx gene, a ccpAx gene, a bglAx gene, a pgm gene, a galU gene, a cdg operon and a dgc gene. In some embodiments, the exogenous nucleic acid consists of a bcs operon, a cmcAx gene, a ccpAx gene, a bglAx gene, a pgm gene, a galU gene, a cdg operon and a dgc gene. In some embodiments, the bcs operon, cmcAx gene, ccpAx gene, bglAx gene, pgm gene, galU gene, cdg operon, and/or dgc gene are each isolated from *K. xylinus.*

In some embodiments, the root-associated bacterium is selected from *Pseudomonas fluorescens*, and *Bacillus megaterium*. In a further embodiment, the root-associated bacterium is *Pseudomonas fluorescens*. In another further embodiment, the root-associated bacterium is *Pseudomonas fluorescens* SBW25. In another further embodiment, the root-associated bacterium is *Pseudomonas fluorescens* F113. In another further embodiment, the root-associated bacterium is *Pseudomonas fluorescens* CHA0. In another further embodiment, the root-associated bacterium is *Pseudomonas fluorescens* Pf-5. In another further embodiment, the root-associated bacterium is *Pseudomonas fluorescens* FW300 N2E2.

In some embodiments, the cellulose produced by the genetically engineered root-associated bacterium of the invention is secreted outside of the cell. In a further embodiment, the secreted cellulose forms a network outside of the cell. In some embodiments, the secreted network forms around plant roots. In some embodiments, the secreted cellulose network increases water retention around plant roots. In some embodiments, the plant is a cereal plant, a corn plant, a rice plant, a wheat plant, or a soy plant.

In a second aspect of the invention, a method of increasing production of cellulose in a root-associated bacterium compared to a reference root-associated bacterium, wherein the method comprises a step of modifying the bacterium to overexpress at least one protein involved in synthesis and/or secretion of cellulose. In some embodiments, the bacterium is modified to overexpress at least one protein from a cellulose synthase complex. In some embodiments, the reference bacterium is of the same species as the modified bacterium. In some embodiments, the reference bacterium is a wild-type bacterium. In some embodiments, the reference bacterium of the same species is a wild-type bacterium of the same species. In some embodiments, the genetically engineered root-associated bacterium is modified with an exogenous nucleic acid encoding at least one protein from a cellulose synthase complex. In some embodiments, the exogenous nucleic acid encoding at least one protein from a cellulose synthase complex is integrated into the genome of the root-associated bacterium. In some embodiments, the cellulose is bacterial cellulose. In some embodiments the exogenous nucleic acid comprises a bcs operon. In further embodiments, the exogenous nucleic acid of the vector further comprises at least one of cmcAx gene, ccpAx gene, bglAx gene, pgm gene, a galU gene, a cdg operon, and a dgc gene.

In a third aspect of the invention, a vector comprising an exogenous nucleic acid that encodes at least one protein from a cellulose synthase complex is provided. In some embodiments, the exogenous nucleic acid of the vector comprises a bcs operon. In further embodiments, the exogenous nucleic acid of the vector further comprises at least one of a cmcAx gene, a ccpAx gene, a bglAx gene, a pgm gene, a galU gene, a cdg operon, and a dgc gene. In some embodiments, the exogenous nucleic acid of the vector comprises a bcs operon, a cmcAx gene, a ccpAx gene, and a bglAx gene. In some embodiments, the exogenous nucleic acid of the vector comprises a bcs operon, a cmcAx gene, a ccpAx gene, a bglAx gene, a pgm gene, a galU gene, a cdg operon and a dgc gene. In some embodiments, the exogenous nucleic acid of the vector consists of a bcs operon, a cmcAx gene, a ccpAx gene, a bglAx gene, a pgm gene, a galU gene, a cdg operon and a dgc gene. In some embodiments, the bcs operon, cmcAx gene, ccpAx gene, bglAx gene, pgm gene, galU gene, cdg operon, and/or dgc gene are each isolated from *K. xylinus*. In some embodiments, the vector is an isolated vector.

In a fourth aspect, the invention provides a method of producing a genetically engineered root-associated bacterium for producing cellulose, wherein the method comprises a step of modifying the bacterium with an exogenous nucleic acid that encodes at least one protein from a cellulose synthase complex comprising:

a) isolating a root-associated bacterium; and b) introducing the vector of the invention into the root-associated bacterium.

In some embodiments, the bacteria is modified with an exogenous nucleic acid encoding at least one, at least two, at least three, or at least four of the proteins from a cellulose synthase complex.

In some embodiments, the vector of the invention is introduced into the root-associated bacterium by electroporation. In some embodiments, the vector of the invention is introduced into the root-associated bacterium by transfection. In some embodiments, the exogenous nucleic acid encoding at least one protein from a cellulose synthase complex is integrated into the genome of the root-associated bacterium. In some embodiments, at least one, at least two, at least three, or at least four of the proteins from a cellulose synthase complex is integrated into the genome of the root-associated bacterium. In some embodiments, the vector of the invention is introduced into the bacterium such that two copies, three copies, or four copies and so on are integrated into the genome of the bacterium to increase the copy number of that gene or genes. In some embodiments, cellulose production is increased in the genetically modified bacterium compared to a reference bacterium. In some embodiments, the reference bacterium is of the same species or strain. In some embodiments, the reference bacterium is a wild-type bacterium. In some embodiments, the reference bacterium is a wild-type bacterium of the same species or strain. In some embodiments, the cellulose is bacterial cellulose. In some embodiments, the cellulose synthase complex is a bacterial cellulose synthase complex.

In a fifth aspect, provided is a genetically engineered root-associated bacterium obtainable by the method of producing a genetically engineered root-associated bacterium for producing cellulose. In another aspect, the invention provides an isolated genetically engineered root-associated bacterium of the invention. In an alternative aspect of the invention, provided is a bacterial population comprising the genetically engineered root-associated bacterium of the invention.

In another aspect, the invention provides a bacterial composition comprising the genetically engineered root-associated bacterial population of the invention. In some embodiments, the composition is applied to a plant in a liquid formulation. In alternative embodiments, the composition is applied to a plant as a bacterial inoculum. In some embodiments, the bacterial inoculants are peat-based formulations. In further embodiments, the formulations are used to coat seeds or pellets for sowing in furrows. In some embodiments, the genetically modified bacterium of the invention is delivered to plants in microbeads. In further embodiments, the microbeads are alginate microbeads. In some embodiments, the bacterial composition further comprises a fertiliser and/or a biofertiliser. In some embodiments, the bacterial composition is applied to a plant after planting but before harvest of said plant. In some embodiments, the bacterial composition is applied to the soil before planting a plant. In some embodiments, the plant is a cereal plant, a corn plant, a rice plant, a wheat plant, or a soy plant.

In another aspect, the invention provides a method of increasing water-retention around plant roots, comprising applying the genetically engineered root-associated bacteria of the invention, the isolated genetically engineered root-associated bacterium of the invention, the population of genetically engineered root-associated bacteria of the invention, or the bacterial composition of the invention to the surrounding soil of the plant. In some embodiments, the plant is a cereal plant, a corn plant, a rice plant, a wheat plant, or a soy plant.

In another aspect, the invention provides a method of reducing water consumption in agriculture, comprising applying the genetically engineered root-associated bacteria of the invention, the isolated genetically engineered root-associated bacterium of the invention, the population of genetically engineered root-associated bacteria of the invention, or the bacterial composition of the invention to the surrounding soil of the plant. In some embodiments, the plant is a cereal plant, a corn plant, a rice plant, a wheat plant, or a soy plant.

In another aspect, the invention provides a plant comprising the genetically engineered root-associated bacteria of the invention, the isolated genetically engineered root-associated bacterium of the invention, the population of genetically engineered root-associated bacteria of the invention, or the bacterial composition of the invention, wherein the genetically engineered root-associated bacterium, isolated genetically engineered root-associated bacterium, or the population of genetically engineered root-associated bacteria is associated with the plant roots. In some embodiments, the plant is a cereal plant, a corn plant, a rice plant, a wheat plant, or a soy plant.

In another aspect, the invention provides a method of capturing carbon, comprising applying a genetically engineered root-associated bacterium to soil surrounding a plant root, wherein the bacterium is genetically modified to overexpress at least one protein involved in synthesis and/or secretion of cellulose, and wherein the carbon is converted to cellulose by the bacterium.

In some embodiments the genetically engineered root-associated bacterium is a root-associated bacterium of the invention, an isolated genetically engineered root-associated bacterium of the invention, a population of genetically engineered root-associated bacteria of the invention, or a bacterial composition of the invention. In some embodiments, the carbon is absorbed as carbohydrates secreted from a plant and the carbohydrates are converted into cellulose by the bacterium. In some embodiments, production of cellulose results in increased water-retention around plant roots.

Another aspect of the invention provides use of a genetically modified root-associated bacterium in agriculture, wherein the bacterium is genetically modified to overexpress at least one protein involved in synthesis and/or secretion of cellulose. In another aspect of the invention, use of a genetically modified root-associated bacterium to increase water-retention around plant roots, wherein the bacterium is genetically modified to overexpress at least one protein involved in synthesis and/or secretion of cellulose, is provided. Another aspect of the invention provides use of a genetically modified root-associated bacterium in carbon capture, wherein the bacterium is genetically modified to overexpress at least one protein involved in synthesis and/or secretion of cellulose, and wherein the carbon is converted into cellulose by the bacterium. In some embodiments, the methods and uses described herein result in an increase in plant viability.

In some embodiments, the methods described herein result in an increase in plant viability.

In some embodiments of the invention, the root-associated bacterium is genetically modified with an exogenous nucleic acid comprising one or more heterologous genes, wherein the genes are selected from: a bcsA gene, a bcsB gene, a bcsC gene, a bcsD gene, a cmcAx gene, a ccpAx gene, and a bglAx gene.

In some aspects, the invention provides a genetically modified bacterium for producing cellulose, wherein the bacterium is genetically modified to overexpress at least one protein involved in synthesis and/or secretion of cellulose, and wherein the genetically modified bacterium is modified with an exogenous bcs operon, wherein the bcs operon comprises a bcsA gene, a bcsB gene, a bcsC gene, and a bcsD gene. In some embodiments, provided is a genetically engineered bacterium, wherein the bacterium is genetically modified to overexpress at least one protein involved in synthesis and/or secretion of cellulose, and wherein the genetically modified bacterium is modified with one or more heterologous genes, wherein the genes comprise a bcsA gene, a bcsB gene, a bcsC gene, a bcsD gene, and optionally a cmcAx gene, a ccpAx gene, and/or a bglAx gene. In some embodiments, the bacterium is not *Komagataeibacter xylinus* (also known as *Acetobacter xylinum* and *Gluconacetobacter xylinus*).

In some embodiments of the invention, the bacterium is genetically modified with an exogenous nucleic acid comprising one or more heterologous genes, wherein the genes are selected from: a bcsA gene, a bcsB gene, a bcsC gene, a bcsD gene, a cmcAx gene, a ccpAx gene, and a bglAx gene.

In some aspects, the invention provides a genetically engineered plant growth-promoting rhizobacterium for producing cellulose, wherein the rhizobacterium is genetically modified to overexpress at least one protein involved in synthesis and/or secretion of cellulose. In some embodiments, the rhizobacterium is modified with an exogenous nucleic acid comprising a bcs operon, wherein the bcs operon comprises a bcsA gene, a bcsB gene, a bcsC gene, and a bcsD gene. In some embodiments, the exogenous nucleic acid further comprises at least a ccpAx gene. In some embodiments, the exogenous nucleic acid further comprises a cmcAx gene, a ccpAx gene, and/or a bglAx gene. In some embodiments, the genes are heterologous. In some embodiments of the invention, the rhizobacterium is genetically modified with an exogenous nucleic acid comprising one or more heterologous genes, wherein the genes are selected from: a bcsA gene, a bcsB gene, a bcsC gene, a bcsD gene, a cmcAx gene, a ccpAx gene, and a bglAx gene.

In some embodiments, provided is a genetically engineered plant growth-promoting rhizobacterium for producing cellulose, wherein the rhizobacterium is genetically modified to overexpress at least one protein involved in synthesis and/or secretion of cellulose, and wherein the genetically modified rhizobacterium is modified with one or more heterologous genes, wherein the genes comprise a bcsA gene, a bcsB gene, a bcsC gene, a bcsD gene, and optionally a cmcAx gene, a ccpAx gene, and/or a bglAx gene. In some embodiments, the rhizobacterium is not *Komagataeibacter xylinus* (also known as *Acetobacter xylinum* and *Gluconacetobacter xylinus*).

The invention includes the combination of the aspects and preferred features described except where such a combination is clearly impermissible or expressly avoided.

SUMMARY OF THE FIGURES

Embodiments and experiments illustrating the principles of the invention will now be discussed with reference to the accompanying figures in which:

FIG. 4. FIG. 4A A depiction of a construction comprising *Pseudomonas synxantha* strain 2-79 chromosome—the phzl/R operon. FIG. 4B_A depiction of the construct comprising for insertion into the host microorganism, for example *Pseudomonas fluorescens.*

FIG. 5. FIG. 5A A depiction of a construct comprising *Pseudomonas putida* strain KT2440 chromosome rox quorum sensing system. FIG. 5B A depiction of a construct comprising the KT2440 QS-system for recombinant protein production in *Pseudomonas*, utilizing the regions upstream of the roxS/roxR-regulated genes shown in FIG. 5C. FIG. 5C A depiction of a construct for insertion into the host microorganism, for example *Pseudomonas fluorescens.*

DETAILED DESCRIPTION OF THE INVENTION

Figure 1:
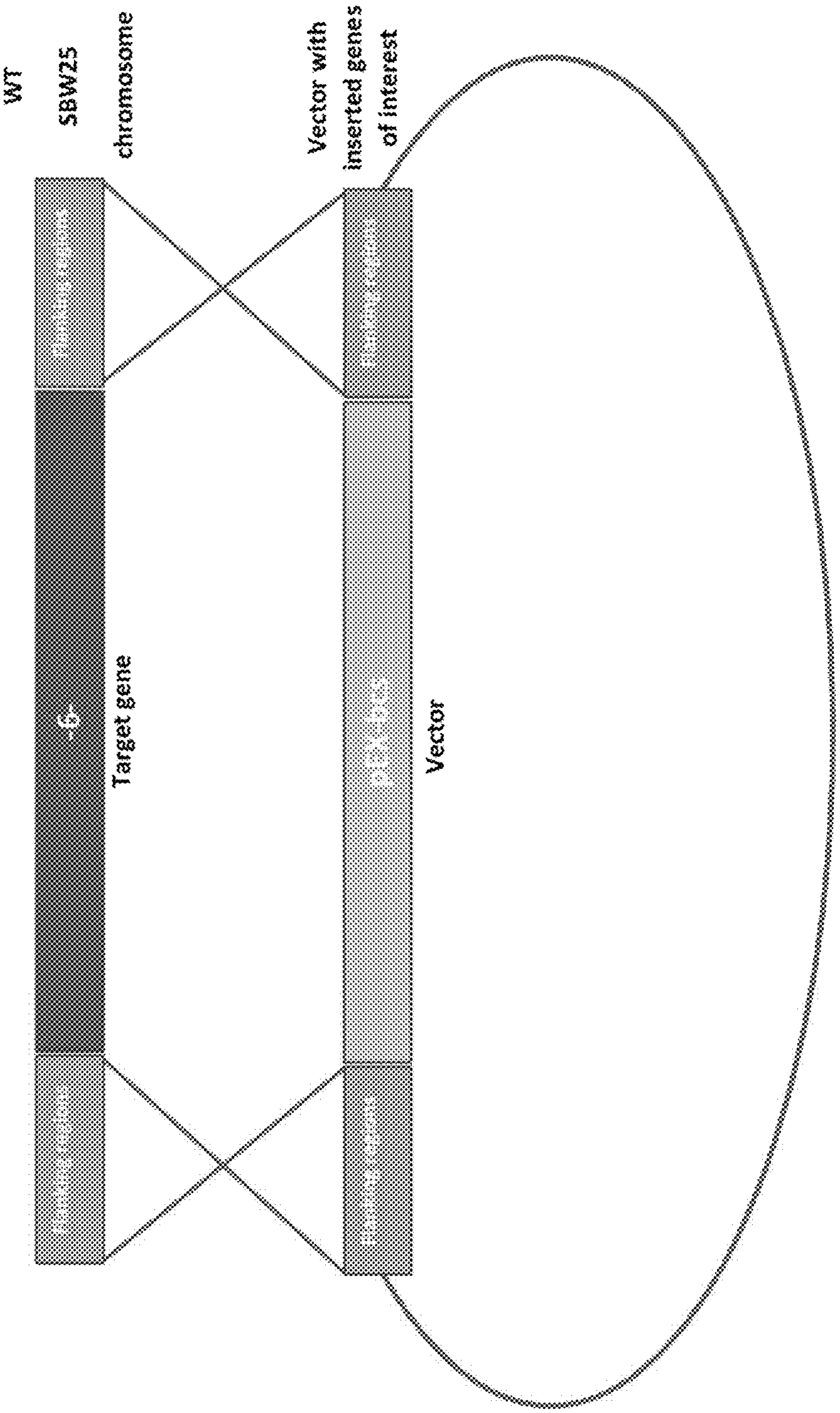
FIG. 1. A depiction of the genetic crossover from the shuttle vector (pEX18Ap) containing the bacterial cellulose genes of interest onto the chromosome of *P. fluorescens*, such as *P. fluorescens* SBW25, at locus-6-.
Figure 2:
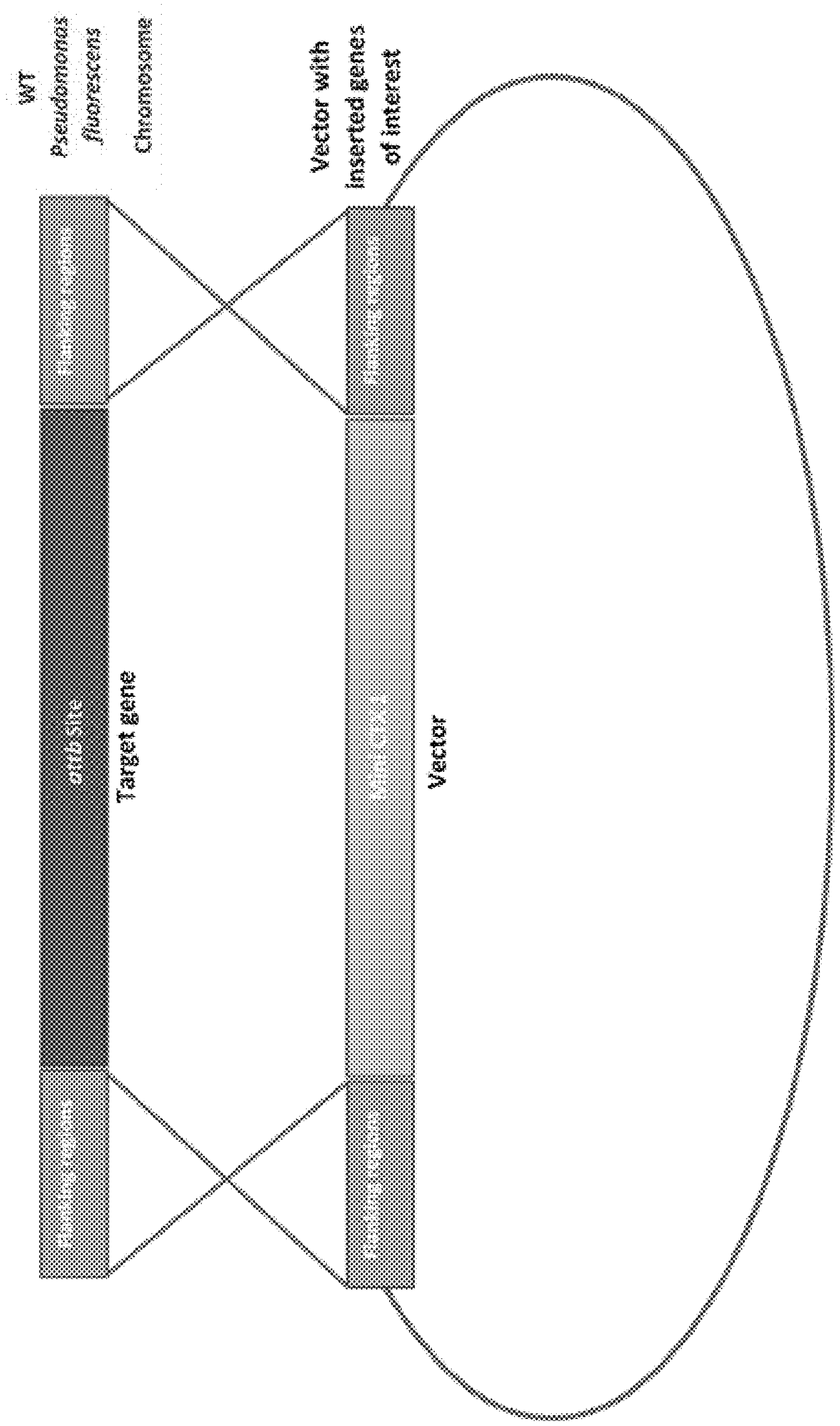
FIG. 2. A depiction of the genetic crossover from the Mini CTX1 vector containing the bacterial cellulose genes of interest onto the chromosome of *P. fluorescens* at the attb site (attB-5' TGAGTTCGAATCTCACCGCCTCCGCCATAT 3').

Aspects and embodiments of the present invention will now be discussed with reference to the accompanying figures. Further aspects and embodiments will be apparent to those skilled in the art. All documents mentioned in this text are incorporated herein by reference.

The present invention provides genetically engineered microorganisms such as a root-associated bacterium for producing cellulose, wherein the genetically engineered root-associated bacterium is genetically modified to increase cellulose production relative to a reference bacterium, typically of the same species. Typically, the genetically engineered root-associated bacterium are modified to overexpress proteins required for synthesis and/or secretion of cellulose, preferably a cellulose synthase complex.

As used herein "root-associated" bacterium or bacteria refers to a bacterium/bacteria that live on the plant root or surrounding the plant root. In some embodiments, the microorganisms are "root-associated", referring to a microorganism that lives on the plant root or surrounding the plant root. In further embodiments, the root-associated bacteria are Rhizobacteria. The root-associated bacteria may form symbiotic relationships with plants, promoting plant growth. (Such plant growth-promoting rhizobacteria are termed PGPR.) Without being bound by theory it is anticipated that once the root-associated bacteria are detached from the root, the bacterium would be unable to sustain viability, and so are unlikely to survive in the wider environment thereby preventing the spread of the genetically modified bacteria in the environment.

Examples of root-associated bacteria include, but are not limited to, *Agrobacterhim radiohacter, Bacillus acidocaldarms, Bacillus acidoterresiris, Bacillus agri, Bacillus aizawai, Bacillus albolactis, Bacillus alcalophilus, Bacillus alvei, Bacillus aminoglucosidicus, Bacillus aminovorans, Bacillus amylolyticus* (also known as *Paenibacilhis amylolyticus*), *Bacillus amyloliquefacieris, Bacillus aneiirinolyticus, Bacillus atropkaeus, Bacillus azotoformans, Bacillus badius, Bacillus cereus* (synonyms: *Bacillus endorhythmos, Bacillus medusa*), *Bacillus chilinosporus, Bacillus circulans, Bacillus coagulans, Bacillus endoparasiticus, Bacillus fastidiosus, Bacillus firmus, Bacillus kurstaki, Bacilhis lacticola, Bacilhis laclimorbus, Bacillus laciis, Bacillus laierospoms* (also known as *Brevibacillus laterosporus*), *Bacillus lautus, Bacillus leniimorbus, Bacillus lenius, Bacillus licheniformis, Bacillus maroccanus, Bacillus megaterium, Bacillus meiiens, Bacillus mycoides, Bacillus natto, Bacillus nematocida, Bacillus nigrificans, Bacillus nigrum, Bacillus pantothenticus, Bacillus papillae, Bacillus psychrosaccharolyticus, Bacillus pumilus, Bacillus siamensis, Bacillus smithii, Bacillus sphaericus, Bacillus subiilis, Bacillus thuringiensis, Bacillus tmiflagellatus, Bradyrhizobium japonicum, Brevibacillus brevis, Brevibacillus laterosporus* (formerly *Bacillus laterosporus*), *Chromobacterium suhisugae, Delflia acidovorans, Lactobacillus acidophilus, Lysobacter antibioticus, Lysobacter enzymogenes, Paenibacilhis alvei, Paenibacillus polymyxa, Paenibacillus popilliae* (formerly *Bacillus popilliae*), *Pantoea agglomerans, Pasteuria penetrans* (formerly *Bacillus penetrans*), *Pasteuria usgae, Pectobacterium carotovorum* (formerly *Erwinia carotovord*), *Pseudomonas aeruginosa, Pseudomonas aureofaciens, Pseudomonas cepacia* (formerly known as *Burkholderia cepacia*), *Pseudomonas chlororaphis, Pseudomonas fluorescens, Pseudomonas proradix, Pseudomonas putida, Pseudomonas syringae, Serralla entomophila, Serratia marcescens, Streptomyces colombiensis, Streptomyces galbus, Streptomyces goshikiensis, Streptomyces griseoviridis, Streptomyces lavendulae, Streptomyces prasinus, Streptomyces saraceticus, Streptomyces venezuelae, Xanthomonas campestris, Xenorhabdus luminescens, Xenorhabdus nematophila, Rhodococcus globerulus* AQ719 (NRRL Accession No. B-21663), *Bacillus* sp. AQ175 (ATCC Accession No. 55608), *Bacillus* sp. AQ 177 (ATCC Accession No. 55609), *Bacillus* sp. AQ178 (ATCC Accession No. 53522), and *Streptomyces* sp. strain NRRL Accession No. B-30145.

In some embodiments, the bacterium *Pseudomonas fluorescens* or *Bacillus megaterium*. In a further embodiment, the bacterium is *Pseudomonas fluorescens*. In preferred embodiments, the bacterium is *Pseudomonas fluorescens* SWB25. In another further embodiment, the bacterium is *Pseudomonas fluorescens* F113. In another further embodiment, the bacterium is *Pseudomonas fluorescens* CHA0. In another further embodiment, the bacterium is *Pseudomonas fluorescens* Pf-5. In another further embodiment, the bacterium is *Pseudomonas fluorescens* FW300 N2E2.

Rhizobacteria colonise the surface of the root, or superficial intercellular space of the host plant, often forming root nodules. In some embodiments, the root-associated bacteria are plant growth-promoting rhizobacteria (PGPR). Some common examples of PGPR genera exhibiting plant growth promoting activity are: *Pseudomonas, Azospirillum, Bacillus*, etc. Other known PGPRs include *Mesorhizobium* ciceri, *Burkholderia ambifaria, Mycobacterium phlei*, and *G. diazotrophicus* It is known by the skilled person that PGPR describes soil bacteria that colonise the roots of plants and enhance plant growth. PGPR is not intended to cover bacteria which have a pathogenic effect on the plant, for example, deleterious rhizobacteria (DRB). Six strains of rhizobacteria have been identified as being DRB, these include: the genera *Enterobacter, Klebsiella, Citrobacter, Flavobacterium, Achromobacter*, and *Arthrobacter.*

In some embodiments, the bacterium is a gram-negative bacterium. In some embodiments, the bacterium is a *Pseudomonas* genus bacterium. In some embodiments, the bacterium is not *Komagataeibacter xylinus* (also known as *Acetobacter xylinum* and *Gluconacetobacter xylinus*).

In some embodiments, the bacterium is selected from the following *Pseudomonas fluorescens* strains: *Pseudomonas fluorescens* CHA0 (CP043179.1); *Pseudomonas fluorescens* F113 (CP003150.1); *Pseudomonas fluorescens* FW300 N2E2 (CP015225.1); *Pseudomonas fluorescens* Pf-275 (CP031648.1); *Pseudomonas fluorescens* Pf-5 (CP000076.1); *Pseudomonas fluorescens* Pf0-1 (CP000094.2); *Pseudomonas fluorescens* FR1 (CP025738.1); *Pseudomonas fluorescens* DR133 (CP048607.1); and *Pseudomonas fluorescens* 2P24 (CP025542.1). Strains CHA0 and Pf-5 are now considered to belong to a novel bacterial species *Pseudomonas protegens*, which are widespread Gram-negative, plant-protecting bacteria. However, in the art these particular strains (CHA0 and Pf-5) are also referred to as strains of *Pseudomonas fluorescens*. Thus, in some instances the bacterium is *Pseudomonas protegens*, particularly with reference to the strains CHA0 and Pf-5. In a further embodiment, the bacterium is a *Pseudomonas fluorescens* F113.

Cellulose

In some embodiments, the cellulose is bacterial cellulose. In some embodiments, the cellulose produced by the genetically modified microorganism or bacteria is secreted outside of the cell. Without being bound by theory, it is considered that bacterial cellulose has different properties from plant cellulose and is characterised by high purity, strength, moldability and increased water holding ability. It has been demonstrated that plant cellulose has a water retention value of around 60%, while bacterial cellulose has a water retention value of 1000% of the cellulose sample weight (Klemm, et al. 2001). In some embodiments, the secreted bacterial cellulose forms a network around the plant roots. In some embodiments, the bacterial cellulose network forms a spongy network. In some embodiments, the cellulose network is produced around plant roots.

It is anticipated that the network of bacterial cellulose produced by the genetically modified microorganism or bacteria of the invention will facilitate water management. Typically, the bacterial cellulose network retains water and provides an osmotic effect when water is required by the root. Moreover, the bacterial cellulose network may create an environment that increases the soil microbiome, delivering healthier soil and crops. Furthermore, the bacterial cellulose network may have the potential to prevent localised flooding from dramatic weather events. It is further anticipated that the bacterial cellulose network has the ability to act as a bio-scaffold to retain a greater quantity of nutrients around the root from the biofertiliser, and prevent run off of the fertiliser.

In some embodiments, the bacterial cellulose retains water. An increase in water retention is anticipated to result in an increase in crop viability and yield. In further embodiments, the bacterial cellulose facilitates a reduction in water evaporation. A reduction in water evaporation will reduce inefficient usage of water. Therefore, it is anticipated that the genetically modified microorganism or bacteria of the invention will increase the amount of water retained around a plant root system and as a result increase crop viability and yield in climates that have reduced rainfall and/or drought. In some embodiments, the genetically engineered microorganism, bacterium or root-associated bacterium is applied to a plant after planting but before harvest of said plant. In some embodiments, the genetically engineered microorganism, bacterium or root-associated bacterium is applied to the soil before planting a plant. In some embodiments, the genetically engineered microorganism, bacterium or root-associated bacterium is applied to the seed of a plant before planting.

The terms "increased cellulose production" and "increasing production of cellulose" are used herein to describe a greater amount of cellulose produced in a genetically engineered microorganism or bacterium compared to a reference microorganism or bacterium, respectively, optionally of the same strain or species. In some embodiments, the reference microorganism is a wild-type microorganism of the same strain or species. In some embodiments, the reference bacterium is a wild-type bacterium of the same strain or species. The increase in cellulose production may be 2-fold, 3-fold, 4-fold, 5-fold, 6-fold and so on, compared to a reference microorganism or bacterium. The quantity of cellulose produced by the genetically engineered microorganism or bacteria can be quantified by techniques that determine the weight of the dried and/or wet cellulose biomass. It is anticipated that the genetically engineered microorganism or bacterium of the invention will produce an increased dried and/or wet weight of cellulose biomass compared to a reference microorganism or bacterium, respectively. Bacterial cellulose may be quantified as described by Jozala A. F., et al. 2014 (which is incorporated by reference). For example, the bacterial cellulose can be collected, rinsed in distilled water, and immersed in NaOH 1 N at 60° C. for 90 min to remove attached cells. The bacterial cellulose may then be washed in distilled water and dried at 50° C. for 24 h to evaluate the bacterial cellulose yield concentration in mg mL-1 (mass (mg) of BC/volume (mL)) of culture medium).

Synthesis and Secretion of Cellulose

The synthesis of bacterial cellulose is a multistep process that involves two main mechanisms: the synthesis of uridine diphosphate (UDP-glucose), followed by the polymerisation of glucose into long and unbranched chains by cellulose synthase.

The proteins described herein are proteins that are involved in the synthesis and/or secretion of cellulose. In some embodiments, the microorganism or bacteria is modified to overexpress at least one, at least two, at least three, at least four, at least five, at least six, at least, seven, at least eight, at least nine, at least ten, at least eleven, or at least twelve of the proteins involved in synthesis and/or secretion of cellulose.

The bacterial cellulose biosynthesis (bcs) operon encoding a cellulose synthase complex for cellulose biosynthesis and secretion was initially identified in *Komagataeibacter xylinus* (also known as *Acetobacter xylinum* and *Gluconacetobacter xylinus*). In some embodiments, the microorganism or bacterium is genetically modified to overexpress at least one protein from a cellulose synthase complex. In some embodiments, the microorganism or bacteria is modified to overexpress at least one, at least two, at least three, or at least four of the proteins from a cellulose synthase complex.

*K. xylinus* has been identified as the most efficient bacterial cellulose producer among cellulose producer species. Specifically bacterial cellulose produced by *Komagataeibacter* species, displays unique properties, including high mechanical strength, high water absorption capacity, high crystallinity, and an ultra-fine and highly pure fibre network structure (Vandamme, et al. 1998). Without being bound by theory, it is anticipated that genetic modification of a microorganism, bacterium or root-associated bacteria with the cellulose synthesis proteins of *K. xylinus* will result in an increased and more efficient production of cellulose.

In some embodiments, the genetically engineered microorganism, bacterium or root-associated bacterium is genetically modified with an exogenous nucleic acid that encodes at least one protein from a bacterial cellulose synthase complex. In some embodiments, the genetically engineered microorganism, bacterium or root-associated bacterium is modified with at least one protein from a cellulose synthase complex from *K. xylinus*. For the purposes of the invention, the components of the cellulose synthase complex are described herein.

For the purposes of this invention, "a bcs operon" encodes four protein subunits BcsA, BcsB, BcsC, and BcsD that form a cellulose synthase complex. The BcsA subunit, located on the cytoplasmic face of the inner membrane possesses a catalytic β-1,4-glycosyltransferase domain responsible for polymerising monomers of uridine diphosphoglucose (UDP-glucose) into β-1,4-glucan chains of cellulose. The activity of the catalytic domain is regulated by the allosteric activator of bacterial cellulose synthesis, bis-(3'→5')-cyclic diguanylate. BcsB binds to BcsA in the periplasm by a single C-terminal transmembrane helix, where it stabilises BcsA and guides glucan chains through the periplasmic space using two carbohydrate-binding domains. Secretion of bacterial cellulose from the periplasm to the extracellular environment is believed to be facilitated through the action of BcsC, which is predicted to form a pore in the outer membrane of *K. xylinus* based on its structure. Consistent with the view that BcsC is an outer membrane porin, is the observation that BcsC is essential for in vivo, but not in vitro bacterial cellulose synthesis. Finally, crystallisation of bacterial cellulose is achieved through the action of BcsD, a cylindrical octameric periplasmic protein that contains four spiral channels that facilitates hydrogen bonding of four glucan chains during export through BcsC. Furthermore, it has been demonstrated in *K. xylinus* that BcsC mutants were unable to produce cellulose fibrils, whereas BcsD mutants produced ~40% less cellulose than the wild-type (Wong et al. 1990). Bacterial cellulose is distinguished from its plant equivalent by a high crystallinity index. Specifically, *K. xylinus* produces two crystalline allomorphs of bacterial cellulose known as cellulose I and cellulose II, which requires the cellulose synthase-associated BcsD subunit. This subunit has been characterised as coupling cellulose polymerisation and crystallisation.

In some embodiments, the genetically engineered microorganism, bacterium, or root-associated bacterium of the invention is modified to overexpress at least one of the genes bcsA, bcsB, bcsC, and bcsD. In some embodiments, the genetically engineered microorganism, bacterium, or root-associated bacterium of the invention is modified to overexpress a bcsA gene and a bcsB gene. In some embodiments, the genetically engineered microorganism, bacterium, or root-associated bacterium of the invention is modified to overexpress a bcsA gene and a bcsB gene, and at least one of a bcsC gene and a bcsD gene. In further embodiments, the genetically engineered microorganism, bacterium, or root-associated bacterium of the invention is modified to overexpress at least bcsA, bcsB and bcsD. In some embodiments, the genetically engineered microorganism, bacterium, or root-associated bacterium of the invention is modified to overexpress a bcs operon. In further embodiments, the bcsA, bcsB, bcsC, bcsD, and bcs operon are each isolated from *K. xylinus.* cmcAx (also known as bcsZ) is located upstream of the bcs operon and encodes endo-β-1,4-glucanase that has cellulose-hydrolysing ability. It has been demonstrated that in small amounts, exogenous CmcAx enhances bacterial cellulose production of *K. xylinus*, while endogenous overexpression of cmcAx increases bacterial cellulose yield. Without being bound by theory, it is anticipated that the cellulose hydrolysing activity of CmcAx may exert a regulatory effect on bacterial cellulose biosynthesis. In some embodiments, the genetically engineered microorganism, bacterium, or root-associated bacterium of the invention is modified to overexpress a cmcAx gene. In some embodiments, the microorganism is modified with a cmc gene. In further embodiments, the cmcAx gene is isolated from *K. xylinus.* ccpAx (also known as bcsH) is located in the same upstream operon as cmcAx, which encodes the cellulose-complementing protein (ccpAx) that is required for in vivo bacterial cellulose biosynthesis. CcpAx has been demonstrated to interact with BcsD in the periplasm. It is considered that this unique organisation might account for the extremely high activity of *K. xylinus*. In some embodiments, the genetically engineered microorganism, bacterium, or root-associated bacterium of the invention is modified to overexpress a ccpAx gene. In some embodiments, the microorganism is modified with a ccp gene. In further embodiments, the ccpAx gene is isolated from *K. xylinus.*

Downstream of the BC synthesis operon is bglAx (also known as bglxA) encoding β-glucosidase, which is secreted and has the ability to hydrolyse more than three β-1,4-glucose units (cellotriose). It has been demonstrated that whilst this enzyme is not essential for bacterial cellulose production, disruption of the bglAx gene causes a decrease in bacterial cellulose production (Tajima et al., 2001; Kawano et al., 2002). In some embodiments, the genetically engineered microorganism, bacterium, or root-associated bacterium of the invention is modified to overexpress a bglAx gene. In some embodiments, the microorganism is modified with a bgl gene. In further embodiments, the bglAx gene is isolated from *K. xylinus.*

Phosphoglucomutase, also referred to as celB, is responsible for catalysing the interconversion between glucose-1-phosphate (G-1-P) and glucose-6-phosphate (G-6-P). Without being bound by theory, it is thought that the conversion of G-6-P to G-1-P facilitates the production of cellulose. Phosphoglucomutase has been demonstrated to be essential in the formation of extracellular cellulose, as pgm mutants are unable to produce cellulose. In some embodiments, the genetically engineered microorganism, bacterium, or root-associated bacterium of the invention is modified to overexpress a pgm gene. In further embodiments, the pgm gene is isolated from *K. xylinus.*

UTP-glucose-1-phoshate is an enzyme involved in carbohydrate metabolism, and synthesises UDP-glucose from glucose-1-phosphate (G-1-P) and UTP. UDP-glucose is a key component in the production of cellulose. In some embodiments, the genetically engineered microorganism, bacterium, or root-associated bacterium of the invention is modified to overexpress a galU gene. In further embodiments, the galU gene is isolated from *K. xylinus.*

Diguanylate cyclase is an enzyme that catalyses 2 GTP into 2 diphosphate and cyclic GMP. This may be introduced into a bacterial cell as a gene dog or as the cdg operon. The cdg operon comprises cyclic di-GMP phosphodiesterase (pdeA) and diguanylate cyclase (dcg). Diguanylate cyclase, catalyses the formation of cyclic di-GMP and phosphodiesterase A catalyses the degradation. Without being bound by theory, cyclic di-GMP is considered to be an allosteric activator of bacterial cellulose synthesis. In some embodiments, the genetically engineered microorganism, bacterium, or root-associated bacterium of the invention is modified to overexpress a dcg gene and/or a cdg operon. In further embodiments, the dog gene and cdg operon are each isolated from *K. xylinus.*

In some embodiments, the genetically engineered microorganism, bacterium, or root-associated bacterium is modified to overexpress at least one or more genes selected from the group comprising: a bcsA gene; a bcsB gene; a bcsC gene; a bcsD gene; a cmcAx gene; a ccpAx gene; a bglAx gene; a pgm gene; a galU gene; a cdg operon; and a dgc gene.

In some embodiments the genetically engineered microorganism, bacterium, or root-associated bacterium is modified to overexpress the bcs operon and at least one of the following genes or operon:

a) cmcAx gene;
b) ccpAx gene;
c) bglAx gene;
d) pgm gene;
e) galU gene;
f) cdg operon; and/or
g) dgc gene.

In further embodiments, the genetically engineered microorganism, bacterium, or root-associated bacterium further comprises at least one, at least two, at least three, at least four, at least five, or at least six of the genes or operon as described by a) to g). In some embodiments, the genetically engineered microorganism, bacterium, or root-associated bacterium further comprises the genes and operon of a) to g). In some embodiments, the genetically engineered microorganism, bacterium, or root-associated bacterium further consists of the genes and operon of a) to g). In some embodiments, the genetically modified microorganism, bacterium, or root-associated bacteria of the invention comprise the bcs operon and at least the cmcAx gene, ccpAx gene, and bglAx gene. In some embodiments, the genetically modified microorganism, bacterium, or root-associated bacteria of the invention comprise the bcs operon and at least the cmc gene, ccp gene, and bgl gene. In some embodiments, the genetically modified microorganism, bacterium, or root-associated bacteria of the invention consist of the bcs operon and at least the cmcAx gene, ccpAx gene, and bglAx gene. In some embodiments, the genetically modified microorganism, bacterium, or root-associated bacteria of the invention consist of the bcs operon and at least the cmc gene, ccp gene, and bgl gene. In some embodiments, the genes are heterologous.

In some embodiments, a microorganism, bacterium, or root-associated bacterium comprising an endogenous bcs operon that does not comprise all of BcsA, BcsB, BcsC, and BcsD, may be modified with at least one of the genes of the bes operon (bcsA, bcsB, bcsC, bcsD). Typically, the bacterium would be modified with a bcs gene which is does not normally express. For example, *Pseudomonas fluorescens* SBW25 expresses only BcsA, BcsB and BcsC of the bcs operon, and thus according to the invention would be modified to express BcsD. In some embodiments, the root-associated bacteria *Pseudomonas fluorescens* SBW25 is modified with an exogenous nucleic acid that comprises bcsD.

Without being bound by theory, it is anticipated that the bcs operon and any combination of the cmcAx gene, ccpAx gene, bglAx gene, pgm gene, the galU gene, the dcg gene and/or the cdg operon will facilitate the synthesis and secretion of cellulose in the host bacterium. In some embodiments, the genetically engineered microorganism, bacterium, or root-associated bacterium of the invention may comprise multiple copies of any of the genes or operons described herein.

In some aspects, the invention relates to the incorporation of cellulose synthesising genes (preferably cmcAX, ccpAX, bcsA, bcsB, bcsC, bscD, and/or bglxA) into a foreign host present in the soil. In some aspects, the invention provides a microorganism genetically modified to overexpress at least one protein involved in synthesis and/or secretion of cellulose, wherein the genetically modified bacterium is modified with one or more heterologous genes, wherein the genes comprise a bcsA gene, a bcsB gene, a bcsC gene, and/or a bcsD gene. In some embodiments, the genes comprise a bcsA gene, a bcsB gene, a bcsC gene, and a bcsD gene. In some embodiments, the genes further comprise a cmcAx gene, a ccpAx gene, and/or a bglAx gene.

In some embodiments, the genetically modified bacterium is genetically modified with an exogenous nucleic acid comprising a bcs operon, wherein the bcs operon comprises a bcsA gene, a bcsB gene, a bcsC gene, and a bcsD gene. In some embodiments, the genetically modified bacterium is further modified with an exogenous nucleic acid comprising at least one of a cmcAx gene, a ccpAx gene, and a bglAx gene.

In some aspects, the invention provides a genetically engineered microorganism for producing cellulose, wherein the microorganism is genetically modified to overexpress at least one protein involved in synthesis and/or secretion of cellulose, wherein the genetically modified bacterium is modified to overexpress at least one or more exogenous genes, wherein the exogenous genes are selected from the group comprising: a bcsA gene, a bcsB gene, a bcsC gene, a bcsD gene, and optionally a copAx gene. In some embodiments, the microorganism is a bacterium, optionally a root-associated bacterium. In some aspects, provided is a genetically engineered microorganism, comprising one or more heterologous genes coding for production of cellulose, wherein the genes are bcsA, bcsB, bcsC and/or bcsD. In some embodiments, the genes are bcsA, bcsB, bcsC and bcsD. In some embodiments, the genes further comprise a cmcAx gene, a ccpAx gene, and/or a bglAx gene. In some embodiments, the microorganism is a bacterium. In further embodiments, the microorganism is a root-associated bacterium. In some embodiments, the genes are each isolated from *K. xylinus.*

In some embodiments, the genetically engineered microorganism further comprises a gene encoding green fluorescent protein (GFP). Without being bound by theory, providing a host cell that expresses GFP is considered to help with tracking the genetically modified microorganism, (e.g. bacteria) in the environment. Accordingly, in some embodiments, the genetically engineered microorganism, comprises one or more heterologous genes coding for production of cellulose, wherein the genes are bcsA, bcsB, bcsC and/or bcsD, and further comprises a gene encoding GFP.

Overexpression

The genetically engineered microorganism, bacterium, or root-associated bacterium of the invention is genetically modified to overexpress at least one protein involved in synthesis and/or secretion of cellulose. In some embodiments, the genetically engineered microorganism, bacterium, or root-associated bacterium of the invention is modified to overexpress at least one protein from a cellulose synthase complex.

The term "overexpression" as used herein is where the protein(s) of interest is expressed in the microorganism or bacterium at a higher level than the level at which it is expressed in a reference microorganism or reference bacterium, respectively, optionally a comparable wild-type microorganism or bacterium, respectively, typically of the same strain or species. Overexpression may include but is not limited to constitutive or induced expression. In some embodiments, the microorganism or bacterium does not endogenously express the protein(s) of interest, any level of expression of that protein in the microorganism or bacteria cell is deemed an "overexpression" of that protein for purposes of the present invention. In the present invention, the terms "overexpression of at least one protein involved in cellulose synthesis and/or secretion" or "overexpression at least one protein from a cellulose synthase complex", mean that the at least one of the proteins that are involved in the synthesis of cellulose is expressed in the microorganism or bacteria at a higher level than the level of which it is expressed in a comparable reference microorganism or bacterium, respectively. In some embodiments, the reference microorganism is a wild-type microorganism. In some embodiments, the reference microorganism is of the same species as the modified microorganism. The reference microorganism may be of the same strain as the modified microorganism. In some embodiments, the reference microorganism is a wild-type bacterium of the same strain or species as the modified microorganism. In some embodiments, the reference bacterium is a wild-type bacterium. In some embodiments, the reference bacterium is of the same species as the modified bacterium. The reference bacterium may be of the same strain as the modified bacterium. In some embodiments, the reference bacterium is a wild-type bacterium of the same strain or species as the modified bacterium.

Overexpression can be achieved in any way known to a skilled person in the art. In general, it can be achieved by increasing transcription/translation of the gene, e.g. by increasing the copy number of the gene or altering or modifying regulatory sequences or sites associated with expression of a gene. For example, overexpression can be achieved by introducing one or more copies of the polynucleotide encoding the gene of interest operably linked to regulatory sequences (e.g. a promoter). The gene may be operably linked to a strong constitutive promoter and/or strong ubiquitous promoter in order to reach high expression levels. Such promoters can be endogenous promoters or recombinant promoters. Alternatively, it is possible to remove regulatory sequences such that expression becomes constitutive. One can substitute the native promoter of a given gene with a heterologous promoter which increases expression of the gene or leads to constitutive expression of the gene. Typically, genome editing methods such as CRISPR, TALENs, and Zinc Finger Nucleases can be used according to the invention to achieve overexpression of cellulose synthesis and/or secretion proteins. For example, CRISPR genome editing may be used to remove regulatory sequence(s), resulting in constitutive expression of the gene of interest. Cellulose synthesis and/or secretion proteins (e.g. proteins of the cellulose synthase complex and its associated proteins) may be overexpressed by more than 10%, 20%, 30%, 40%, 50%, 60%, 70%, 80%, 90%, 100%, 200%, or more than 300% by the host cell compared to the host cell prior to engineering when cultured under the same conditions.

In one embodiment, overexpression of cellulose synthesis and secretion genes is achieved by altering or modifying regulatory sites associated with expression of a gene. In another embodiment, overexpression of cellulose synthesis and secretion genes is achieved by increasing the copy number of a cellulose synthesis and secretion gene. In a further embodiment, the microorganism, bacteria, or root-associated bacterium is modified with an exogenous nucleic acid comprising one or more cellulose synthesis and secretion genes. In some embodiments, the microorganism or bacteria are modified with one or more separate exogenous nucleic acids comprising one or more cellulose synthesis and secretion genes. In some embodiments, the exogenous nucleic acid is incorporated into a self-replicating plasmid within the microorganism or bacterium. In an alternative embodiment, the exogenous nucleic acid is incorporated into the genome of the microorganism or bacterium. In some embodiments, expression of the gene(s) of interest is transient. In some embodiments, expression of the gene(s) of interest is stable.

Detection of overexpression can be achieved in any way known to a skilled person in the art. Examples include, but are not limited to, detecting the proteins (machinery) for synthesis of cellulose e.g. cellulose synthase complex, by techniques such as Western Blot, qRT-PCT, and flow cytometry, or detecting the quantity of cellulose produced by the genetically engineered bacteria by techniques such as determining the weight of the dried and/or wet cellulose biomass.

In some embodiments, an exogenous nucleic acid is introduced into the microorganism, bacterium, or root-associated bacterium. In this specification, a nucleic acid may be any nucleic acid (DNA or RNA) having a nucleotide sequence having a specified degree of sequence identity to the genes of the bcs operon, a cmcAx gene; a ccpAx gene; a bglxA gene; a pgm gene; a galU gene; a cdg operon; and/or a dgc gene isolated from *K. xylinus* and to an RNA transcript of any one of these sequences, to a fragment of any one of the preceding sequences or to the complementary sequence of any one of these sequences or fragments. The specified degree of sequence identity may be from at least 60% to 100% sequence identity. More preferably, the specified degree of sequence identity may be one of at least 65%, 70%, 75%, 80%, 85%, 86%, 87%, 88%, 89%, 90%, 91%, 92%, 93%, 94%, 95%, 96%, 97%, 98% or 99% identity. In this specification, "an exogenous nucleic acid" refers to a nucleotide sequence that is foreign e.g. not endogenous to its host cell.

The term "endogenous" with reference to a polynucleotide or protein refers to a polynucleotide or protein that occurs naturally in the host cell.

The term "heterologous" with reference to a polynucleotide or protein refers to a polynucleotide or protein that does not naturally occur in the host cell. In preferred embodiments, the exogenous nucleic acid is a heterologous nucleic acid.

The term "recombinant," when used in reference to a subject cell, nucleic acid, protein or vector, indicates that the subject has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. The engineered microorganism or bacterium may be considered a recombinant microorganism or bacterium. In one embodiment, the microorganism or bacterial cells are genetically engineered by introducing an expression cassette or vector comprising an exogenous nucleic acid sequence encoding the machinery for cellulose synthesis and secretion e.g. cellulose synthase complex into said cells. The nucleic acid sequence may be operably linked to one or more control sequences that direct the expression of said nucleic acid in the microorganism or bacteria cells. The control sequence may include a promoter that is recognised by the microorganism or bacterial cell. The promoter contains transcription control sequences that mediate the expression of the machinery for the synthesis of cellulose. The promoter may be any polynucleotide that shows transcription activity in the microorganism or bacterial cells including mutant, truncated, and hybrid promoters. The promoter may be a constitutive or inducible promoter, preferably a constitutive promoter. The control sequence may also include appropriate transcription initiation, termination, and enhancer sequences. In some embodiments, the expression cassette comprises, or consists of, a nucleic acid sequence that encodes the machinery for cellulose synthesis and secretion operably linked to a transcriptional promoter and a transcription terminator.

A "vector" as used herein is an oligonucleotide molecule (DNA or RNA) used as a vehicle to transfer foreign genetic material into a cell. The vector may be an expression vector for expression of the foreign genetic material in the cell. Such vectors may include a promoter sequence operably linked to the nucleotide sequence encoding the gene sequence to be expressed. A vector may also include a termination codon and expression enhancers. Any suitable vectors, promoters, enhancers and termination codons known in the art may be according to the invention. Suitable vectors include plasmids, binary vectors, viral vectors and artificial chromosomes (e.g. yeast artificial chromosomes). In some embodiments, the vector of the invention is an isolated vector. An "expression cassette" as used herein is a distinct component of vector DNA consisting of a gene and regulatory sequence to be expressed in a host cell. An expression cassette typically comprises one or more genes and the sequences controlling their expression.

As used herein, a "constitutive promoter" is a promoter which is active under most conditions and/or during most development stages. There are several advantages to using constitutive promoters in expression vectors used in biotechnology, such as: high level of production of proteins used to select transgenic cells or organisms; high level of expression of reporter proteins or scorable markers, allowing easy detection and quantification; high level of production of a transcription factor that is part of a regulatory transcription system; production of compounds that requires ubiquitous activity in the organism; and production of compounds that are required during all stages of development. Alternatively, a non-constitutive promoter can be used. As used herein, a "non-constitutive promoter" is a promoter which is active under certain conditions. In embodiments, the promoter is an inducible promoter. In some embodiments, the inducible promoter is a sugar-induced promoter. In some embodiments, the promoter is an arabinose inducible promoter.

In preferred embodiments, the vector is a vector that when introduced into the microorganism or bacterial cell, is integrated into the genome and replicated together with the chromosome into which it has been integrated. In some embodiments, the integration of the genes encoding the machinery for cellulose synthesis will be integrated into the nonessential locus of a chromosome. A non-limiting example of a nonessential locus of a chromosome is locus-6-, on the 6.6 Mbp chromosome of SBW25 (Rainey and Bailey, 1996) using the methodology shown by BAILEY et al., 1995 (which is incorporated by reference). Typically, insertion of the gene(s) of interest is mediated by site-directed homologous recombination. In some embodiments, insertion of the gene of interest is mediated by CRISPR genome editing. Typically, a CRISPR knock-in is mediated by homologous directed repair (HDR). Without being bound by theory, it is anticipated that extra metabolic activity from expressing novel gene sequences and environmental variability are safeguards against uncontrolled genetically modified bacteria multiplication in the environment. For example, a microorganism or bacterium that produces increased amounts of cellulose may only survive in environments that support its multiplication, such as growing in and around a plant root. If the genetically modified microorganism or bacteria grow in an unfavourable environment, the extra metabolic burden of producing increased amounts of cellulose will lead to reduced viability of the genetically modified microorganism or bacteria in the wider environment, thereby improving the safety of the genetically modified microorganism or bacteria.

A counter selectable marker may be used in the expression system. An example of selectable markers include the sucrose sensitivity system wherein the vector encodes sacB. Examples of suitable vectors include, but are not limited to, recombinant integrating or non-integrating vectors. Examples of vectors include pGEX series of vectors, pET series of vectors, and the pEX series of vectors. In some embodiments, the pEX18Ap vector is used. In some embodiments, a mini CTX1 vector is used. In some embodiments, a pFLP2 vector is used. A pFLP2 is an excision vector that can be used to remove unwanted sequence. In some embodiments, the insertion site in the host microorganism is attb defined by SEQ ID NO: 1: TGAGTTCGAATCTCACCGCCTCCGCCATAT.

In this specification the term "operably linked" may include the situation where a selected nucleotide sequence and regulatory nucleotide sequence are covalently linked in such a way as to place the expression of a nucleotide coding sequence under the influence or control of the regulatory sequence. Thus a regulatory sequence is operably linked to a selected nucleotide sequence if the regulatory sequence is capable of effecting transcription of a nucleotide coding sequence which forms part or all of the selected nucleotide sequence. Where appropriate, the resulting transcript may then be translated into a desired protein or polypeptide.

In some embodiments, the microorganism according to the invention is modified with a cmcAx gene, having the nucleic acid sequence as defined by SEQ ID NO: 2.

In some embodiments, the microorganism is modified with a cmcAx gene, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 2.

In some embodiments, the microorganism according to the invention is modified with a ccpAx gene, having the nucleic acid sequence as defined by SEQ ID NO: 3.

In some embodiments, the microorganism is modified with a ccpAx gene, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 3.

In some embodiments, the microorganism according to the invention is modified with a bcs operon, comprising a bcsA gene, a bcsB gene, a bcsC gene and a bcsD gene, having the nucleic acid sequence as defined by SEQ ID NO: 4.

In some embodiments, the microorganism is modified with a bcs operon, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 4.

In some embodiments, the microorganism according to the invention is modified with a gfp gene having the nucleic acid sequence as defined by SEQ ID NO: 5.

In some embodiments, the microorganism is modified with a gfp gene, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 5.

In some embodiments, the microorganism according to the invention is modified with a bglAx gene having the nucleic acid sequence as defined by SEQ ID NO: 6.

In some embodiments, the microorganism is modified with a bglAx gene, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 6.

In some embodiments, the microorganism is modified with a cmcAx gene having at least 65% nucleic acid sequence identity to SEQ ID NO: 2, a ccpAx gene having at least 65% nucleic acid sequence identity to SEQ ID NO: 3, a bcs operon having at least 65% nucleic acid sequence identity to SEQ ID NO: 4, a gfp gene having at least 65% nucleic acid sequence identity to SEQ ID NO: 5, and/or a bglAx gene having at least 65% nucleic acid sequence identity to SEQ ID NO: 6.

In some embodiments, the microorganism according to the invention is modified with a PhlZ quorum sensing promoter having the nucleic acid sequence as defined by SEQ ID NO: 7.

In some embodiments, the microorganism is modified with a PhlZ quorum sensing promoter, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 7.

In some embodiments, the microorganism according to the invention is modified with a Rox quorum sensing promoter having the nucleic acid sequence as defined by SEQ ID NO: 8.

In some embodiments, the microorganism is modified with a Rox quorum sensing promoter, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 8.

In some embodiments, the microorganism according to the invention is modified with a AfmR quorum sensing promoter having the nucleic acid sequence as defined by SEQ ID NO: 9.

In some embodiments, the microorganism is modified with a AfmR quorum sensing promoter, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 9.

In some embodiments, the microorganism according to the invention is modified with a cmcAx gene having the nucleic acid sequence as defined by SEQ ID NO: 10.

In some embodiments, the microorganism is modified with a cmcAx gene, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 10.

In some embodiments, the microorganism according to the invention is modified with a ccpAx gene having the nucleic acid sequence as defined by SEQ ID NO: 11.

In some embodiments, the microorganism is modified with a ccpAx gene, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 11.

In some embodiments, the microorganism according to the invention is modified with a bcsA gene having the nucleic acid sequence as defined by SEQ ID NO: 12.

In some embodiments, the microorganism is modified with a bcsA gene, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 12.

In some embodiments, the microorganism according to the invention is modified with a bcsB gene having the nucleic acid sequence as defined by SEQ ID NO: 13.

In some embodiments, the microorganism is modified with a bcsB gene, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 13.

In some embodiments, the microorganism according to the invention is modified with a bcsC gene having the nucleic acid sequence as defined by SEQ ID NO: 14.

In some embodiments, the microorganism is modified with a bcsC gene, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 14.

In some embodiments, the microorganism according to the invention is modified with a bcsD gene having the nucleic acid sequence as defined by SEQ ID NO: 15.

In some embodiments, the microorganism is modified with a bcsD gene, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 15.

In some embodiments, the microorganism according to the invention is modified with a gfp gene having the nucleic acid sequence as defined by SEQ ID NO: 16.

In some embodiments, the microorganism is modified with a gfp gene, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 16.

In some embodiments, the microorganism according to the invention is modified with a bglAx gene having the nucleic acid sequence as defined by SEQ ID NO: 17.

In some embodiments, the microorganism is modified with a bglAx gene, having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 17.

In some embodiments, the microorganism is modified with a cmcAx gene having at least 65% nucleic acid sequence identity to SEQ ID NO: 10, a ccpAx gene having at least 65% nucleic acid sequence identity to SEQ ID NO: 11, a bcsA gene having at least 65% nucleic acid sequence identity to SEQ ID NO: 12, a bcsB gene having at least 65% nucleic acid sequence identity to SEQ ID NO: 13, a bcsC gene having at least 65% nucleic acid sequence identity to SEQ ID NO: 14, a bcsD gene having at least 65% nucleic acid sequence identity to SEQ ID NO: 15, a gfp gene having at least 65% nucleic acid sequence identity to SEQ ID NO: 16, and/or a bglAx gene having at least 65% nucleic acid sequence identity to SEQ ID NO: 17. In further embodiments, a promoter having at least 65% nucleic acid sequence identity to SEQ ID NO: 7, SEQ ID NO: 8 or SEQ ID NO: 9, is operably linked to a cmcAx gene having at least 65% nucleic acid sequence identity to SEQ ID NO: 10, a ccpAx gene having at least 65% nucleic acid sequence identity to SEQ ID NO: 11, a bcsA gene having at least 65% nucleic acid sequence identity to SEQ ID NO: 12, a bcsB gene having at least 65% nucleic acid sequence identity to SEQ ID NO: 13, a bcsC gene having at least 65% nucleic acid sequence identity to SEQ ID NO: 14, a bcsD gene having at least 65% nucleic acid sequence identity to SEQ ID NO: 15, a gfp gene having at least 65% nucleic acid sequence identity to SEQ ID NO: 16, and/or a bglAx gene having at least 65% nucleic acid sequence identity to SEQ ID NO: 17.

In some embodiments, the microorganism according to the invention is modified by SEQ ID NO: 18.

In some embodiments, the microorganism is modified with a nucleic acid having at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% nucleic acid sequence identity to SEQ ID NO: 18.

The above sequences can be combined and used in any order.

Quorum Sensing System

In some embodiments, expression of the cellulose synthesis genes is regulated by a cell-density quorum sensing promoter. In further embodiments, the expression of the cellulose synthesis genes is regulated by a cell-density quorum sensing system. In further embodiments, the quorum sensing system is under the control of a constitutive promoter. In further embodiments, the quorum sensing system regulates the promoter controlling expression of the genes disclosed herein. Without being bound by theory, it is anticipated that the use of a quorum sensing system controls the expression of the cellulose synthesis genes such that once the bacteria colonise the rhizosphere to a concentration threshold, the promoter is switched on and the cellulose synthesis will begin.

Quorum sensing (QS) is defined as the ability to detect and to respond to cell population density by gene regulation. As an example, bacteria can use quorum sensing to regulate phenotype expressions such as biofilm formation, virulence factor expression, motility, bioluminescence, nitrogen fixation, sporulation etc, which coordinate their behaviour. This function is based on the local density of the bacterial population in the immediate environment. In some embodiments, a quorum sensing operon is inserted into the host cell.

In some examples, gram-positive bacteria use the autoinducing peptide (AIP) as an autoinducer, which acts as a signalling molecule. When a high-concentration of AIP is detected in the local environment, the AIP binds to a receptor to active a kinase. The kinase then phosphorylates a transcription factor, which then regulates transcription of gene(s). This is known as a two-component system. Thus, in some embodiments, a two-component system is used. In some embodiments, a two-component system comprises a sensor kinase (which detects the signalling molecule) and a response regulator (which regulates gene expression).

In another example, gram-negative bacteria produce N-acyl homoserine lactones (AHL) as a signalling molecule. Typically, these AHLs bind directly to transcription factors to regulate gene expression. In some embodiments, a one-step process is used. It is known that some gram-negative bacteria also utilise a two-component system.

In some embodiments, the genes disclosed herein are regulated by a cell density-dependent auto-inducible promoter. In some embodiments, the cellulose synthesis and/or secretion genes disclosed herein are under the control of a cell-density quorum sensing promoter. It is anticipated that when the bacteria colonise the rhizosphere and reach a threshold density, the cellulose synthesising genes are switched on.

In some embodiments, the quorum sensing system comprises a gene encoding a sensor kinase and a gene encoding a response regulator. In further embodiments, the quorum sensing system further comprises a quorum sensing regulated promoter. In some embodiments, a nucleic acid comprising a gene encoding a sensor kinase and a gene encoding a response regulator is operably linked to a constitutive promoter. In further embodiments, a RoxS/RoxR quorum sensing system is used. In some embodiments, a RoxS/RoxR operon is inserted into the host cell. In alternative embodiments, the quorum sensing system comprises a gene encoding a signalling molecule (autoinducer) and a gene encoding a transcriptional/response regulator. In further embodiments, the quorum sensing system further comprises a quorum sensing regulated promoter. In some embodiments, a nucleic acid comprising a gene encoding a signalling molecule and a gene encoding a transcriptional/response regulator is operably linked to a constitutive promoter. In further embodiments, a PhzR/PhzI quorum sensing system is used. In some embodiments, a PhzR/PhzI operon is inserted into the host cell.

In some embodiments, the quorum sensing system activates the target gene promoter. In further embodiments, the response regulator binds to the target gene promoter.

QS-based auto-inducible promoter systems, specifically the RoxS/RoxR Quorum Sensing (QS) system of bacteria, is described in Meyers A, et al. 2019. The RoxS/RoxR quorum sensing system is a two-component system formed by a sensor histadine kinase (RoxS) and a response regulator (RoxR). It is anticipated that RoxS will result in the phosphorylation of RoxR, this phosphorylated RoxR will then regulate the expression of the cellulose synthesis and secretion genes disclosed herein, by binding to a putative RoxR recognition element. In some embodiments, a RoxS/RoxR quorum sensing system is used to control the expression of the cellulose synthesis and secretion genes. In some embodiments, a quorum sensing dependent RoxS/RoxR-promoter is used to control the expression of the cellulose synthesis and secretion genes. In some embodiments, a rox quorum sensing regulated promoter is used to control expression of the genes described herein. In some embodiments, a quorum sensing dependent RoxS/RosR-promoter is operably linked to a nucleic acid encoding the genes disclosed herein. In some embodiments, the promoter comprises a RoxR recognition element.

Also described is the PhzR/PhzI quorum sensing system. This system comprises the transcriptional regulator PhzR and the AHL synthase PhzI. In some embodiments, a PhzR/PhzI quorum sensing system is used to control the expression of the cellulose synthesis and secretion genes. In some embodiments, a quorum sensing dependent PhzR/PhzI-promoter is used to control the expression of the cellulose synthesis and secretion genes. In some embodiments, a phz quorum sensing regulated promoter is used to control expression of the genes described herein. In some embodiments, a quorum sensing dependent PhzR/PhzI-promoter is operably linked to a nucleic acid encoding the genes disclosed herein.

In further embodiments, the quorum sensing system is under the control of a constitutive promoter. This can be seen in FIGS. 4 and 5.

In some embodiments, a RhlR/RhlI quorum sensing system is used to control the expression of the cellulose synthesis and secretion genes. In some embodiments, a RhlR/RhlI operon is inserted into the host cell. In the RhlI/R system, rhlI directs the synthesis of N-(butanoyl)-homoserine lactone (C4-HSL), which then interacts with the cognate RhlR, influencing transcription of target genes. In some embodiments, a quorum sensing dependent RhlR/RhlI-promoter is used to control the expression of the cellulose synthesis and secretion genes. In some embodiments, a rhl quorum sensing regulated promoter is used to control expression of the genes described herein. In some embodiments, a quorum sensing dependent RhlR/RhlI-promoter is operably linked a nucleic acid encoding the genes disclosed herein.

In some embodiments, a LuxI/LuxR quorum sensing system is used to control the expression of the cellulose synthesis and secretion genes. In some embodiments, a LuxI/LuxR operon is inserted into the host cell. In some embodiments, a Lux/LuxR quorum sensing system is used to control the expression of the cellulose synthesis and secretion genes. In some embodiments, a quorum sensing dependent LuxI/LuxR-promoter is used to control the expression of the cellulose synthesis and secretion genes. In some embodiments, a lux quorum sensing regulated promoter is used to control expression of the genes described herein. In some embodiments, a quorum sensing dependent LuxI/LuxR-promoter is operably linked to a nucleic acid encoding the genes disclosed herein.

In some embodiments, a AfmI/AfmR quorum sensing system is used to control the expression of the cellulose synthesis and secretion genes. In some embodiments, a AfmI/AfmR operon is inserted into the host cell. In some embodiments, a AfmI/AfmR quorum sensing system is used to control the expression of the cellulose synthesis and secretion genes. In some embodiments, a quorum sensing dependent AfmI/AfmR-promoter is used to control the expression of the cellulose synthesis and secretion genes. In some embodiments, a afm quorum sensing regulated promoter is used to control expression of the genes described herein. In some embodiments, a quorum sensing dependent AfmI/AfmR-promoter is operably linked to a nucleic acid encoding the genes disclosed herein.

Without wishing to be bound by theory, the quorum sensing system acts as a biosafety element. The genetically engineered microorganisms of the invention are anticipated to colonise the rhizosphere environment of the plant of interest because the plant and bacterium live in a beneficial symbiotic relationship. In this biosafety system, the expression of cellulose may only be achieved when the concentration of bacteria is high. Therefore, when the genetically engineered microorganisms of the invention are not present in their optimal rhizosphere environment, the cellulose genes would not be expressed, and the genetically engineered microorganism would act as a wild-type strain.

In some embodiments, the heterologous cellulose synthesis and/or secretion genes are regulated by a quorum sensing system. In some embodiments, the heterologous cellulose synthesis and/or secretion genes are regulated by a quorum sensing regulated promoter.

In some embodiments, the quorum sensing system regulated promoter is operably linked to the nucleic acid encoding one or more of the exogenous genes of the invention, wherein expression of said genes is regulated by the quorum sensing system. In some embodiments, the exogenous genes comprise a bcsA gene; a bcsB gene; a bcsC gene; a bcsD gene; a cmc gene; a ccp gene; a bgl gene; a pgm gene; a galU gene; a cdg operon; and a dgc gene. In further embodiments, the genes a heterologous.

Compositions

In some embodiments, the genetically modified microorganism of the invention is delivered to plants as an inoculum that can be directly added to the soil. In some embodiments, the genetically modified bacterium of the invention is delivered to plants as a bacterial inoculum that can be directly added to the soil. In another embodiment, the genetically modified microorganism or bacterium of the invention is delivered to plants as a liquid formulation that can be directly added to the soil. In some embodiments, the microbial or bacterial inoculants are peat-based formulations. In further embodiments, the peat-based formulations are used to coat seeds or pellets for sowing in furrows. In some embodiments, the genetically modified microorganism or bacterium of the invention is delivered to plants in microbeads. In further embodiments, the microbeads are alginate microbeads. It is anticipated that these alginate microbeads encapsulate the microorganisms or bacteria and protect them against environmental stresses and release them into the soil gradually when soil microorganisms degrade the polymers.

Typically, the genetically modified microorganism or bacteria of the invention can be applied in combination with biofertilisers. A "biofertiliser" as used herein is a substance which contains living microorganisms which promotes plant growth by increasing the supply availability of primary nutrients to the host plant. Biofertilisers may add nutrients to the plant by nitrogen fixations, solubilising phosphorous, and stimulating plant growth through the synthesis of growth-promoting substances. Biofertilisers do not contain any chemicals which are harmful to the living soil. Examples include, *Rhizobium, Azotobacter, Azospirilium* and blue green algae (BGA). Additional examples include strains such as *Pantoea agglomerans* strain P5 or *Pseudomonas putida* strain P13, which are known in the art to solubilise phosphate from organic or inorganic phosphate sources. It is anticipated that the genetically modified microorganisms or bacteria of the invention can be used in combination with such biofertilisers. In some embodiments, the genetically modified microorganism or bacteria of the invention may administered to the soil in combination with a biofertiliser in a single composition. In some embodiments, the genetically modified microorganisms or bacteria of the invention may administered to the soil in combination with more than one biofertiliser in a single composition. In another embodiment, the genetically modified microorganisms or bacteria of the invention are administered separately to the biofertiliser/biofertilisers.

In some embodiments, the genetically modified microorganisms or bacterium of the invention is delivered to plants in combination with a fertiliser in a single composition. In some embodiments, the genetically modified microorganism or bacterium of the invention is delivered to plants in combination with more than one fertiliser in a single composition. In another embodiment, the genetically modified microorganism or bacterium of the invention is administered separately to the fertiliser/fertilisers. As used herein a "fertiliser" is any material of natural or synthetic origin that are used to improve plant growth and yield.

In some embodiments, the composition of the invention is delivered to plants in microbeads. In further embodiments, the microbeads are alginate microbeads. Typically, alginate is the most common polymer material for the encapsulation of microorganisms for various industrial microbiological purposes, but other algal polysaccharides may be used (Bashan, Y., et al. 2002). The main advantages associated with alginate preparations are their non-toxic nature (reducing the impact to the local environment), degradation in the soil, their slow release of bacteria into the soil, and almost unlimited shelf life (Bashan Y et al. 2002). In some embodiments, the microbeads are applied as wet microbeads. In some embodiments, the microbeads are applied as dry microbeads. In some embodiments, the microbeads are between 100 μm and 500 μm in diameter. In a preferred embodiment, the microbeads are between 100 μm and 200 μm in diameter. It is anticipated that a microbead of between 100 μm and 500 μm in diameter will be able to hold >$10^6$ CFU bead-1, which is sufficient to inoculate a seed. In some embodiments, the composition of the invention is delivered to plants as macrobeads. In further embodiments, the macrobeads are alginate macrobeads. It is anticipated that the alginate macrobeads behave in a similar manner to microbeads. In some embodiments, the macrobeads are between 1 mm and 5 mm in diameter. In a further embodiment, the macrobeads are between 1 mm and 3 mm in diameter.

In some embodiments, the microbial or bacterial composition is applied to a plant after planting but before harvest of said plant. In some embodiments, the microbial or bacterial composition is applied to the soil before planting a plant. In some embodiments, the plant is a crop plant. In some embodiments, the composition is used to coat seeds or pellets for sowing in furrows.

Without being bound by theory, it is anticipated that the genetically engineered microorganism, bacterium, or root-associated bacterium according to the invention will colonise the roots of plants following inoculation onto seeds and result in enhanced plant growth. The following steps outline the colonisation process: a) inoculation onto seed, b) multiplication in the spermosphere (region surrounding the seed) in response to seed exudates, c) attachment to the root surface, and d) colonisation of the developing root system.

In some embodiments, the microorganisms or bacteria are stored as a dried formula and delivered to soil as a liquid broth.

Methods

In one aspect of the invention, a method of increasing water-retention around plant roots is provided. The method comprising applying the genetically engineered microorganism, bacteria, or root-associated bacteria of the invention to the surrounding soil of the plant. In some embodiments, water-retention around plant roots is increased relative to the same plant(s) in the same conditions but without the microorganism of the invention. In some embodiments, the increase in water-retention can be measured by an increase in soil water content. Soil water content can be calculated on a gravimetric or volumetric basis. For example, gravimetric water content (θg) is the mass of dry soil, and is measured by weighing a soil sample ($m_{wet}$), drying the sample to remove the water, then weighing the dried soil sample ($m_{dry}$) using the following equation:

$$\theta g = \frac{m_{water}}{m_{soil}} = \frac{m_{wet} - m_{dry}}{m_{dry}}$$

Alternatively, soil water content can be measured by volumetric water content (θv), which is the volume of liquid water per volume of soil. Volume is the ratio of mass to density (ρ), and can be calculated using the following equation:

$$\theta v = \frac{\text{volume}_{water}}{\text{volume}_{soil}} = \frac{\frac{m_{water}}{\rho_{water}}}{\frac{m_{soil}}{\rho_{soil}}} = \frac{\theta_g^* \rho_{soil}}{\rho_{water}}$$

In some embodiments, the soil water content is increased at least 2-fold, 3-fold, 4-fold, 5-fold, 6-fold and so on.

Another aspect of the invention provides a method of reducing water consumption in agriculture, comprising applying the genetically engineered microorganism, bacterium, or root-associated bacteria of the invention to the surrounding soil of the plant. In some embodiments, the reduction in water consumption in agriculture is reduced relative to the same plant(s) in the same conditions but without the microorganism of the invention. In some embodiments, the amount of water used in agriculture is reduced by at least 10%, 20%, 30%, 40%, 50%, 60%, 70%, 80%, 90%, and so on.

Plants

It is anticipated that the genetically modified microorganism or bacteria of the invention will increase the amount of water retained around a plant root system and as a result increase crop viability and yield in climates that have reduced rainfall and/or drought. The increase in water retained is relative to the same plant in the same conditions (e.g. soil) without the bacteria of the invention.

In some embodiments of the invention, the plant is a cereal plant, a corn plant, a rice plant, a wheat plant, a soy plant, a sugarcane plant, a maize plant, a potato plant, a tomato plant, tobacco plant, and a cassava plant. In further embodiments, the plant is a cereal plant, a corn plant, a rice plant, a wheat plant, or a soy plant.

An aspect of the invention provides a plant comprising the genetically engineered microorganism, bacterium, or root-associated bacteria of the invention. In some embodiments, the plant comprises the isolated genetically engineered root-associated bacterium of the invention, the population of genetically engineered root-associated bacteria of the invention, or the bacterial composition of the invention. In some embodiments, the genetically engineered root-associated bacterium, isolated genetically engineered root-associated bacterium, or the population of genetically engineered root-associated bacteria is associated with the plant roots. In some embodiments, the genetically engineered root-associated bacterium grows on the plant roots. In some embodiments, the genetically engineered microorganism, bacterium, or root-associated bacterium grows in the soil surrounding plant roots.

Carbon Capture

The invention provides a method of capturing carbon, comprising applying a genetically engineered microorganism to soil surrounding a plant root, wherein the microorganism is genetically modified to overexpress at least one protein involved in synthesis and/or secretion of cellulose, and wherein the carbon is converted to cellulose by the microorganism.

In some embodiments, the genetically engineered microorganism is a microorganism according to the invention, an isolated genetically engineered microorganism of the invention, a population of genetically engineered microorganisms of the invention, or a composition of the invention.

In some embodiments, the carbon is absorbed as carbohydrates secreted from a plant and the carbohydrates are converted into cellulose by the microorganism. In some embodiments, production of cellulose results in increased water-retention around plant roots.

In some embodiments, the genetically engineered microorganism is selected from a bacterial cell, a fungal cell or an algae cell. In some embodiments the genetically engineered microorganism is a bacterium. In further embodiments, the genetically engineered microorganism is a root-associated bacterium.

The genetically engineered microorganism, bacterium or root-associated bacterium according to the invention excretes carbon-rich cellulose around plant roots. Besides storing large volumes of water, this secreted cellulose also sequesters a considerable amount of carbon, as explained below.

During the synthetic process, the glucose chains produced inside the microorganism or bacterial body extrude out through tiny pores present on their cell envelope. The glucose chains then form microfibrils that further aggregate to form cellulose ribbons. These ribbons generate a web-shaped network structure with plenty of empty spaces between the fibers. The well-separated nanofibrils of bacterial cellulose create an expanded surface area and highly porous matrix. The basic fibril structure consists of a β-1→4 glucan chain with the following molecular formula: $(C6H10O5)n$. The chains are held together by hydrogen bonds. Bacterial cellulose microfibrils are approximately 100-fold smaller than the fibrils of vegetal. The fibrous network of bacterial cellulose consists of well-arranged, three-dimensional nanofibers resulting in the formation of hydrogel film with a large surface area and considerable porosity. As it is not associated with lignin or hemicelluloses as in vegetal cellulose, bacterial cellulose is purer. Moreover, the three-dimensional nanofibril network has a high-water absorption capacity and tensile strength.

It is known that during plant photosynthesis atmospheric carbon dioxide is absorbed and converted to carbohydrates. These carbohydrates are then excreted in the exudate of the root. Such carbohydrates include many sugars comprising glucose, fructose, arabinose and others. These carbohydrates are considered to be essential as carbon sources for microbial life in the soil, driving cellular proliferation and growth. It is considered that roughly 30% of the sugars produced in a plant are secreted into the surrounding soil, which feeds the plant microbiome.

Natural bacteria found in the soil surrounding the plant does not provide a substantial sequestration event to slow/reduce climate change.

The inventor has surprisingly found that the genetically engineered microorganism, bacterium and/or root-associated bacteria according to the invention use this excreted glucose to grow, but also they are advantageously engineered to metabolise these sugars and excrete them as bacterial cellulose. Cellulose is composed of glucose molecules structurally formed with β-1,4-glycosidic bonds and intramolecular hydrogen bonds. This trapped carbon in the soil surrounding plant roots directly results in increased plant health (for example, by retaining water around plant roots). As a result, plants are able to absorb more carbon dioxide and the cycle goes on. As bacterial cellulose is able to degrade over a period of months, the sequestration of carbon can then be used by plants and microbes to grow stronger, maintaining the carbon in the soil. This will form a cyclical event that never escapes the soil.

In some embodiments, the increase in cellulose production results in increased plant viability. It is anticipated that this increase in plant viability results in increased atmospheric carbon capture by the plant and generation of sugars, which are converted to cellulose, thereby sequestering the carbon in the soil.

In some embodiments, cellulose production by the microorganism or bacterium results in increased carbon sequestration in the surrounding soil. In some embodiments, the carbon captured is increased at least 2-fold, 3-fold, 4-fold, 5-fold, 6-fold and so on. The increase in carbon captured is relative to the same plant(s) in the same conditions, but without the microorganism of the invention. In some embodiments, the carbon is atmospheric carbon.

In some embodiments, the carbohydrate secreted from a plant is a sugar. In further embodiments, the sugar is glucose, fructose, and/or arabinose.

Uses

In some aspects, the invention provides use of a genetically modified microorganism in agriculture, wherein the microorganism is genetically modified to overexpress at least one protein involved in synthesis and/or secretion of cellulose.

In another aspect, the invention provides use of a genetically modified microorganism to increase water-retention around plant roots, wherein the microorganism is genetically modified to overexpress at least one protein involved in synthesis and/or secretion of cellulose.

In another aspect, the invention provides use of a genetically modified microorganism in carbon capture, wherein the microorganism is genetically modified to overexpress at least one protein involved in synthesis and/or secretion of cellulose, and wherein the carbon is converted into cellulose by the microorganism.

In some embodiments, the genetically engineered microorganism is a microorganism according to the invention, an isolated genetically engineered microorganism of the invention, a population of genetically engineered microorganisms of the invention, or a composition of the invention.

In some embodiments, the genetically engineered microorganism is selected from a bacterial cell, a fungal cell or an algae cell. In some embodiments the genetically engineered microorganism is a bacterium. In further embodiments, the genetically engineered microorganism is a root-associated bacterium.

In some embodiments, the microorganism is genetically modified to overexpress at least one protein involved in synthesis and/or secretion of cellulose, wherein the genetically modified bacterium is modified with an exogenous nucleic acid comprising a bcs operon, wherein the bcs operon comprises a bcsA gene, a bcsB gene, a bcsC gene, and a bcsD gene. In further embodiments, the exogenous nucleic acid further comprises a ccpAx gene. In some embodiments, the exogenous nucleic acid further comprises a cmcAx gene, a ccpAx gene, and a bglAx gene. In further embodiments, the genes are heterologous.

In some embodiments, the microorganism is genetically modified one or more heterologous genes, wherein the genes are selected from: a bcsA gene, a bcsB gene, a bcsC gene, a bcsD gene, a cmcAx gene, a ccpAx gene, and a bglAx gene. In some embodiments, the genes are each isolated from *K. xylinus*. In some embodiments, the genetically engineered microorganism is a bacterium, optionally a root-associated bacterium. In some embodiments, the genetically engineered microorganism is a plant growth-promoting rhizobacterium.

The features disclosed in the foregoing description, or in the following numbered embodiments or claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word “comprise” and “include”, and variations such as “comprises”, “comprising”, and “including” will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example+/−10%.

NUMBERED EMBODIMENTS

1. A genetically engineered microorganism for producing cellulose, wherein the microorganism is genetically modified to overexpress at least one protein involved in synthesis and/or secretion of cellulose.
2. The genetically engineered microorganism of embodiment 1, wherein the cellulose is bacterial cellulose.
3. The genetically engineered microorganism of embodiment 1 or embodiment 2, wherein cellulose production is increased in the genetically modified microorganism compared to a reference microorganism.
4. The genetically engineered microorganism according to any one of the preceding embodiments, wherein the genetically modified microorganism is modified with an exogenous nucleic acid encoding at least one protein from a cellulose synthase complex.
5. The genetically engineered microorganism according to any one of the preceding embodiments, wherein exogenous nucleic acid comprises a bcs operon.
6. The genetically engineered microorganism according to embodiment 5, wherein the exogenous nucleic acid further comprises at least one of the following genes or operon:
   a) cmcAx gene;
   b) ccpAx gene;
   c) bglAx gene;
   d) pgm gene;
   e) galU gene;
   f) cdg operon; and/or
   g) dgc gene.
7. The genetically engineered microorganism according to embodiment 5, wherein the exogenous nucleic acid further comprises a cmcAx gene, a ccpAx gene, and a bglAx gene.
8. The genetically engineered microorganism according to any one of embodiments 5 to 7, wherein the bcs operon, cmcAx gene, ccpAx gene, bglAx gene, pgm gene, galU gene, cdg operon, and/or dgc gene are each isolated from *K. xylinus*.
9. The genetically engineered microorganism according to any one of the preceding embodiments, wherein the microorganism is a bacterium, optionally wherein the microorganism is *Pseudomonas fluorescens*.
10. The genetically engineered microorganism according to any one of the preceding embodiments, wherein the cellulose is secreted outside of the cell.
11. The genetically engineered microorganism according to embodiments 10, wherein the secreted cellulose forms a network outside of the cell.
12. The genetically engineered microorganism according to embodiments 11, wherein the secreted cellulose network increases water retention around plant roots.
13. The genetically engineered microorganism according to embodiments 12, wherein the plant is a cereal plant, a corn plant, a rice plant, a wheat plant, or a soy plant.
14. A method of increasing production of cellulose in a microorganism compared to a reference microorganism, wherein the method comprises a step of modifying the microorganism to overexpress at least one protein involved in synthesis and/or secretion of cellulose.
15. The method of increasing production of cellulose according to embodiments 14, wherein the microorganism is modified with an exogenous nucleic acid encoding at least one protein from a cellulose synthase complex.
16. A vector comprising an exogenous nucleic acid that comprises a bcs operon and at least one of a cmcAx gene, a ccpAx gene, a bglAx gene, a pgm gene, a galU gene, a cdg operon, and a dgc gene.
17. A method of producing a genetically engineered microorganism for producing cellulose, wherein the method comprises a step of modifying the microorganism to overexpress at least one protein involved in synthesis and/or secretion of cellulose comprising:
   a) isolating a microorganism; and
   b) introducing a vector comprising an exogenous nucleic acid comprising at least one of the genes selected from the group comprising: a bcsA gene; a bcsB gene; a bcsC gene; a bcsD gene; a cmcAx gene; a ccpAx gene; a bglAx gene; a pgm gene; a galU gene; a cdg operon; and a dgc gene, into the microorganism.
18. A genetically engineered microorganism obtainable by the method of embodiment 17.
19. An isolated genetically engineered microorganism according to any one of embodiments 1 to 13 or embodiment 18.
20. A population comprising the genetically engineered microorganism according to any one of embodiments 1 to 13 or embodiment 18.
21. A composition comprising the genetically engineered population of embodiment 20.
22. The composition according to embodiment 21, wherein the composition further comprises a fertiliser and/or a biofertiliser.
23. A method of increasing water-retention around plant roots, comprising applying a genetically engineered microorganism to soil surrounding a plant root, wherein the microorganism is genetically modified to overexpress at least one protein involved in synthesis and/or secretion of cellulose.
24. The method according to embodiment 23, wherein the microorganism is selected from the genetically engineered microorganism according to any one of embodiments 1 to 13 or embodiment 18, the isolated genetically engineered microorganism of embodiment 19, the population of genetically engineered microorganisms of embodiment 20, or the composition of embodiments 21 or 22.
25. A method of reducing water consumption in agriculture, comprising applying a genetically engineered microorganism to soil surrounding a plant root, wherein the microorganism is genetically modified to overexpress at least one protein involved in synthesis and/or secretion of cellulose.

26. The method according to embodiment 25, wherein the microorganism is selected from the genetically engineered microorganism according to any one of embodiments 1 to 13 or embodiment 18, the isolated genetically engineered microorganism of embodiment 19, the population of genetically engineered microorganisms of embodiment 20, or the composition of embodiments 21 or 22.
27. A plant comprising the genetically engineered microorganism according to any one of embodiments 1 to 13 or embodiment 18, the isolated genetically engineered microorganism of embodiment 19, the population of genetically engineered microorganisms of embodiment 20, or the composition of embodiments 21 or 22, wherein the genetically engineered microorganism, isolated genetically engineered microorganism, or the population of genetically engineered microorganisms is associated with the plant roots.
28. A method of capturing carbon, comprising applying a genetically engineered microorganism to soil surrounding a plant root, wherein the microorganism is genetically modified to overexpress at least one protein involved in synthesis and/or secretion of cellulose, and wherein the carbon is converted to cellulose by the microorganism.
29. The method according to embodiment 28, wherein the genetically engineered microorganism is a microorganism according to any one of embodiments 1 to 13 or embodiment 18, an isolated genetically engineered microorganism of embodiment 19, a population of genetically engineered microorganisms of embodiment 20, or a composition of embodiments 21 or 22.
30. The method according to embodiment 28 or embodiment 29, wherein the carbon is absorbed as carbohydrates secreted from a plant and the carbohydrates are converted into cellulose by the microorganism.
31. The method according to any one of embodiments 28 to 30, wherein production of cellulose results in increased water-retention around plant roots.
32. Use of a genetically modified microorganism in agriculture, wherein the microorganism is genetically modified to overexpress at least one protein involved in synthesis and/or secretion of cellulose.
33. Use of a genetically modified microorganism to increase water-retention around plant roots, wherein the microorganism is genetically modified to overexpress at least one protein involved in synthesis and/or secretion of cellulose.
34. Use of a genetically modified microorganism in carbon capture, wherein the microorganism is genetically modified to overexpress at least one protein involved in synthesis and/or secretion of cellulose, and wherein the carbon is converted into cellulose by the microorganism.

EXAMPLES

Example 1—Engineering of the Root-Associated Bacteria

1. Bacterial Strains and Plasmids

*Komagataeibacter xylinus* DSM 2325 will be obtained from DSMZ (Braunschweig, Germany). Exemplary bacterial strains and plasmids are listed in Table 1.

*K. xylinus* is a member of the acetic acid bacteria, a group of Gram-negative aerobic bacteria that produce acetic acid during fermentation. *K. xylinus* is unusual among the group in also producing cellulose.

2. Gene Manipulation

For genetic manipulation purposes, *E. coli* TOP10 cells will be used. *E. coli* cells will be cultivated in Luria-Bertani (LB) medium (Invitrogen, Carlsbad, CA) at 37° C. with 225 rpm orbital shaking. LB will be supplemented with antibiotics (50 μg/ml ampicillin) when needed for plasmid maintenance. All DNA manipulations will be conducted according to standard protocols (Sambrook, J., 2001).

*Pseudomonas fluorescens* strain SBW25 (Rainey and Bailey, 1996), will be utilised as a host for insertion of the bacterial biosynthetic cellulose machinery. A nonessential locus-6-, on the 6.6-Mbp chromosome of SBW25 will be chosen, as previously demonstrated (Rainey and Bailey, 1996) and the methodology shown by (BAILEY et al., 1995). Two fragments flanking the -6-locus (~200 bp) will be amplified by conducting PCR with *P. fluorescens* genomic DNA; the genomic DNA will be prepared using genomic DNA extraction kit from Promega (Madison, WI). The upstream and downstream flanking fragment will be amplified by PCR. The upstream and downstream regions of the -6-locus, bcs operon, pgm (phosphoglucomutase), galU (UTP-glucose-1-phosphate), cdg operon, and dgc standalone gene (Table 2.) from *K. xylinus* (Jang et al., 2019) will be ligated into the pEX18Ap vector at the EcoRI restriction enzyme site using the In-fusion HD cloning kit (Clontech laboratories, Inc., mountain view, CA), resulting in the pEX-bcs vector. This plasmid will be transformed into *E. coli* TOP10 cells for the amplification and identification of the modified pEX-bcs plasmid. The purified plasmid will then be introduced into the -6-locus chromosomal site in *P. fluorescens* by electroporation, for the expression of the bcs bacterial biosynthetic cellulose machinery.

3. Growth Conditions of Engineered Strains

The following conditions will be used for the visual verification of the successful bacterial biosynthetic cellulose machinery expression into *P. fluorescens*. Following this, greenhouse and field trials will be used for the optimisation of cellulose production in a model system. Nutrient broth media will be used for all cellulose synthesis production experiments using flasks containing: 3.0 g/L meat extract, 10.0 g/L peptone (enzymatic digest of casein), 5.0 g/L sodium chloride, pH 7. Cells will be incubated for 5 days at 30° C. under static conditions. The media will be supplemented with various carbohydrates for optimisation. Routine experimental optimisation of this protocol can be performed to adjust the specific parameters for best results according to particular field conditions.

TABLE 1

Description of the bacterial species and plasmids.

| Species or plasmids | Description | Reference |
|---|---|---|
| *Komagataeibacter xylinus* DSM 2325 | *Komagataeibacter xylinus* is a model organism for the production of bacterial cellulose. | (Jang et al., 2019) |

TABLE 1-continued

Description of the bacterial species and plasmids.

| Species or plasmids | Description | Reference |
|---|---|---|
| *Pseudomonas fluorescens* SBW25 | *Pseudomonas fluorescens* encompasses a diverse group of bacteria which are capable of colonizing a variety of ecological niches, including soil, water, and the surfaces and tissues of many living organisms (both plants and animals) | (Rainey and Bailey, 1996) |
| One Shot TOP10 Chemically Competent *E. coli* | Allow for high-efficiency cloning and plasmid propagation, including stable replication of high-copy number plasmids. | (Walz et al., 2002) |
| pEX18Ap | A broad-host-range recombination system for site-specific excision of chromosomally-located DNA sequences | (Baynham et al., 2006) |

TABLE 2

Description of the genes essential for biosynthetic cellulose synthesis production in *Komagataeibacter xylinus* that will be used for the genetic modification in *Pseudomonas fluorescens*.

| Genes | Description | Reference |
|---|---|---|
| bes operon (bcsA, bcsB, bcsC, bcsD) | bcs genes that encode the components of the cellulose biosynthesis and secretion machinery. | (Wong et al., 1990) |
| cmcAx (bcsZ) | Encodes an endo-β-1,4-glucanase | (Kawano et al., 2002) |
| ccpAx (bcsH) | Cellulose complementing protein | (Standal et 5 al., 1994) |
| bglAx | Encodes a β-glucosidase | (Tajima et al., 2001) |
| Pgm (celb) | Phosphoglucomutase | (Brautaset et al., 1994) |
| galU | UTP-glucose-1-phosphate | (Koo et al., 2000) |
| cdg operon (pdeA, dgc) | Diguanylate cyclase (DGC), catalyses its formation of cyclic di-GMP and phosphodiesterase A (pdeA) catalyses the degradation. | (Ryngajłło et al., 2019) |
| Standalone dgc gene | Diguanylate cyclase (DGC), catalyses its formation of cyclic di-GMP | (Bae et al., 2004) |

Example 2—Application of the Genetically Modified Bacteria

The genetically modified bacteria will be delivered in biodegradable microbeads (microballs) containing a nutrient source which will be supplemented in currently commercially available biofertilisers.

In this example a method of inoculating plants (or seeds) with the genetically modified bacterium of the invention is described using alginate microbeads. These alginate microbeads encapsulate the bacteria and protect them against environmental stresses and release them into the soil gradually when soil microorganisms degrade the polymers. The raw material, kelp macroalga (Macrocystis pyrifera), is a renewable marine resource of great abundance in the Pacific Ocean.

1. Microbead Formation

The microbeads may be produced using a device as described in Bashan et al. 2002, or any other suitable device. Typically, the microbeads produced will be around 100 to 200 μm in diameter. The bacteria of the invention will be cultured as described above and then the bacterial suspension will be mixed with 2% sodium alginate (CICIMAR, La Paz, Mexico), optionally skim milk without Ca may also be added to the alginate-bacterial suspension to produce beads that are more biodegradable. This suspension will then be pressurised at 10-15 psi using a commercial air compressor. Then the bacterial suspension will be forced to pass through a 222-μm-daimeter capillary exit, which will create a fine spray of miniature droplets. The mist will then be collected using a stainless steel flask rotating at 40 rpm containing 0.1M $CaCl_2$) to solidify the microbeads. The microbeads will then be allowed to cure in $CaCl_2$) solution for 30 mins. The wet microbeads will then be extracted from the $CaCl_2$) solution, and then rinsed in 500 ml saline solution (0.85% (w/v) NaCl) four times under aseptic conditions. Optionally the microbeads can be transferred into bacterial culture medium (in growth conditions) to allow for bacterial multiplication. The microbeads will then be separated from the suspension by filtration using Whatman filter paper, and rinsed three times with 500 ml saline solution.

2. Drying Procedures

Optionally, the microbeads may be dried before applying them to soil, plant roots, and/or seeds. In this drying method, 10 g of microbeads can be placed as a thin layer on filter paper in a Petri dish and dried at 38±1° C. for 48 h. Then the dry microbeads can be collected in a hermetically sealed container with silica gel until they are used. Alternatively, dry microbeads may be prepared by standard lyophilisation.

The wet and/or dry microbeads comprising the genetically modified root-associated bacteria will then be applied to the soil, plant roots, and/or seeds.

Example 3—Engineering of the Root-Associated Bacteria

1. Bacterial Strains and Plasmids

This method will use the *Komagataeibacter xylinus* CGMCC 2955 strain and the Mini CTX1 vector and the pFLP2 excision vector to remove unwanted sequences.

2. Gene Manipulation

As before, for genetic manipulation purposes, *E. coli* TOP10 cells will be used. *E. coli* cells will be cultivated in Luria-Bertani (LB) medium (Invitrogen, Carlsbad, CA) at 37° C. with 225 rpm orbital shaking. LB will be supplemented with antibiotics (50 μg/ml ampicillin) when needed for plasmid maintenance. All DNA manipulations will be conducted according to standard protocols (Sambrook, J., 2001).

Figure 3:
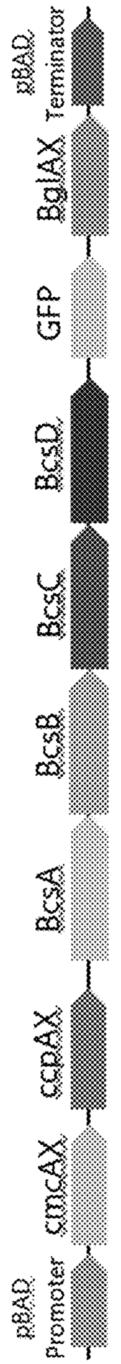
FIG. 3. A depiction of a construct comprising the cellulose synthesis genes cmcAx, ccpAx, BcsA, BcsB, BcsC, BcsD and BglAx, and GFP as a reporter gene. In this particular example, the construct also comprises a pBAD promoter and a pBAD terminator.

*Pseudomonas* strains CHA0, F113, FW300 N2E2 and Pf-5 will be utilised as a host for insertion of the bacterial biosynthetic cellulose machinery. The target insertion site in the genome of these strains is the attB site (SEQ ID NO 1: TGAGTTCGAATCTCACCGCCTCCGCCATAT). The cellulose synthesis genes (cmcAx, ccpAx, BcsA, BcsA, BcsC, BcsD, BglAx) will be inserted using a Mini CTX1 vector and a pFLP2 (Flp recombinase) vector. In this example, GFP will also be inserted as a reporter gene, this can be see in FIG. 3. A quorum sensing operon can also be added to the *Pseudomonas* strains to regulate the promoter controlling cellulose synthase gene expression (see FIG. 4). The quorum sensing operon, such as the PhzI/PhzR operon, will be under the control of a constitutive promoter.

3. Method

Conjugations

Recipient *Pseudomonas* strains, as well as *E. coli* donor and helper strains, were grown in 3 ml LB (with antibiotic when appropriate) at 37° C. with rolling for about 8 h. One milliliter of each culture was centrifuged at 8,000×g for 2 min in microcentrifuge tubes. The culture supernatants were aspirated, cell pellets were resuspended in 1 ml LB, and cell suspensions were centrifuged. Aspiration, resuspension, and centrifugation were repeated. The supernatant was aspirated and cell pellets were resuspended in 35 μl LB. Cell suspensions were spotted onto LB agar and incubated at 37° C. overnight. The cells were scraped off and resuspended in LB and serially diluted 10-fold, and 100 μl of each dilution was spread on Vogel-Bonner minimal medium (VBMM; 10 mM sodium citrate tribasic, 9.5 mM citric acid, 57 mM potassium phosphate dibasic, 17 mM sodium ammonium phosphate, 1 mM magnesium sulfate, 0.1 mM calcium chloride, pH 7.0) agar with antibiotic (gentamicin or tetracycline) and incubated at 37° C. overnight. Chromosomal integration of miniTn7 was confirmed by PCR with oligonucleotide primers.

Electroporations

Recipient *Pseudomonas* strains will be grown in 3 ml LB in duplicate at 37° C. with rolling for about 8 h. The two 3-ml cultures will then be pooled and dispensed into four microcentrifuge tubes. The cultures will be centrifuged at 8,000×g for 2 min. Each cell pellet will then be resuspended in 1 ml 300 mM sucrose and centrifuged twice. The four cell pellets will then be resuspended and pooled in a total of 300 μl of 300 mM sucrose. One hundred microliters of each suspension will be transferred to 1-mm-gap-width electroporation cuvettes. One hundred nanograms of pFLP2 plasmid will be added to each suspension. Cells will be electroporated at 1,800 V in an Eppendorf electroporator 2510. Nine hundred microliters of LB will be added to each electroporation. Recovery cultures will then incubated at 37° C. with rolling for 1 h. Cultures can be serially diluted 10-fold, spread on LB agar with antibiotic (carbenicillin), and incubated at 37° C. overnight.

Excision of Antibiotic Resistant Cassette by Flp-FRT Recombination

Recipient *Pseudomonas* strains containing chromosomal gentamicin resistance cassette flanked by FRT recombination sites were electroporated with pFLP2 plasmid. Transformants were streaked on LB with carbenicillin, as well as on LB with gentamicin, to screen for excision of the gentamicin resistance cassette by Flp recombination. Gentamicin-sensitive transformants were streaked from LB with carbenicillin to LB with 5% sucrose. Strains that have the pFLP2 plasmid are sucrose sensitive, while those that have lost the plasmid are sucrose resistant. Sucrose-resistant colonies were streaked on LB, LB with gentamicin, and LB with carbenicillin to confirm both excision of the gentamicin resistance cassette and loss of the pFLP2 plasmid.

Example 4—Protocol for Trial of Genetically Modified *Pseudomonas fluorescens*

1. Experimental Design

Maize plants (cultivar Pioneer P7892) will be raised in 24 cell module trays, using seeds, and then similarly-sized plants will be transplanted at the 3-4 leaf stage into ~10 L pots containing equal weight of commercially available sandy loam soil packed at the same bulk-density. Pots will be inoculated with one of nine inoculum treatments (Table 3). The control inoculum will consist of a mock inoculation using an equivalent volume of growth or other media lacking bacteria.

Five pot replicates will be used for each inoculum treatment. These will be arranged in five blocks (each of the nine treatments represented in each block) in a randomised block design on glasshouse benching, allowing data analysis to be conducted by Analysis of Variance (ANOVA). Environmental data will be captured in the glasshouse control system (temperature, relative humidity, solar radiation, set points).

Pots will be watered by hand daily according to the two treatments below, and will be fed twice a week with Hoagland's solution once they have reached 8-10 leaves, or beginning when they have clearly exhausted the nutrients available in the pot. Feed solution will replace irrigation treatments given to reach field capacity, and volume of feed will be the same for all treatments, topped up with water to field capacity. Pest and diseases may be controlled with appropriate fungicides and insecticides.

To determine if the expected increase in soil water holding capacity will lead to an increase in plant growth, the trial will be carried out under conditions of limited water supply in a simulated rain-fed environment. Increased water holding capacity will not affect plant growth unless water is limiting, so a "well-watered" control treatment will be compared to a water-limited treatment:

1. Well-watered daily. Plants will be watered to field capacity every day or every other day so that water never becomes limiting to growth. No effect of inoculum is expected via the mechanism of increased soil water holding capacity when water is not limiting. Effects though other mechanisms may be observed.
2. Cycling between field capacity and growth-limiting soil water deficit. After plants have fully established, showing growth of an additional 2-3 leaves after transplanting, they will be watered to field capacity and then allowed to dry through transpirational water loss until control plants show signs of water deficit (wilting, leaf curling, reduced stomatal conductance compared to well-watered plants). They will then be watered back to field capacity, and the cycle repeated. Pots with greater water holding capacity will sustain growth longer before available water is depleted, and therefore will be expected to have longer periods of unrestricted growth (noting that increased growth rate will also increase transpiration, so eventually increased growth will balance out the increased water holding capacity).

Pots will be spaced at 30 cm spacings in two rows arranged on 1 m wide benches. The glasshouse compartment will be heated to 25/20° C. day/night and supplementary illumination will be provided by high-pressure sodium lamps on a 16/8 hour day/night cycle. Maize has optimal growth at 25° C. (broad optimum between 21 and 27° C.).

Five replicate pots will be used for all treatments except for "No *Pseudomonas*" treatment where 10 replicates will be used (as all lines will be compared to this baseline). There will be two irrigation treatments.

Total number of pots=[(5 reps×8 inocula)+(10 reps×1 inoculum)]×2 treatments=100

Bench area=1×6 $m^2$ and 1×9 $m^2$ (30 cm×100, two rows on a 1 m wide bench, split over two benches containing either 2 or 3 "blocks"). Guard plants will be installed at the ends of each row (total of 8 plants) to reduce edge effects.

TABLE 3

Inoculum treatments

| Number | Description | Strain type | Observation | GM |
|---|---|---|---|---|
| 1 | No Pseudomonas | — | Negative Control | n/a |
| 2 | Natural Pseudomonas | CHA0 | Strain control | No |
| 3 | Natural Pseudomonas | F113 | Strain control | No |
| 4 | Natural Pseudomonas | FW300 N2E2 | Strain control | No |
| 5 | Natural Pseudomonas | Pf-5 | Strain control | No |
| 6 | Modified Pseudomonas | CHA0 | Test | Yes |
| 7 | Modified Pseudomonas | F113 | Test | Yes |
| 8 | Modified Pseudomonas | FW300 N2E2 | Test | Yes |
| 9 | Modified Pseudomonas | Pf-5 | Test | Yes |

2. Measurements

Water Holding Capacity:

Water holding capacity will be measured with a funnel technique in which soil and roots from pots is macerated to mix soil and roots, sampled to estimate gravimetric water content (weigh before and after drying), and then packed into a funnel. Water will be added to the top of the funnel and the amount of water retained will be recorded based on the mass of water applied and draining through the funnel. This is a rapid method that will allow the total water holding capacity between field capacity (water held after free drainage) and oven-dried soil to be calculated. This method includes the water between permanent wilting point and oven dryness which is considered too tightly bound to the soil to be available to the plant. Alternatively, a moisture release curve which is a plot of soil water potential (in MegaPascals, MPa) against gravimetric water content (g $g^{-1}$) can be calculated. The latter method allows calculation of the gravimetric water held between soil at field capacity (−0.01 MPa) and permanent wilting point (−1.4 MPa soil water potential), i.e. only the water available to the plant. One measurement per pot=100.

The funnel method will be validated as being responsive to soil cellulose content by using soil mixed with varying amounts of cellulose powder purchased from Fisher Scientific. Approximately 20 measurements.

Microbial Colonisation of the Rhizosphere:

A ~10 g sample of macerated soil/roots from the water capacity experiment (one sample per pot at harvest) will be mixed with water or buffer solution, and then filtered. Serial dilutions will be plated onto the appropriate selective media, and then incubated for 48 hrs at 25° C. Colony forming units (cfus) will be counted and cfu ml-1 calculated. A positive control would consist of inoculum applied to a sample of non-inoculated soil immediately prior to extraction (done at time of pot inoculation).

Three replicates per treatment and three serial dilutions plus controls=(3 reps×9 inocula×2 irrigation treatments×3 dilutions)+ (8 control inoculations×3 replicates×3 dilutions) =162+72=234 plates.

Carbon Content of the Soil:

A ~20 g sample of soil will be taken from the rhizosphere at harvest (prior to macerating soil/roots for the water capacity experiment), and any root fragments will be removed by sieving at 2 mm. Total organic carbon (TOC) will be measured by elemental analyser following hydrochloric acid treatment to remove carbonates.

One sample per pot=100 samples. Positive control analysis will also be conducted on soil mixed with cellulose (produced in the water capacity experiment)=20 samples.

Plant Health:

a) During plant growth, plant height and leaf number will be measured at weekly intervals using methods defined by agronomy practices.

Briefly, height will be defined as "from the soil surface to the highest point of the arch of the uppermost leaf whose tip is pointing down". Leaf number will be recorded using three rapid methods:

1. Number of leaf tips that have emerged from the whorl.
2. Number of leaves, starting from the lowest leaf and finishing with the last leaf that has arched over (leaf tip pointing down).
3. Number of leaves with visible collars (i.e. leaves emerged from the whorl).

b) Leaf chlorophyll content will be measured with a leaf chlorophyll meter (CCM-200) at weekly intervals on a standard leaf (e.g. uppermost arched leaf, two readings per leaf) validated with a standard curve (acetone extraction and spectrophotometer). 3 weeks×200 measurements=600.

c) At plant harvest, the total aboveground matter will be chopped, bagged and dried at 80° C. until fully dried. Dry weights per plant will be recorded (100 measurements).

Plant mineral content may also be measured using standard techniques.

REFERENCES

A number of publications are cited above in order to more fully describe and disclose the invention and the state of the art to which the invention pertains. Full citations for these references are provided below. The entirety of each of these references is incorporated herein.

Bae, S. O. et al. (2004) 'Features of bacterial cellulose synthesis in a mutant generated by disruption of the diguanylate cyclase 1 gene of *Acetobacter xylinum* BPR 2001', Applied Microbiology and Biotechnology, 65 (3), pp. 315-322. doi: 10.1007/s00253-004-1593-7.

BAILEY, M. J. et al. (1995) 'Site directed chromosomal marking of a fluorescent pseudomonad isolated from the phytosphere of sugar beet; stability and potential for marker gene transfer.', Molecular Ecology, 4 (6), pp. 755-764. doi: 10.1111/j.1365-294X.1995.tb00276.x.

Bashan, Y., et al. (2002) 'Alginate microbeads as inoculant carriers for plant growth-promoting bacteria'. Biol Fertil Soils, 35, 359-368.

Baynham, P. J. et al. (2006) 'The *Pseudomonas aeruginosa* ribbon-helix-helix DNA-binding protein AlgZ (AmrZ) controls twitching motility and biogenesis of type IV pili', Journal of Bacteriology, 188 (1), pp. 132-140. doi: 10.1128/JB.188.1.132-140.2006.

Brautaset, T. et al. (1994) 'Nucleotide sequence and expression analysis of the *Acetobacter xylinum* phosphoglucomutase gene', Microbiology, 140 (5), pp. 1183-1188. doi: 10.1099/13500872-140-5-1183.

Buldum, G. et al. (2018). 'Recombinant biosynthesis of bacterial cellulose in genetically modified *Escherichia coli*'. Bioprocess Biosyst Eng; 41 (2): 265-279. doi: 0.1007/s00449-017-1864-1.

Florea, M. et al. (2016). 'Engineering control of bacterial cellulose production using a genetic toolkit and a new cellulose producing strain'. PNAS; 113 (24): E3431-40.

Jang, W. D. et al. (2019) 'Genomic and metabolic analysis of *Komagataeibacter xylinus* DSM 2325 producing bacterial cellulose nanofiber', Biotechnology and Bioengineering, (July), pp. 1-10. doi: 10.1002/bit.27150.

Jozala, A. F., et al. (2014) 'Bacterial cellulose production by *Gluconacetobacter xylinus* by employing alternative culture media'. Appl Microbiol Biotechnol; 99 (3): 1181-90. Doi: 1007/s00253-014-6232-3.

Kawano, S., et al. (2008). 'Regulation of endoglucanase gene (cmcax) expression in *Acetobacter xylinum*'. J. Biosci. Bioeng. 106, 88-94. doi: 10.1263/jbb. 106.88

Klemm, D. et al. (2001) 'Bacterial synthesized cellulose—artificial blood vessels for microsurgery', Progress in Polymer Science, 26 (9), pp. 1561-1603. doi: 10.1016/S0079-6700 (01) 00021-1.

Koo, H. M. et al. (2000) 'Cloning, sequencing, and expression of UDP-glucose pyrophosphorylase gene from *Acetobacter xylinum* BRC5', Bioscience, Biotechnology and Biochemistry, 64 (3), pp. 523-529. doi: 10.1271/bbb.64.523.

Meyers A, Furtmann C, Gesing K, Tozakidis IEP, Jose J. 2019. Cell density-dependent auto-inducible promoters for expression of recombinant proteins in *Pseudomonas putida*. Microb Biotechnol 12:1003-1013

Rainey, P. B. and Bailey, M. J. (1996) 'Physical and genetic map of the *Pseudomonas fluorescens* SBW25 chromosome', Molecular Microbiology, 19 (3), pp. 521-533. doi: 10.1046/j.1365-2958.1996.391926.x.

Ryngajłło, M. et al. (2019) 'Comparative genomics of the *Komagataeibacter* strains-Efficient bionanocellulose producers', MicrobiologyOpen, 8 (5), pp. 1-25. doi: 10.1002/mbo3.731.

Sambrook, J., & R. (2001) 'Molecular cloning: a laboratory manual', Cold Spring Harbor Laboratory Press.

Standal, R., et al. (1994). 'A new gene required for cellulose production and a gene encoding cellulolytic activity in *Acetobacter xylinum* are colocalized with the bcs operon'. J. Bacteriol. 176, 665-672.

Tajima, K., et al. (2001). 'Cloning and sequencing of the beta-glucosidase gene from *Acetobacter xylinum* ATCC 23769'. DNA Res. 8, 263-269. doi: 10.1093/dnares/8.6.263.

Vandamme, E. J., et al. (1998). 'Improved production of bacterial cellulose and its application potential'. Polymer Degradation and Stability. 59 (1-3): 93-99. doi: 10.1016/S0141-3910 (97) 00185-7.

Walz, A. et al. (2002) 'A gene encoding a protein modified by the phytohormone indoleacetic acid', Proceedings of the National Academy of Sciences of the United States of America, 99 (3), pp. 1718-1723. doi: 10.1073/pnas.032450399.

Wong, H. C. et al. (1990) 'Genetic organization of the cellulose synthase operon in *Acetobacter xylinum*', Proceedings of the National Academy of Sciences of the United States of America, 87 (20), pp. 8130-8134. doi: 10.1073/pnas.87.20.8130.

For standard molecular biology techniques, see Sambrook, J., Russel, D. W. *Molecular Cloning, A Laboratory Manual*. 3 ed. 2001, Cold Spring Harbor, New York: Cold Spring Harbor Laboratory Press

The invention claimed is:

1. A genetically engineered root-associated bacterium for increased cellulose production, wherein cellulose production is increased at least 3 fold as compared to the wild-type bacterium, wherein the root-associated bacterium is a *Pseudomonas* bacterium, wherein the root-associated bacterium is genetically modified to overexpress at least seven proteins involved in synthesis and/or secretion of cellulose, wherein the root-associated bacterium comprises an exogenous bcsA gene, an exogenous bcsB gene, an exogenous bcsC gene, an exogenous bcsD gene, an exogenous ccpAx gene, an exogenous cmcAx gene and an exogenous bglAx gene.

2. The genetically engineered root-associated bacterium of claim 1, wherein the exogenous bcsA gene, exogenous bcsB gene, exogenous bcsC gene, exogenous bcsD gene, exogenous ccpAx gene, exogenous cmcAx gene and exogenous bglAx gene are on an exogenous nucleic acid molecule.

3. The genetically engineered root-associated bacterium according to claim 1, wherein the genes are each isolated from *K. xylinus*.

4. The genetically engineered root-associated bacterium according to claim 1, wherein expression of the genes is regulated by a cell-density quorum sensing system.

5. A composition comprising the genetically engineered root-associated bacterium of claim 1.

6. The composition according to claim 5, wherein the composition further comprises a fertiliser and/or a biofertiliser.

7. The genetically engineered root-associated bacterium according to claim 1, wherein the root-associated bacterium is *Pseudomonas fluorescens*.

8. The genetically engineered root-associated bacterium according to claim 1, wherein the root-associated bacterium is *Pseudomonas fluorescens* SBW25.

9. The genetically engineered root-associated bacterium according to claim 1, wherein the root-associated bacterium is *Pseudomonas fluorescens*F113.

10. The genetically engineered root-associated bacterium according to claim 1, wherein the root-associated bacterium is *Pseudomonas fluorescens* CHA0.

11. The genetically engineered root-associated bacterium according to claim 1, wherein the root-associated bacterium is *Pseudomonas fluorescens* Pf-5.

12. The genetically engineered root-associated bacterium according to claim 1, wherein the root-associated bacterium is *Pseudomonas fluorescens* FW300 N2E2.

13. The genetically engineered root-associated bacterium according to claim 1, wherein the root-associated bacterium is *Pseudomonas fluorescens* Pf-275, Pf0-1, FR1, DR133, or 2P24.

14. The composition according to claim 5, wherein the composition is applied to a plant in a liquid formulation.

15. The composition according to claim 5, wherein the composition is applied to a plant as a bacterial inoculum.

16. The composition according to claim 15, wherein the bacterial inoculum is a peat-based formulation.

17. The composition according to claim 5, wherein the genetically engineered root-associated bacterium is delivered to plants in microbeads.

18. The composition according to claim 5, wherein the composition is applied to a plant after planting but before harvest of said plant, or wherein the composition is applied to the soil before planting a plant.

19. The genetically engineered root-associated bacterium according to claim 1, wherein the root-associated bacterium is modified with exogenous genes further comprising a pgm gene, a galU gene, a cdg operon, and/or a dgc gene.

20. The genetically engineered root-associated bacterium according to claim 19, wherein the bcsA gene, bcsB gene, bscC gene, bcsD gene, ccpAx gene, cmcAx gene, bglAx gene, pgm gene, galU gene, cdg operon, and/or dgc gene are each isolated from *K. xylinus*.

21. The genetically engineered root-associated bacterium of claim 1, wherein cellulose production is increased at least 6 fold as compared to the wild-type bacterium.

22. A water-retention composition comprising the genetically engineered root-associated bacterium of claim 1, wherein the composition increases water retention around plant roots.

* * * * *